(12) United States Patent
Medina-Kauwe et al.

(10) Patent No.: US 9,850,293 B2
(45) Date of Patent: Dec. 26, 2017

(54) TARGETING TRASTUZUMAB-RESISTANT HER2+ BREAST CANCER WITH A HER3-TARGETING NANOPARTICLE

(71) Applicant: CEDARS-SINAI MEDICAL CENTER, Los Angeles, CA (US)

(72) Inventors: Lali K. Medina-Kauwe, Los Angeles, CA (US); Jessica Sims, Los Angeles, CA (US); Michael Taguaim, Los Angeles, CA (US); Chris Hanson, Los Angeles, CA (US); Xiaojiang Cui, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 14/678,972

(22) Filed: Apr. 4, 2015

(65) Prior Publication Data
US 2016/0060316 A1    Mar. 3, 2016

Related U.S. Application Data

(60) Provisional application No. 61/975,687, filed on Apr. 4, 2014.

(51) Int. Cl.
| | | |
|---|---|---|
| *A61K 38/00* | (2006.01) | |
| *C07K 14/475* | (2006.01) | |
| *A61K 31/517* | (2006.01) | |
| *A61K 31/704* | (2006.01) | |
| *A61K 38/18* | (2006.01) | |
| *A61K 31/713* | (2006.01) | |
| *C12N 15/87* | (2006.01) | |
| *A61K 47/62* | (2017.01) | |
| *A61K 47/68* | (2017.01) | |
| *A61K 39/00* | (2006.01) | |
| *A61K 48/00* | (2006.01) | |

(52) U.S. Cl.
CPC ........ *C07K 14/4756* (2013.01); *A61K 31/517* (2013.01); *A61K 31/704* (2013.01); *A61K 31/713* (2013.01); *A61K 38/1883* (2013.01); *A61K 47/62* (2017.08); *A61K 47/6855* (2017.08); *C12N 15/87* (2013.01); *A61K 38/00* (2013.01); *A61K 39/0011* (2013.01); *A61K 48/00* (2013.01); *C07K 2319/10* (2013.01); *C07K 2319/33* (2013.01); *C07K 2319/74* (2013.01); *C07K 2319/80* (2013.01)

(58) Field of Classification Search
CPC .......................... A61K 38/00; A61K 39/0011
See application file for complete search history.

(56) References Cited

U.S. PATENT DOCUMENTS

| | | |
|---|---|---|
| 5,391,723 A | 2/1995 | Priest |
| 5,559,099 A | 9/1996 | Wickham et al. |
| 6,333,396 B1 | 12/2001 | Filpula et al. |
| 8,541,568 B2 | 9/2013 | Yan et al. |
| 9,078,927 B2 | 7/2015 | Medina-Kauwe |
| 2003/0138432 A1 | 7/2003 | Glazier |
| 2003/0170826 A1 | 9/2003 | Rabinovich et al. |
| 2005/0042753 A1 | 2/2005 | Yang et al. |
| 2005/0048606 A1 | 3/2005 | Wang et al. |
| 2006/0014712 A1 | 1/2006 | Neuman |
| 2006/0093674 A1 | 5/2006 | Slobodkin et al. |

(Continued)

FOREIGN PATENT DOCUMENTS

| | | |
|---|---|---|
| EP | 1 374 812 A1 | 1/2004 |
| WO | WO-2002/062823 A2 | 8/2002 |

(Continued)

OTHER PUBLICATIONS

Agadjanian et al. (Nanomedicine (Lond). Mar. 2012; 7 (3): 335-52; author manuscript, pp. 1-26).*

(Continued)

*Primary Examiner* — Stephen Rawlings
(74) *Attorney, Agent, or Firm* — Morrison & Foerster LLP

(57) ABSTRACT

Disclosed herein are methods of treating cancer in a patient, the method comprising identifying a patient who is resistant to treatment with an anti-HER2 therapy; and administering to the patient a drug delivery molecule, comprising a polypeptide molecule adapted to target and/or penetrate a type of cell; a nucleic acid molecule bound to the polypeptide sequence via electrostatic interactions; and a chemical agent non-covalently linked to the nucleic acid sequence. Also disclosed are methods of inducing apoptosis in an anti-HER2 therapy resistant HER2+ breast cancer cell, the method comprising contacting the anti-HER2 therapy resistant HER2+ breast cancer cell with the drug delivery molecule. Further disclosed herein are methods of treating cancer in a patient, the method comprising identifying a patient who is resistant to anti-HER2 therapy; and administering to the patient a therapeutically effective amount of a drug delivery molecule, comprising a polypeptide molecule adapted to target and/or penetrate a type of cell; and a sulfonated corrole molecule bound to the polypeptide sequence. Finally disclosed herein are methods of inducing apoptosis in an anti-HER2 therapy resistant HER2+ breast cancer cell, the method comprising contacting the anti-HER2 therapy resistant HER2+ breast cancer cell with a drug delivery molecule, comprising a polypeptide molecule adapted to target and/or penetrate a type of cell; and a sulfonated corrole molecule bound to the polypeptide sequence.

14 Claims, 45 Drawing Sheets

(56) References Cited

U.S. PATENT DOCUMENTS

| | | | |
|---|---|---|---|
| 2008/0234183 | A1 | 9/2008 | Hallbrink et al. |
| 2010/0331273 | A1 | 12/2010 | Medina-Kauwe |
| 2011/0052697 | A1 | 3/2011 | Farokhzad et al. |
| 2011/0318338 | A1 | 12/2011 | Donald |
| 2012/0004181 | A1 | 1/2012 | Medina-Kauwe |
| 2012/0071540 | A1 | 3/2012 | Lu et al. |
| 2013/0065778 | A1 | 3/2013 | Weidhaas |
| 2014/0335025 | A1 | 11/2014 | Medina-Kauwe |
| 2015/0240231 | A1 | 8/2015 | Medina-Kauwe |
| 2016/0008481 | A1 | 1/2016 | Medina-Kauwe |
| 2016/0331840 | A1 | 11/2016 | Medina-Kauwe |

FOREIGN PATENT DOCUMENTS

| | | |
|---|---|---|
| WO | WO-2002/094318 A1 | 11/2002 |
| WO | WO-03/045492 A1 | 6/2003 |
| WO | WO-2007/137117 A2 | 11/2007 |
| WO | WO-2009/009441 A2 | 1/2009 |
| WO | WO-2009/009441 A3 | 1/2009 |
| WO | WO-2010/085665 A2 | 7/2010 |
| WO | WO-2010/085665 A3 | 7/2010 |
| WO | WO-2011/028850 A1 | 3/2011 |
| WO | WO-2013/175310 A2 | 11/2013 |
| WO | WO-2013/175310 A3 | 11/2013 |
| WO | WO-2014/022811 A1 | 2/2014 |
| WO | WO-2014/182868 A1 | 11/2014 |
| WO | WO-2015/109264 A1 | 7/2015 |
| WO | WO-2015/154059 A2 | 10/2015 |
| WO | WO-2015/154059 A3 | 10/2015 |
| WO | WO-2016/032595 A1 | 3/2016 |

OTHER PUBLICATIONS

Medina-Kauwe et al. (Gene Ther. Dec. 2001; 8 (23): 1753-61).*
Anders et al. (Oncology (Williston Park). Oct. 2008; 22 (11): 1233-90; pp. 1-10).*
Bae et al. (Breast Cancer Res. Treat. Jun. 2013; 139 (3): 741-500).*
Brady-West et al. (Asian Pac. J. Cancer Prev. 2011; 12 (8): 2139-43).*
Chandran et al. (BMC Proceedings 2012, 6 (Suppl. 4): O14; pp. 1).*
Bernstein et al. (Brain Res Bull. May 15, 2006; 69 (5): 546-59).*
Subik et al. (Breast Cancer (Auckl). May 20, 2010; 4: 35-41).*
International Search Report and Written Opinion issued in PCT/US2015/024400 dated Sep. 29, 2015.
Albanell and Baselga, Trastuzumab, a humanized anti-HER2 monoclonal antibody, for the treatment of breast cancer. Drugs Today (Barc). Dec. 1999;35(12):931-946 (abstract only).
Medina-Kauwe, Development of Adenovirus Capsid Proteins for Targeted Therapeutic Delivery. Ther Deliv. Feb. 2013;4(2):267-277.
Wang et al., Different Mechanisms for Resistance to Trastuzumab Versus Lapatinib in HER2-Positive Breast cancers-Role of Estrogen Receptor and HER2 Reactivation. Breast Cancer Res. 2011;13(6):R121.
Agadjanian, H. et al. (Apr. 14-18, 2007). "Modified Viral Capsid Protein Mediates Non-Viral Targeting of Unique Non-Covalent Drug Conjugates to HER2+ Breast Cancer Cells," *Proceedings of the AACR Annual Meeting* 48:357, Abstract # 1505 (Abstract Only), 2 pages.
Chavez, K. J. et al. (2010). "Triple Negative Breast Cancer Cell Lines: One Tool in the Search for Better Treatment of Triple Negative Breast Cancer," *Breast Dis.* 32(1-2):35-48, 17 pages.
International Preliminary Report on Patentability for PCT/US2015/022440 filed Mar. 25, 2015, 8 pages.
International Preliminary Report on Patentability for PCT/US2015/01870, dated May 11, 2015, filed Jan. 16, 2015, 6 pages.
International Search Report for PCT/US2015/011870, dated May 11, 2015, filed Jan. 16, 2015, 3 pages.
Koucht, A. et al. (Jun. 19, 2013). "Bacterial Invasion Factors: Tools for Crossing Biological Barriers and Drug Delivery?" *European Journal of Pharmaceutics and Biopharmaceutics* 84(2):242-250.

Medina-Kauwe, L.K.et al. (Aug. 24-29, 1997). "A Novel Gene Delivery System for Cell-Specific Targeting," *FASEB Journal*, 11(9):A862, Meeting: 17th International Congress of Biochemistry and Molecular Biology in conjunction with the Annual Meeting of the American Society for Biochemistry and Molecular Biology, San Francisco, CA.
Medina-Kauwe, L.K. et al. (Sep. 2000). "Assessing the Binding and Endocytosis Activity of Cellular Receptors Using GFP-Ligand Fusions," *BioTechniques* 29(3):602-609.
Medina-Kauwe, L.K. et al. (2001). "3PO, a Novel Non-Viral Gene Delivery System Using Engineered Ad5 Penton Proteins," *Gene Therapy* 8:795-803.
Medina-Kauwe, L.K. et al. (Nov. 2002). Ad5 Capsid Protein Uptake and Trafficking in HeLa Cells. *Molecular Biology of the Cell*, 13(Supplement):541a-542a, Abstract No. 3051, Meeting: 42nd Annual Meeting of the American Society for Cell Biology. San Francisco, CA, USA. American Society for Cell Biology.
Medina-Kauwe, L.K. (Nov. 14, 2003). "Endocytosis of Adenovirus and Adenovirus Capsid Proteins," *Adv. Drug Delivery Rev.* 55(11):1485-1496.
Medina-Kauwe, L.K. (2003). "Heregulin-Targeted Protein Uptake for Breast Cancer," NCI: 1R01CA102126-01, Abstract Only, 4 pages.
Medina-Kauwe, L.K. (2004). "Heregulin-Targeted Protein Uptake for Breast Cancer," NCI: 5R01CA102126-02, Abstract Only, 4 pages.
Medina-Kauwe, L.K. (2005). "Heregulin-Targeted Protein Uptake for Breast Cancer," NCI: 5R01CA102126-03, Abstract Only, 4 pages.
Medina-Kauwe, L.K. (2006). "Heregulin-Targeted Protein Uptake for Breast Cancer," NCI: 5R01CA102126-04, Abstract Only, 4 pages.
Medina-Kauwe, L.K. (2005). "Introduction to the Special Issue: Traveling the Intracellular Highway to Gene Therapy," *Gene Therapy* 12:863-864.
Medina-Kauwe, L.K. et al. (2005). "Intracellular Trafficking of Nonviral Vectors," *Gene Ther.* 12:1734-1751.
Medina-Kauwe, L.K. (2006). "Non-Viral Mediated Gene Delivery for Therapeutic Applications," Chapter 8 *in Gene Therapy for Neurological Disorders*, 115-140.
Medina-Kauwe, L.K. (2007). "A Novel Targeted Therapeutic Using Viral Capsid Protein," NCI: 1R21CA116014-01A2, Abstract Only, 4 pages.
Medina-Kauwe, L.K. (2008). "A Novel Targeted Therapeutic Using Viral Capsid Protein," NCI: 5R21CA116014-02, Abstract Only, 4 pages.
Medina-Kauwe, L.K. (2010). "Protein-DNA Drug Carriers for Tumor Targeting," NCI: 5R01CA129822-02, Abstract Only, 4 pages.
Medina-Kauwe, L.K. (2011). "Protein-DNA Drug Carriers for Tumor Targeting," NCI: 4R01CA129822-03, Abstract Only, 4 pages.
Medina-Kauwe, L.K. (2012). "Protein-DNA Drug Carriers for Tumor Targeting," NCI: 5R01CA129822-04, Abstract Only, 4 pages.
Medina-Kauwe, L.K. (2010). "Tumor Targeted Corroles for Detection and Intervention," NCI:1R01CA140995-01A1, Abstract Only, 5 pages.
Medina-Kauwe, L.K. (2011). "Tumor Targeted Corroles for Detection and Intervention," NCI:5R01CA140995-02, Abstract Only, 5 pages.
Medina-Kauwe, L.K. (2012). "Tumor Targeted Corroles for Detection and Intervention," NCI:5R01CA140995-03, Abstract Only, 5 pages.
Medina-Kauwe, L.K. (2013). "Tumor Targeted Corroles for Detection and Intervention," NCI:5R01CA140995-04, Abstract Only, 5 pages.
Medina-Kauwe, L.K. (2014). "Tumor Targeted Corroles for Detection and Intervention," NCI:5R01CA140995-05, Abstract Only, 5 pages.
Podo, F. et al. (2010, e-pub. Apr. 24, 2010). "Triple-Negative Breast Cancer: Present Challenges and New Perspectives," *Molecular Oncology* 4:209-229.

(56) References Cited

OTHER PUBLICATIONS

Project Information for project No. 1R01CA129822-01A2 (2009). Protein-DNA Drug Carriers for Tumor Targeting, Abstract Only, 2 pages.
Project Information for project No. 1R01CA129822-05A1 (2015). Protein-DNA Drug Carriers for Tumor Targeting, Abstract Only, 2 pages.
Ricci, M.S. et al. (Apr. 2006). "Chemotherapeutic Approaches for Targeting Cell Death Pathways," *Oncologist* 11(4):342-357, 26 pages.
Sims, J.D. et al. (Feb. 1, 2013). Treating Trastuzumab-Resistant HER2+ Breast Cancers with a HER3-Targeted Nanoparticle, *Cancer Research*, 73(3 Supp) Abstract No. A101. Meeting: AACR Special Conference on Tumor Invasion and Metastasis 2013. San Diego, CA, United States. Jan. 20, 2013-Jan. 23, 2013 Abstract Only.
Vellinga, J. et al. (2005, e-pub. Mar. 24, 2005). "The Adenovirus Capsid: Major Progress in Minor Proteins," *J. General Virology* 86:1581-1588.
Wolff, A.C. et al. (Nov. 1, 2013, e-pub. Oct. 7, 2013)."Recommendations for Human Epidermal Growth Factor Receptor 2 Testing in Breast Cancer: American Society of Clinical Oncology/College of American Pathologist Clinical Practice Guideline Update," *J. Clin. Oncology* 31(31):3997-4013.
Written Opinion of the International Searching Authority for PCT/US2015/022440, filed Mar. 25, 2015, 7 pages.
Written Opinion of the International Searching Authority for PCT/US2015/011870, dated May 11, 2015, filed Jan. 16, 2015, 5 pages.
U.S. Appl. No. 15/624,228, filed Jun. 15, 2017, for Medina-Kauwe et al.
Agadjanian, H. et al. (Feb. 2006). "Specific Delivery of Corroles to Cells via Noncovalent Conjugates with Viral Proteins," *Pharmaceutical Research* 23(2):367-377.
Agadjanian, H. et al. (Apr. 2008). "Corrole Conjugates: A Unique Approach to Tumor Targeting," *Proceedings of the American Association for Cancer Research Annual Meeting*, 49:549-550, Abstract 2328, Meeting: 99th Annual Meeting of the American-Association-for-Cancer-Research. San Diego, CA, USA. Apr. 12-16, 2008. Amer. Assoc. Canc. Res.
Agadjanian, H. et al. (Apr. 14, 2009). "Tumor Detection and Elimination by a Targeted Gallium Corrole," *Proc. Nat'l. Acad. Sci. USA* 106(15):6105-6110.
Baselga, J. et al. (Mar. 1996). "Phase II Study of Weekly Intravenous Recombinant Humanized Anti-p185$^{HER2}$ Monoclonal Antibody in Patients with HER2/neu-Overexpressing Metastatic Breast Cancer," *J. Clin. Oncol.* 14(3):737-744.
Blumenfeld, C.M. et al. (Nov. 2014, e-pub. Jun. 28, 2014). "Cellular Uptake and Cytotoxicity of a Near-IR Fluorescent Corrole-TiO$_2$Nanoconjugate", *Journal of Inorganic Biochemistry* 140:39-44, 11 pp.
Braslawsky, G.R. et al. (1990). "Antitumor Activity of Adriamycin (Hydrazone-linked) Immunoconjugates Compared with Free Adriamycin and Specificity of Tumor Cell Killing," *Cancer Res.* 50:6608-6614.
Brunello, E. et al. (Sep. 2013). "The Identification of a Small But Significant Subset of Patients Still Targetable With Anti-HER2 Inhibitors When Affected by Triple Negative Breast Carcinoma," *Journal of Cancer Research and Clinical Oncology* 139(9):1563-1568.
Chester, K.A. et al. (2000). "Clinical Applications of Phage-Derived sFvs and sFv Fusion Proteins," *Disease Markers* 16(1-2):53-62.
Choudhury, A. et al. (2004). "Small Interfering RNA (siRNA) Inhibits the Expression of the HER2/neu gene, Upregulates HLA Class I and Induces Apoptosis of HER2/neu Positive Tumor Cell Lines," *International Journal of Cancer* 108:71-77.
Cobleigh, M.A. et al. (1998). "Efficacy and Safety of Herceptin™ (Humanized Anti-HER2 Antibody) as a Single Agent in 222 Women with HER2 Overexpression Who Relapsed Following Chemotherapy for Metastatic Breast Cancer," *376 Proc. Am. Soc. Clin. Oncol.* 17:97a, 3 pages.

Deng, X. et al. (Feb. 22, 2014, e-pub. Feb. 4, 2014). "Hyaluronic Acid-Chitosan Nanoparticles for Co-Delivery of MiR-34a and Doxorubicin in Therapy Against Triple Negative Breast Cancer," *Biomaterials* 35(14):4333-4344.
Denny, W.A. (1989). "DNA-Intercalating Ligands as Anti-Cancer Drugs: Prospects for Future Design," *Anticancer Drugs Des.* 4(4):241-263.
Drummond, D.C. et al. (1999). "Optimizing Liposomes for Delivery of Chemotherapeutic Agents to Solid Tumors," *Pharmacol. Rev.* 51(4):691-743.
European Supplemental Search Report for EP Application No. EP15773654.7, dated Aug. 11, 2017 pages.
Faltus, T. et al. (Nov./Dec. 2004). "Silencing of the HER2/neu Gene by siRNA Inhibits Proliferation and Induces Apoptosis in HER2/neu-Overexpressing Breast Cancer Cells," *Neoplasia* 6(6):786-795.
Glockshuber, R. et al. (Feb. 1990). "A Comparison of Strategies to Stabilize Immunoglobin F$_v$-Fragments," *Biochem.* 29(6):1362-1367.
Goldman, R. et al. (1990). "Heterodimerization of the erbB-1 and erbB-2 Receptors in Human Breast Carcinoma Cells: A Mechanism for Receptor Transregulation," *Biochemistry* 29(50):11024-11028.
Goren, D. et al. (1996). "Targeting of Stealth Liposomes to erbB-2 (Her/2) Receptor: in Vitro and in Vivo Studies," *Br. J. Cancer* 74:1749-1756.
Hwang, J.Y. et al. (2012). "Multimodality Imagining In Vivo for Preclinical Assessment of Tumor-Targeted Doxorubicin Nanoparticles," *PLoS One* 7(4): e34463, 9 pages.
Hwang, J.Y. et al. (Jun. 18, 2013). "Analysis of Targeted Viral Protein Nanoparticles Delivered to HER2+Tumors," *J. Vis. Exp.* 76:50396.
International Search Report dated Sep. 29, 2015, for PCT/US2015/024400 filed on Apr. 4, 2015, 6 pages.
International Search Report and Written Opinion for PCT/US2017/034719, dated Aug. 14, 2017, filed May 26, 2017, 14 pages.
Jeschke, M. et al. (Mar. 3, 1995). "Targeted Inhibition of Tumor-Cell Growth by Recombinant Hereguilin-Toxin Fusion Proteins," *Intl. J. Cancer*, 60(5):730-739.
Kedes, L.H. et al. (Aug. 2002). "A Novel Gene Delivery System Targeted to Breast Cancer Cells," Report DAMD17-99-1-9378 prepared for U.S. Army medical research, (38 pages).
Kute, T. et al. (2004), "Development of Herceptin Resistance in Breast Cancer Cells," *Cytometry Part A* 57:86-93.
Kutty, R.V. et al. (Apr. 1, 2014). "Nanomedicine for the Treatment of Triple-Negative Breast Cancer," *Nanomedicine* 9(5):561-564.
Medina-Kauwe, L.K. et al. (2002). "Using GFP-Ligand Fusions to Measure Receptor-Mediated Endocytosis in Living Cells," *Vitamins and Hormones*, 65:81-95.
Medina-Kauwe, L.K. (Jun. 2007). "Targeting siRNA Missiles to Her2+ Breast Cancer," retrieved from http://www.dtic.mil/cgi-bin/GetTRDoc?AD=ADA472023, 13 pages.
Medina-Kauwe, L.K. (Aug. 2002). "A Novel Gene Delivery System Targeted to Breast Cancer," Report by University of Southern California, Report Sponsored by U.S. Army Medical Research and Material Command, Fort Detrick, Maryland, 14 pages.
Medina-Kauwe, L.K. (2008). "Targeting Sirna Missiles to Her2+ Breast Cancer", U.S. Army Medical Research and Material Command Fort Detrick, Maryland, (10 pages).
Minotti, G. et al. (2004). "Anthracyclines: Molecular Advances and Pharmacologic Developments in Antitumor Activity and Cardiotoxicity," *Pharmacol. Rev.* 56(2):185-229.
Non-Final Office Action for U.S. Appl. No. 14/796,758 dated Mar. 30, 2017 filed Jul. 10, 2015.
Park, J.W. et al. (2002). "Anti-HER2 Immunoliposomes: Enhanced Efficacy Attributable to Targeted Delivery," *Clin. Cancer Res.* 8:1172-1181.
Rentsendorj, A. et al. (2006; e-published on Feb. 16, 2006). "Typical and Atypical Trafficking Pathways of Ad5 Penton Base Recombinant Protein: Implications for Gene Transfer," *Gene Therapy* 13:821-836.
Schmidt, M. et al. (1999). "A Suppression of Metastasis Formation by Recombinant Single Chain Antibody-Toxin Targeted to Full-Length and Oncogenic Variant EGF Receptors," *Oncogene* 18:1711-1721.

(56) References Cited

OTHER PUBLICATIONS

Sepp-Lorenzino, L. et al. (Apr. 18, 1996). "Signal Transduction Pathways Induced by Heregulin in MDA-MB-453 Breast Cancer Cells," *Oncogene* 12(8):1679-1687.

Shemesh, C.S. et al. (Mar. 19, 2014, e-pub. Mar. 19, 2014). "Indocyanine Green Loaded Liposome Nanocarriers for Photodynamic Therapy Using Human Triple Negative Breast Cancer Cells", *Photodiagnosis and Photodynamic Therapy* 11(2):193-203.

Sims J. D. et al. (Dec. 2013). "Abstract P5-08-08: A Human Epidermal Growth Factor Receptor 3 (HER3)-Binding Nanoparticle Targets and Kills Herceptin (R)-Resistant Human Epidermal Growth Factor Receptor 2 (HER2)-Positive Breast Cancer," *Cancer Research* 73(Suppl. 24) 36th Annual San Antonio Breast Cancer Symposium; San Antonio, TX, USA Dec. 10-14, 2013 Abstract Only.

Sims J.D. et al. (Oct. 2014). "Abstract 4487:Targeting Trastuzumab-Resistant HER2+ Breast Cancer With a HER3-Targeting Nanoparticle," *Cancer Research* 74(19):Suppl. S. 105th Annual Meeting of the American-Association-For-Cancer-Research (AACR); San Diego, CA, USA; Apr. 5-9, 2014 Abstract Only.

Sims, J.D. et al. (2015, e-pub. Aug. 31, 2015). "A Corrole Nanobiologic Elicits Tissue-Activated MRI Contrast Enhancement and Tumor-Targeted Toxicity," *J. Control Research* 217:92-101.

Siwak, D.R. et al. (Apr. 2002). "The Potential of Drug-Carrying Immunoliposomes as Anticancer Agents," *Clin. Cancer Res.*, 8:955-956.

Slamon, D.J. et al. (Mar. 15, 2001). Use of Chemotherapy plus a monoclonal antibody against HER2 for metastatic breast cancer that overexpresses HER2, N. Engl. J. Med., 344(1 1):783-792.

Sliwkowski, M.X. et al. (May 20, 1994). "Coexpression of erbB2 and erbB3 proteins Reconstitutes a High Affinity Receptor for Heregulin," *Journal of Biological Chemistry*, 269(20):14661-14665.

Taqavi et al. (Aug. 17, 2008). "Developing Macrocyclic Fluorescent Probes for in Vivo Molecular Imaging," *Abstracts of Papers American Chemical Society*, 236:654-INOR. Meeting: 236th National Meeting of the American-Chemical-Society. Philadelphia, PA, USA. Aug. 17-21, 2008. Amer. Chem. Soc.

Trail, P.A. et al. (1992). :"Antigen-Specific Activity of Carcinoma-Reactive BR64-Doxorubicin Conjugates Evaluated in Vitro and in Human Tumor Xenograft Models," *Cancer Res.* 52:5693-5700.

Trail, P.A. et al. (Jul. 9, 1993). "Cure of Xenografted Human Carcinomas by BR96-Doxorubicin Immunoconjugates," *Science* 261(5118):212-215.

Trail, P.A.et al. (May 2003, e-pub. Jan. 16, 2003). "Monoclonal Antibody Drug Immunoconjugates for Targeted Treatment of Cancer," *Cancer Immunol Immunother*. 52(5):328-337.

Vogel, C.L. et al. (Feb. 1, 2002). "Efficacy and Safety of Trastuzumab as a Single Agent in First-Line Treatment of HER2-Overexpressing Metastatic Breast Cancer," *J. Clin. Oncol.* 20(3):719-726.

Written Opinion of International Search Authority for PCT/US2008/69239 dated Jan. 28, 2009 and filed on Jul. 3, 2008.

Xiong, W. et al. (Jan. 2006). "Regulatable Gutless Adenovirus Vectors Sustain Inducible Transgene Expression in the Brain in the Presence of an Immune Response Against Adenoviruses," J. Viro. 80(1):27-37.

Year of Publication retrieved from <http://rep945.infoeach.com/view-OTQ1fDgzNDY1NQ==.html>, last visited on Jun. 21, 2017, 2 pages.

Zabner, J.et al. (Aug. 11, 1995). "Cellular and Molecular Barriers to Gene Transfer by a Cationic Lipid," *Journal of Biological Chemistry* 270(32):18997-19007.

* cited by examiner

A  Human
   Mouse
20 SEVGNSQAVCPGTLNGLSVTGDAENQYQTLYKLYERCEVVMGNLEIVLTGHNADL
   33M33333333333333333333333D33333333333K3
   SFLQWIREVTGYVLVAMNEFSTLPLPNLRVVRGTQVYDGKFAIFVMLNYNTNSSH
   33333333333333333333333V3
   ALRQLRLTQLTEILSGGVYIEKNDKLCHMDTIDWRDIVRDRDAEIVVKDNGRSCP
   333333F3333333L33333333333333333333333333VP3333333N33GN3
   PCHEVCKGRCWGPGSEDCQTLTKTICAPQCNGHCFGPNPNQCCHDECAGGCSGPQ
   3333333333333P3333I333333333333R3                    239

TARGETING TRASTUZUMAB-RESISTANT HER2+ BREAST CANCER WITH A HER3-TARGETING NANOPARTICLE

RELATED APPLICATIONS

The present application claims priority from the U.S. Provisional Application Ser. No. 61/975,687, filed on Apr. 4, 2014, by Lali K. MEDINA-KAUWE et al. and entitled "TARGETING TRASTUZUMAB RESISTANT HER2+ BREAST CANCER WITH A HER3- TARGETING NANOPARTICLE," the entire disclosure of which is incorporated herein by reference, including the drawings.

STATEMENT REGARDING FEDERALLY SPONSORED RESEARCH

This invention was made with government support under Grant No. CA140995 and Grant No. CA129822 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 4, 2015, is named EOS006US_SEQLISTING.txt and is 17 kilobytes in size.

FIELD OF THE INVENTION

The present invention is in the field of therapeutics, and more specifically in the field of treating cancer.

BACKGROUND OF THE DISCLOSURE

It is well-known that the overexpression of the HER family of receptors, for example HER1 (EGFR), HER2, HER3, and HER4 receptors, in a cell leads to strong and constant proliferative signaling in the cell, which ultimately leads to the development of certain types of cancer, for example breast cancer. HER2-positive breast cancers represent almost a quarter of invasive breast cancers and are indicative of poor patient survival. Trastuzumab is a monoclonal antibody that interferes with the HER2/neu receptor. It is currently marketed under several trade names, such as Herceptin®, for the treatment of certain breast cancers. Pertuzumab is another monoclonal anti-HER2 antibody, which is used in cancer treatment. Lapatinib is a small molecule organic compound that exerts a therapeutic effect in breast cancer. These therapies are generally used as a last line defense against cancer, after other therapeutic regimens have failed. Unfortunately, although many patients with HER2-positive breast cancer initially respond to these anti-HER2 treatments, a significant portion of them develop resistance to these therapies. Once resistance to a late stage therapeutic is developed, the options for the treatment become very few indeed. Consequently, there is a great need to develop new drugs that are effective against these HER2+ tumors that are non-responsive or have become resistant to these therapies.

SUMMARY OF THE INVENTION

Disclosed herein are methods of treating cancer in a patient, the method comprising identifying a patient who is resistant to treatment with an anti-HER2 therapy; and administering to the patient a drug delivery molecule, comprising a polypeptide molecule adapted to target and/or penetrate a type of cell; a nucleic acid molecule bound to the polypeptide sequence via electrostatic interactions; and a chemical agent non-covalently linked to the nucleic acid sequence. Also disclosed are methods of inducing apoptosis in an anti-HER2 therapy resistant HER2+ breast cancer cell, the method comprising contacting the anti-HER2 therapy resistant HER2+ breast cancer cell with the drug delivery molecule.

Further disclosed herein are methods of treating cancer in a patient, the method comprising identifying a patient who is resistant to anti-HER2 therapy; and administering to the patient a therapeutically effective amount of a drug delivery molecule, comprising a polypeptide molecule adapted to target and/or penetrate a type of cell; and a sulfonated corrole molecule bound to the polypeptide sequence. Finally disclosed herein are methods of inducing apoptosis in an anti-HER2 therapy resistant HER2+ breast cancer cell, the method comprising contacting the anti-HER2 therapy resistant HER2+ breast cancer cell with a drug delivery molecule, comprising a polypeptide molecule adapted to target and/or penetrate a type of cell; and a sulfonated corrole molecule bound to the polypeptide sequence.

BRIEF DESCRIPTION OF THE DRAWINGS

FIG. 4 (B) illustrates UV/V absorbances of filtrates and retentates during the DNA-Dox assembly.

Immunoblot of fractions 1-5 is also depicted with a penton base antibody used to identify HerPBK10.

Figure 6:
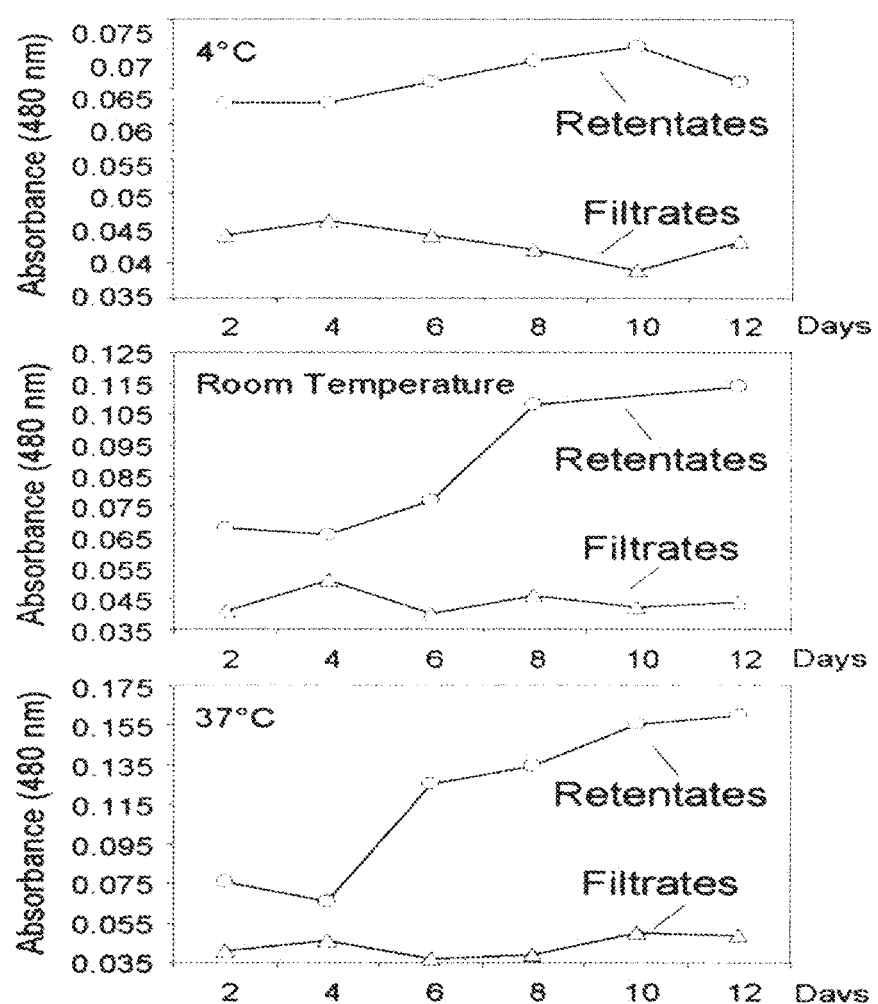
Figure 6:
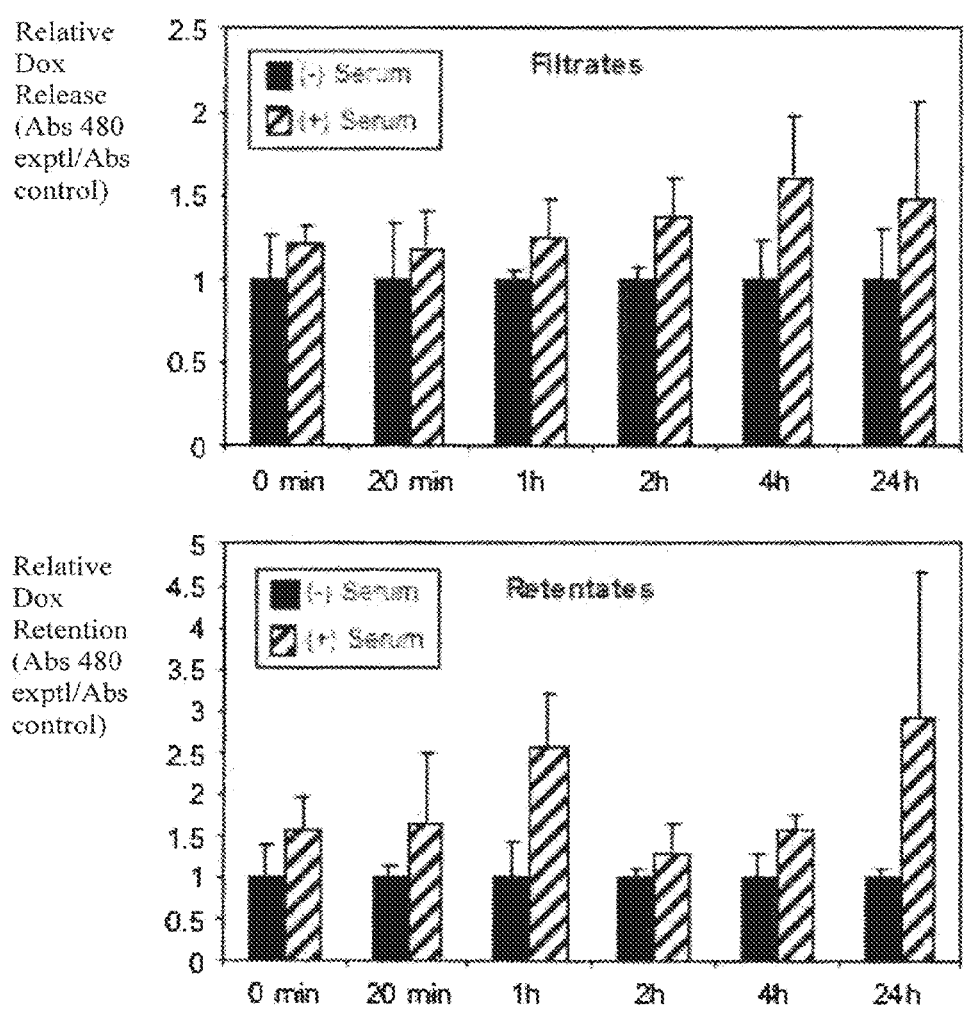

FIG. 6 (A) illustrates conjugate stability under different storage conditions, or in serum. HerDox was incubated up to 12 days at 4° C., Room Temperature, or 37° C. Samples were filtered through ultrafiltration spin columns every other day. Retentate and filtrate absorbances were measured at 480 nm to determine relative Dox retention or release from conjugates, respectively.

FIG. 6 (B) mimics extended exposure of HerDox to cells in culture medium. HerDox immobilized on Ni-NTA beads were incubated with bovine serum in DMEM for the indicated times at 37° C. before each sample was pelleted. Absorbance of supernatants (Filtrates) and bead eluates (Retentates) were measured at 480 nm to detect Dox. Relative Dox release or retention in serum is expressed as normalized to control (corresponding sample lacking serum). N=3 per time point. T tests ($P<0.05$) of samples compared to controls showed no significant differences.

Figure 7:
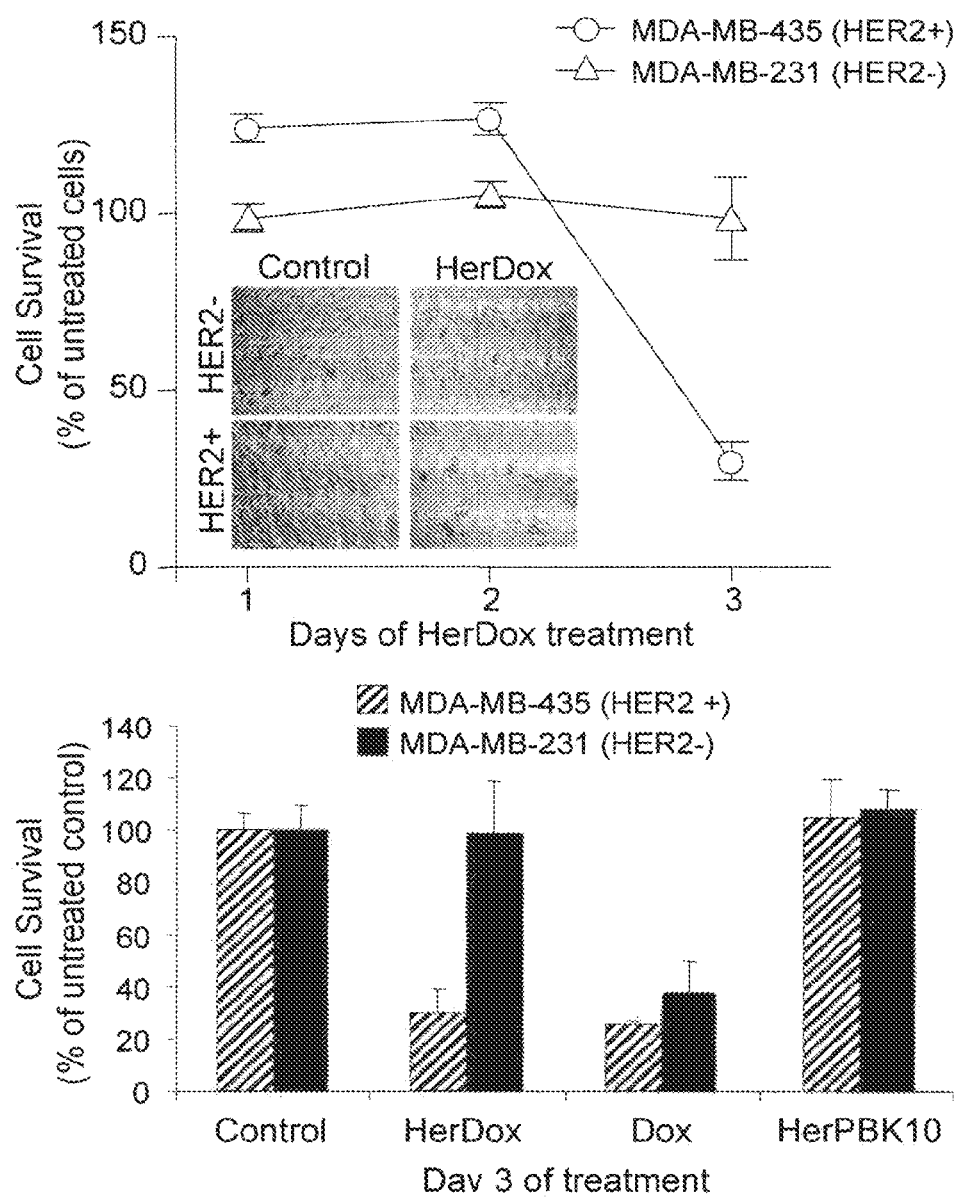

FIG. 7 illustrates targeted toxicity. Each cell line was exposed to rHerDox (0.5 μM Dox conc), Dox alone (0.5 μM), or HerPBK10 alone for 4 hours at 37° C. in complete (i.e. serum-containing) media, followed by aspiration to remove free conjugate, and addition of fresh medium while cells are grown continuously. Cell titer was determined by metabolic (i.e. MTT) assay. FIG. 7 upper panel illustrates the effect of HerDox on MDA-MB-231 (HER2−) and MDA-MB-435 (HER2+) cell survival. Relative surviving cell numbers are represented as a % of corresponding untreated cells. FIG. 7 lower panel illustrates comparison of HerDox, Dox alone, or HerPBK10 alone on HER2− and HER2+ cell survival. Relative survival (as % of untreated cells) is shown for Day 3 of treatment.

Figure 8:
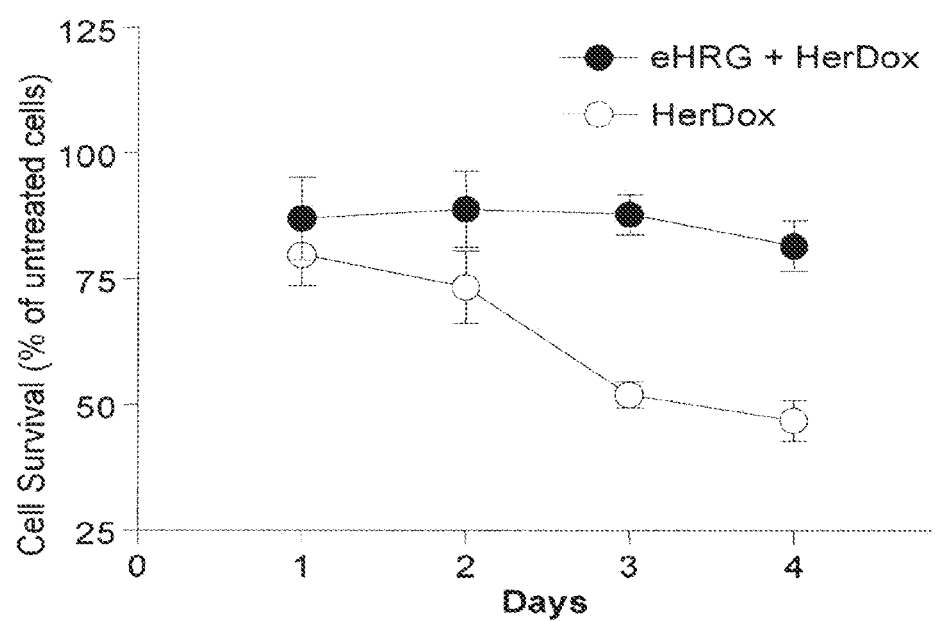

FIG. 8 illustrates receptor specificity. MDA-MB-435 (HER2+) cells were incubated with free ligand (eHRG) at 10× molar excess of HerDox for one hour at 4° C. Media was aspirated to remove free eHRG and fresh media containing HerDox (0.5 μM) was added to cells. Cell survival was measured by MTT assay and represented as a % of relative untreated cell numbers.

Figure 9:
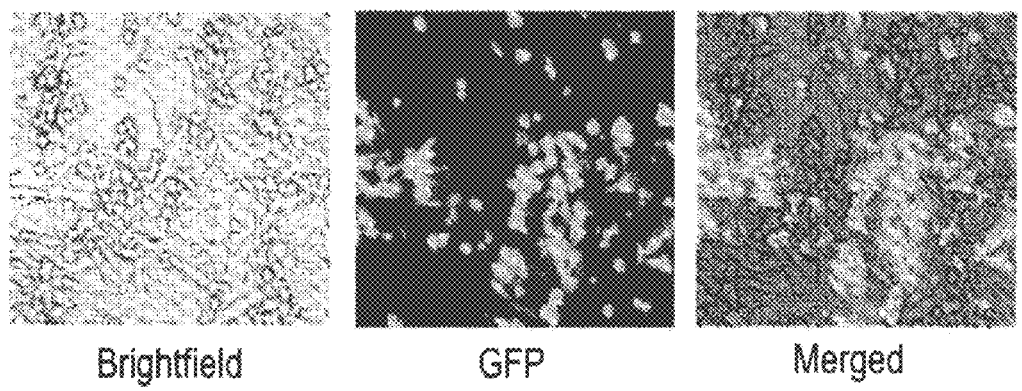
Figure 9:
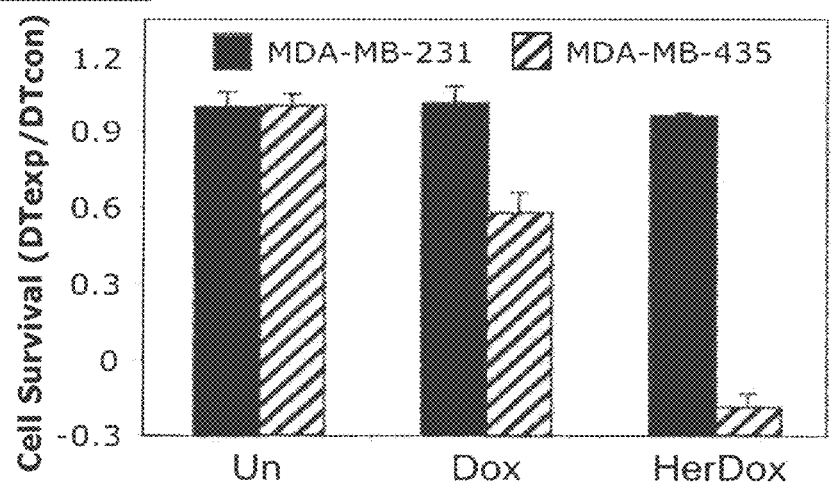
Figure 9:
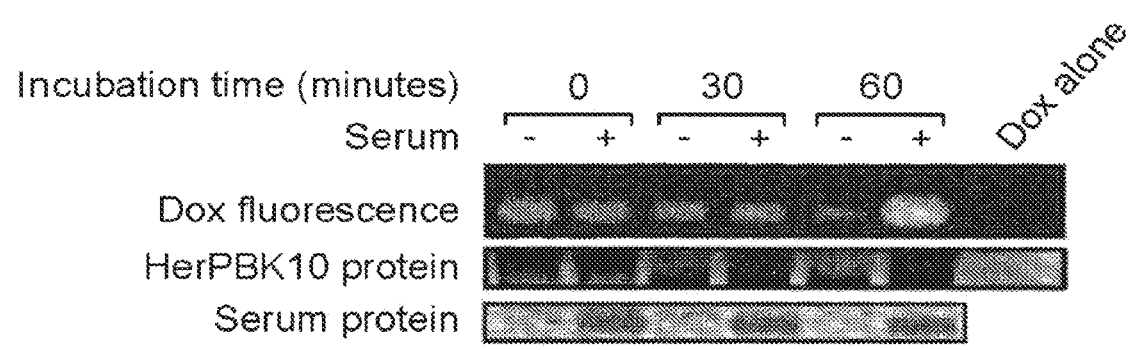

FIG. 9 (A) illustrates targeting in a mixed cell culture. Equal numbers of MDA-MB-435 and GFP(+) MDA-MB-231 cells were treated with Dox alone (0.5 Her-Dox (containing 0.5 μM Dox), or HerPBK10 (1.2 μg/well, equivalent to HerPBK10 in HerDox). Wells were assayed for GFP fluorescence (to determine relative MDA-MB-231 number) and crystal violet staining (to determine total cell number).

FIG. 9 (B) further illustrates targeting in a mixed cell culture. Cell survival was determined by calculating the relative doubling time (DT) of experimental (exp) cells normalized by control (con) cells based on the crystal violet stains (total cells) and GFP fluorescence (MDA-MB-231 cells). The DT of MDA-MB-435 was determined by subtracting the DT of MDA-MB-231 from the total cell DT. Relative survival is shown for Day 2 of treatment.

FIG. 9 (C) illustrates that there is stability in cell culture. Aliquots of culture media containing HerDox (after incubation for the indicated times at 37° C.) were electrophoresed on a 2% agarose gel. HerDox incubated at 37° C. in HEPES-buffered saline, lacking serum, was processed in parallel. Dox fluorescence was visualized by UV excitation. Free Dox (Dox alone) is not retained in the gel whereas Dox incorporated in HerDox is. To align fluorescent bands with HerPBK10 and assess loading per lane, the gel was stained with Coomassie blue, which also identified serum protein from culture media samples.

Figure 10:
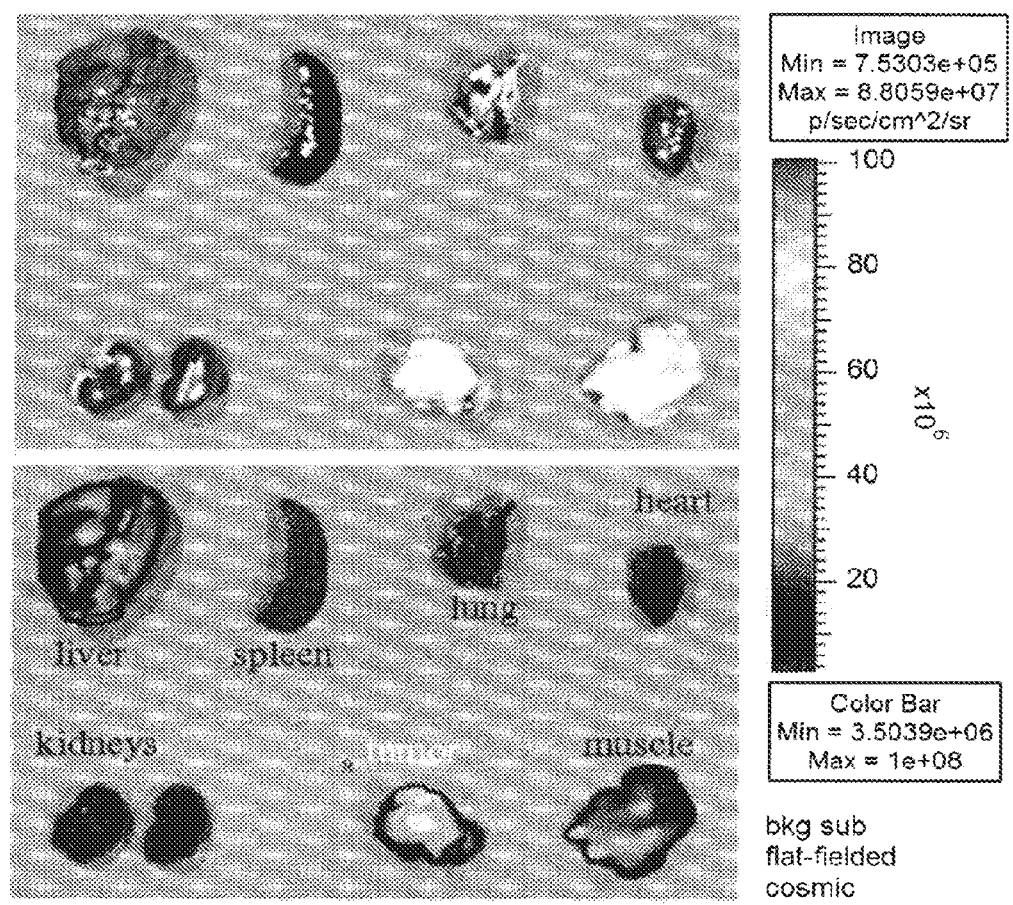

FIG. 10 illustrates preferential targeting of GFP-Her to HER2+ tumors. Tumor-bearing mice were injected with 3 nmol of GFP-Her via the tail vein. Tissues were harvested at 3.5 h after injection and visualized using a Xenogen small-animal imager. GFP fluorescence is pseudo-colored red (blue pseudo-coloring indicates no fluorescence whereas GFP intensity is reflected by a color value shift toward red in the color bar).

Figure 11:
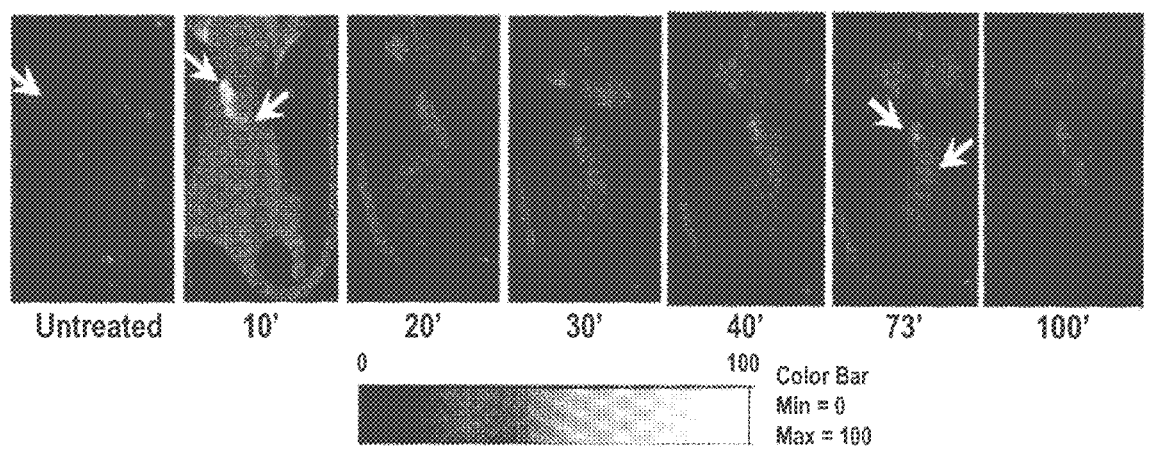
Figure 11:
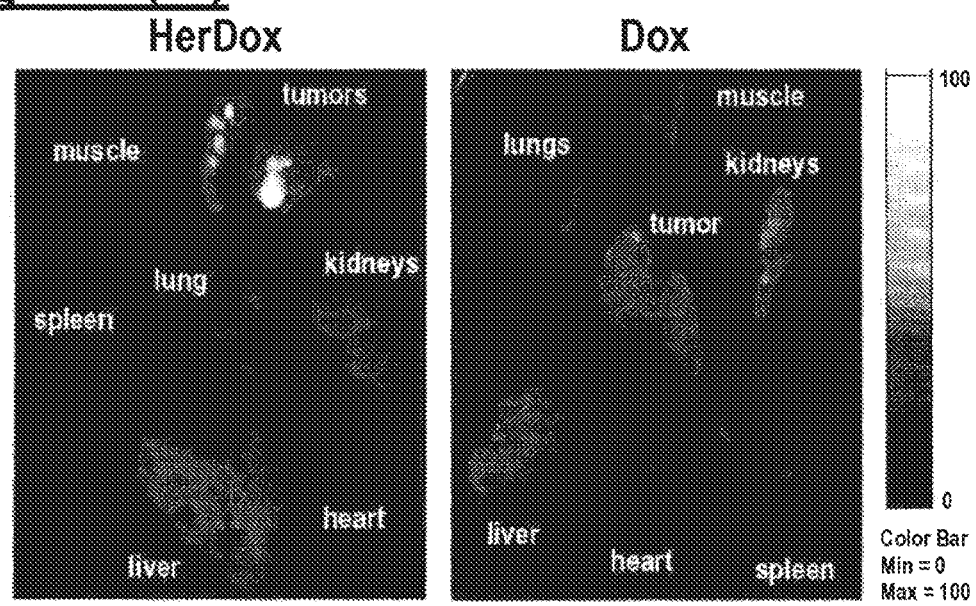

FIG. 11 (A) illustrates preferential targeting of HerDox to HER2+ tumors. Tumor-bearing mice were injected with 0.75 nmol of HerDox or Dox via the tail vein and imaged with a custom small animal imager. FIG. 11 (A) depicts imaging of live mice after IV delivery of HerDox. Tumors are indicated by arrows.

FIG. 11 (B) further illustrates preferential targeting of HerDox to HER2+ tumors. Tumor-bearing mice were injected with 0.75 nmol of HerDox or Dox via the tail vein and imaged with a custom small animal imager. FIG. 11 (B) depicts imaging of tumors and tissues harvested at 3 hours after injection of HerDox or Dox. Fluorescence signal from Dox is pseudo-colored according to the color bar, with a shift toward 100 indicating high fluorescence intensity. FIG. 11 (B) illustrates a comparison of the targeted delivery of Dox to HER2+ breast cancer cells with minimal delivery to other organs and tissues using a delivery system in accordance with an embodiment of the present invention (left panel), as compared with Dox administered alone (right panel).

Figure 12:
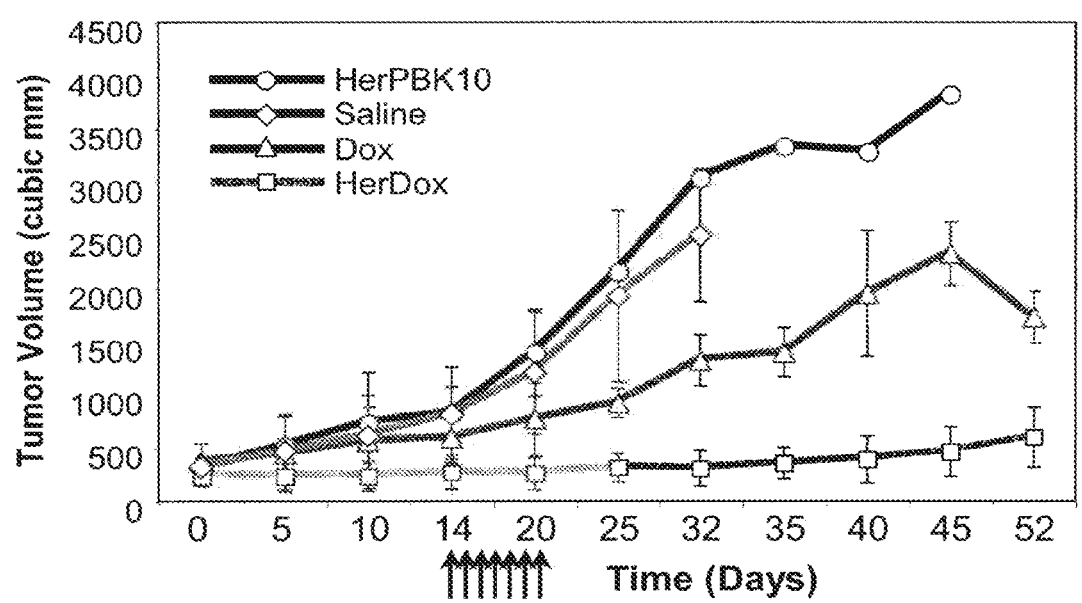
Figure 12:
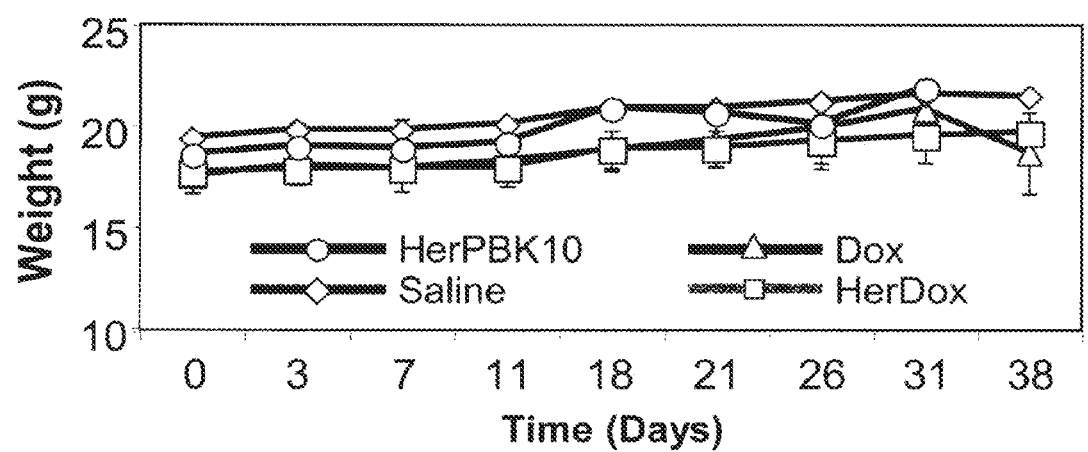
Figure 12:
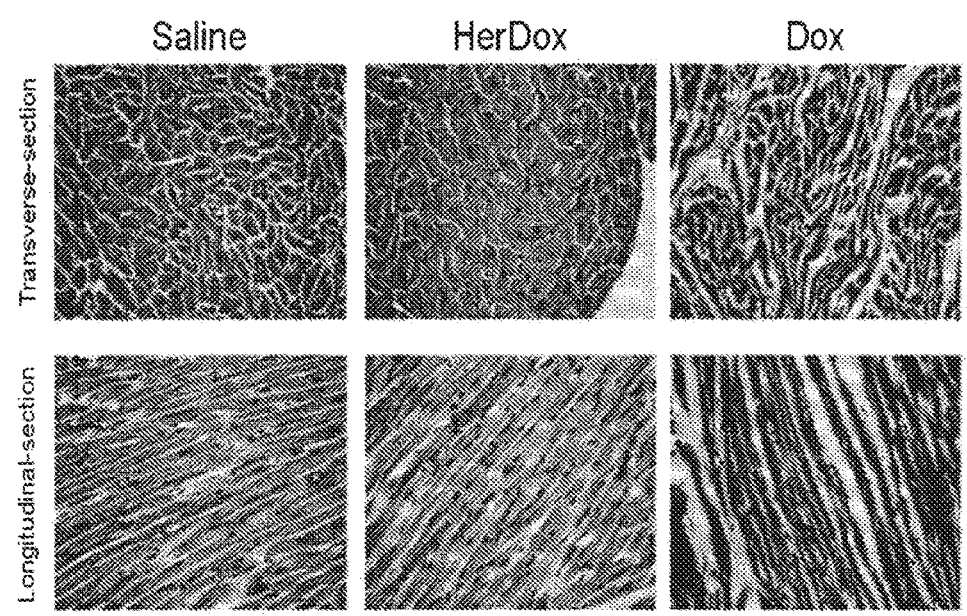
Figure 12:
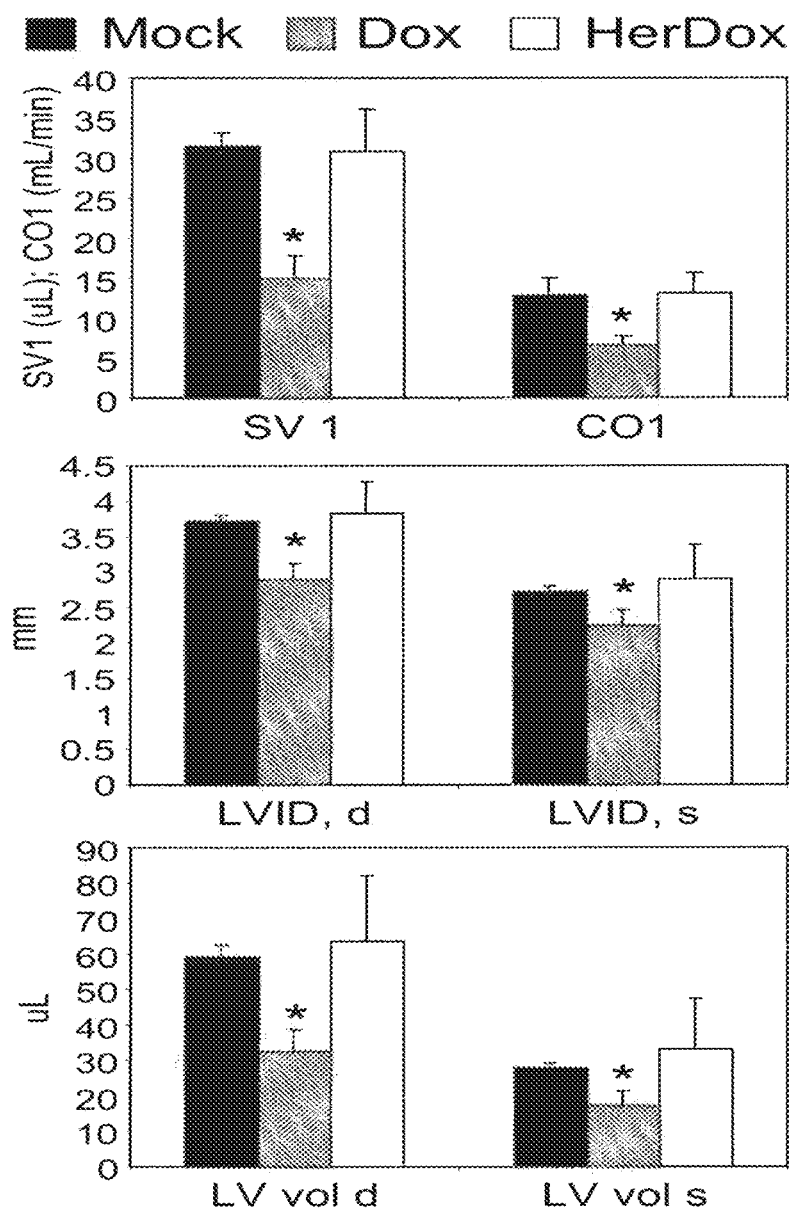

FIG. 12 (A) illustrates comparison of HerDox and Dox on tumor growth.

FIG. 12 (B) illustrates comparison of HerDox and Dox on animal weight.

FIG. 12 (C) illustrates comparison of HerDox and Dox on cardiac tissue.

FIG. 12 (D) illustrates comparison of HerDox and Dox on cardiac function.

Figure 13:
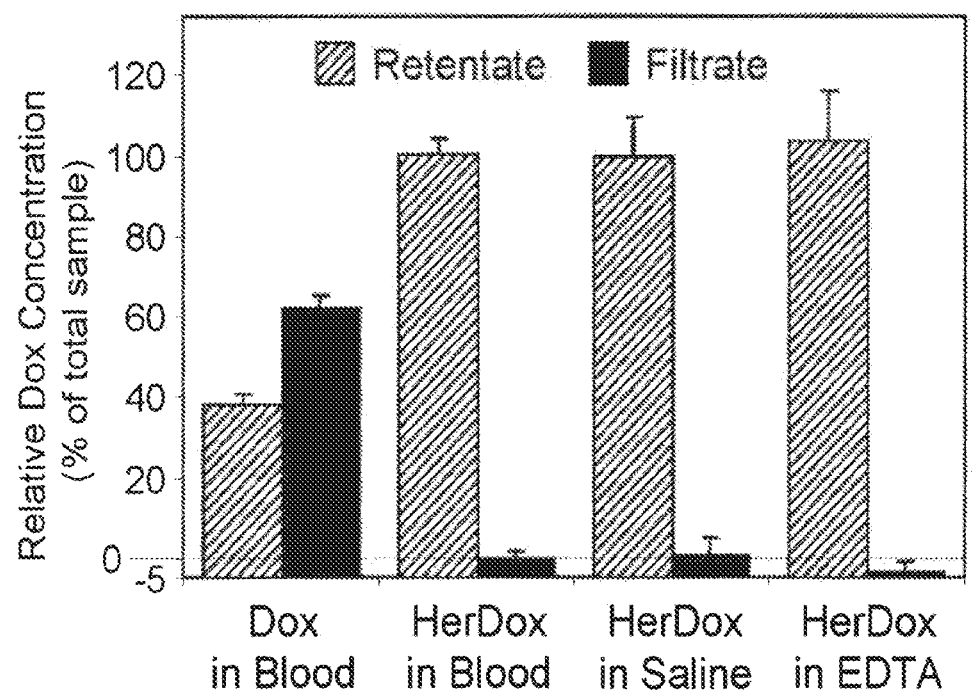

FIG. 13 illustrates stability in mouse whole blood. Freshly collected whole blood was processed by ultrafiltration through 10K MW cutoff membranes after up to 1 hour incubation with HerDox or Dox at 37° C. As 0.5 mM EDTA was used as an anticoagulant, HerDox in EDTA alone (− blood) was processed in parallel. Bars represent fluorescence of retained (retentates) or released (filtrates) Dox as a percentage of the total fluorescence of each sample. Scale of Y-axis is adjusted to show presence of filtrate samples. N=3 per treatment.

Figure 14:
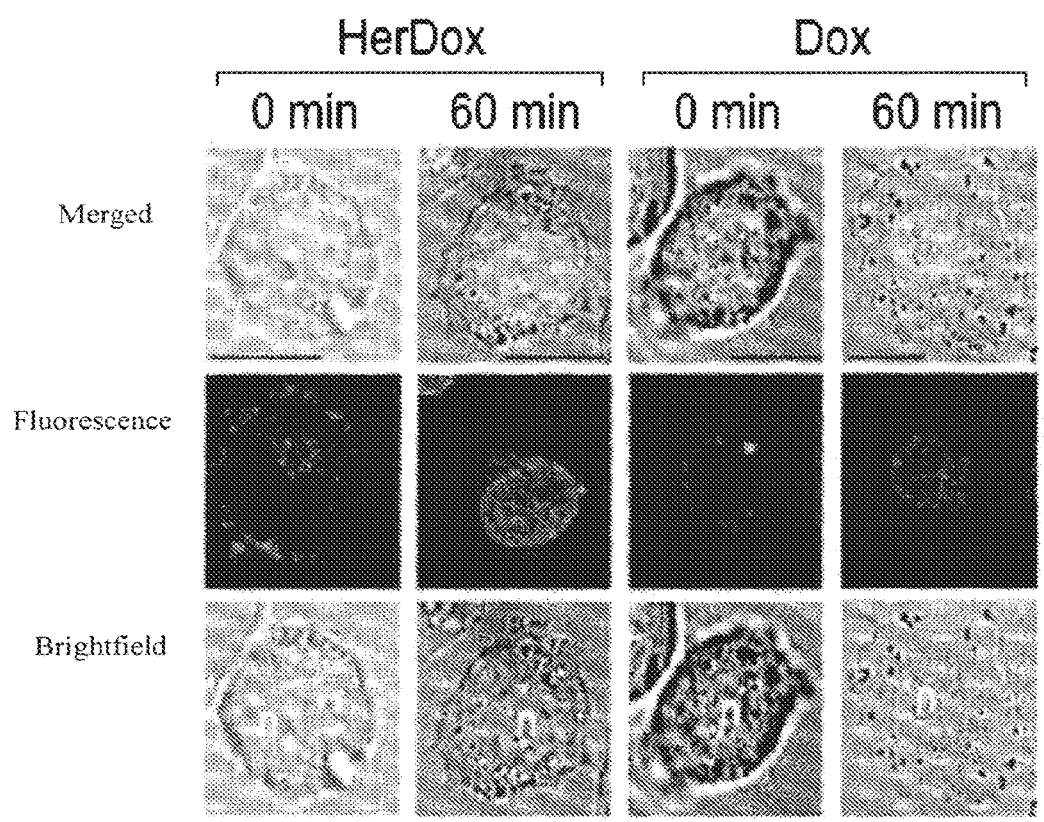
Figure 14:
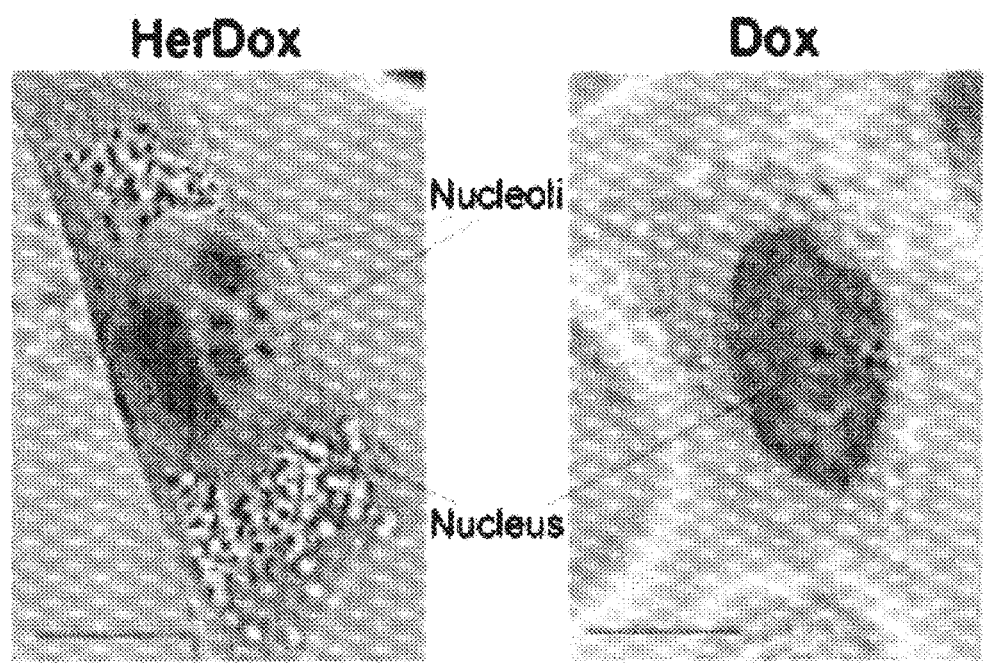

FIG. 14 (A) illustrates comparison of HerDox and Dox intracellular translocation and targets in live cells. MDA-MB-435 cells were incubated with HerDox or free Dox (0.5 μM) at 37° C. Live (unfixed) cells were imaged by brightfield and fluorescence microscopy.

FIG. 14 (B) illustrates comparison of HerDox and Dox intracellular translocation and targets in live cells. MDA-MB-435 cells were incubated with HerDox or free Dox (0.5 μM) at 37° C. Live (unfixed) cells were imaged by DIC and confocal fluorescence microscopy.

Figure 15:
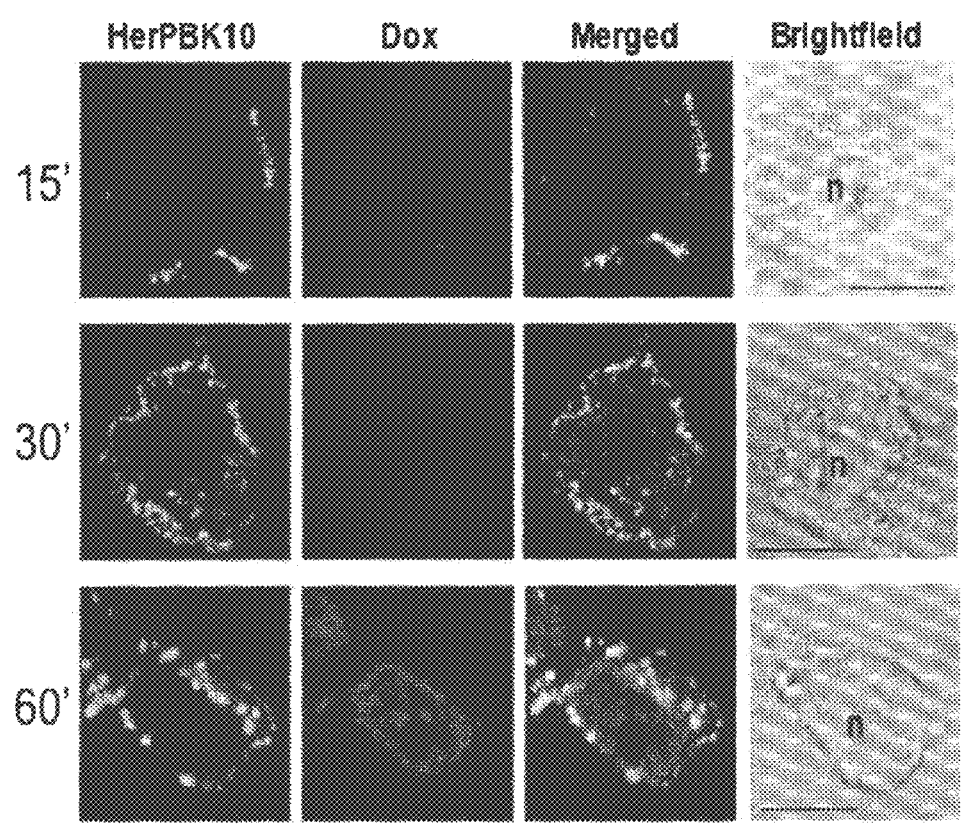

FIG. 15 illustrates HerDox trafficking in breast cancer cells. Cells incubated with HerDox at 37° C. were fixed at the indicated time points and processed for immunofluorescence using an antibody against HerPBK10. Images were captured using confocal microscopy under fluorescence and brightfield. n, nucleus; Bar, ~8 microns.

Figure 16:
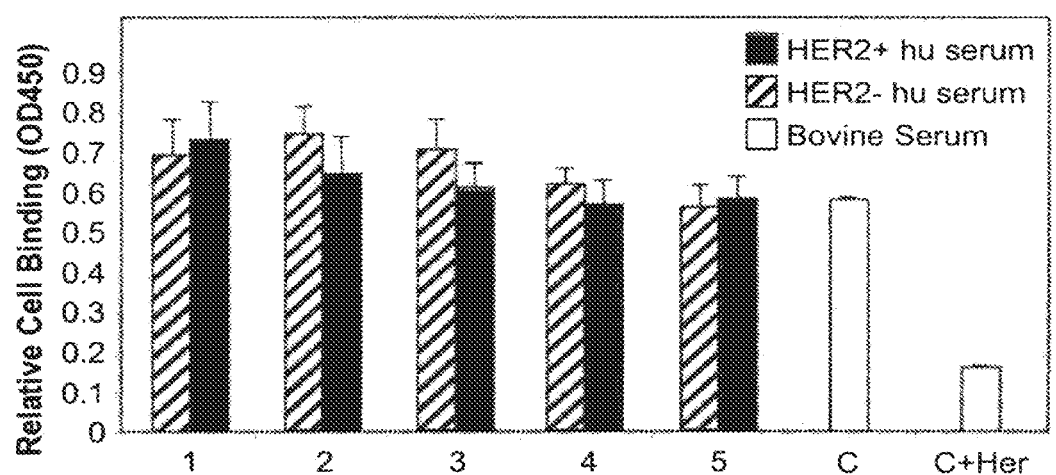

FIG. 16 illustrates HerPBK10 binding to MDA-MB-435 cells in human serum from HER2+ or HER2− breast cancer patients. Cells were treated with HerPBK10 (1.2 μg/well) in media containing human serum from each of 5 HER2+ breast cancer patients or age matched HER2− controls, both obtained pre-chemotherapy treatment. Cells were processed for ELISA using an antibody directed at HerPBK10. Control (C) wells receiving HerPBK10 in media containing bovine serum without or with 100× molar excess competitive ligand inhibitor (+Her) are indicated by open bars. Patient sera were provided by the WCRI tissue bank at Cedars-Sinai Medical Center. N=3 wells per treatment.

Figure 17:
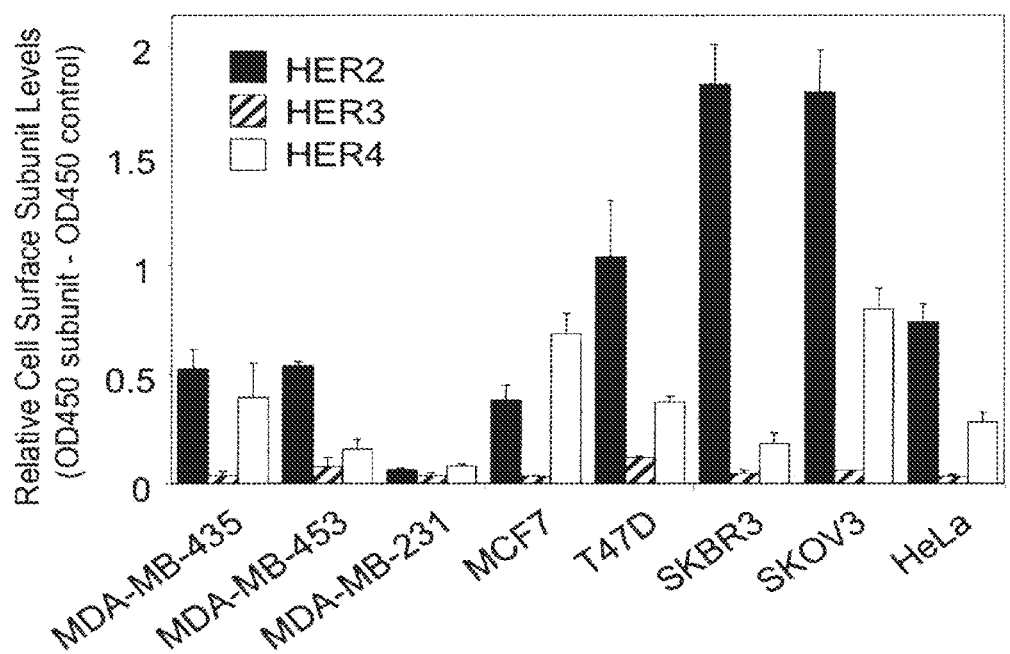
Figure 17:
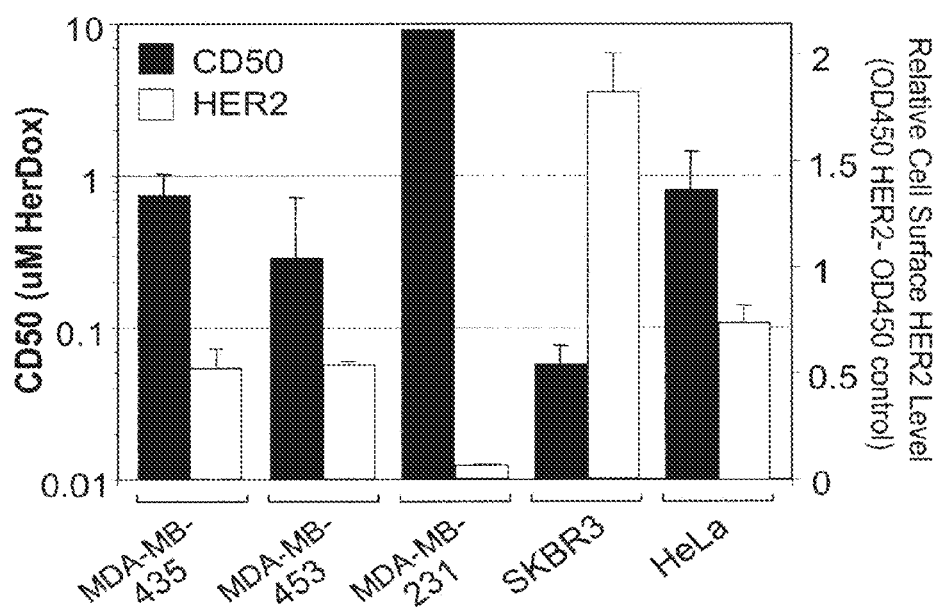

FIG. 17 (A) illustrates relative cell surface HER subunit levels and cytotoxicity on cell types. Cells were incubated with anti-HER subunit antibodies followed by HRP-conjugated secondary antibodies using standard procedures. Relative cell numbers were measured by crystal violet staining and quantified by measuring crystal violet absorbance at 590 nm. Relative subunit levels are reported as the ELISA signal of each cell population normalized by the relative cell number, or Abs 450 nm/590 nm. FIG. 17 (A) depicts a graph of relative cell surface HER subunit levels as measured by ELISA.

FIG. 17 (B) depicts toxicity to cells displaying differential HER2. Cytotoxicities from a range of HerDox doses were assessed on each cell line by metabolic assay and confirmed by crystal violet stain. LD50 values shown in log scale were determined by non-linear regression analyses of HerDox dose curves using a scientific graphing program and confirmed using a calculator. The relative HER2 level of each cell line is shown next to each LD50 value.

Figure 18:
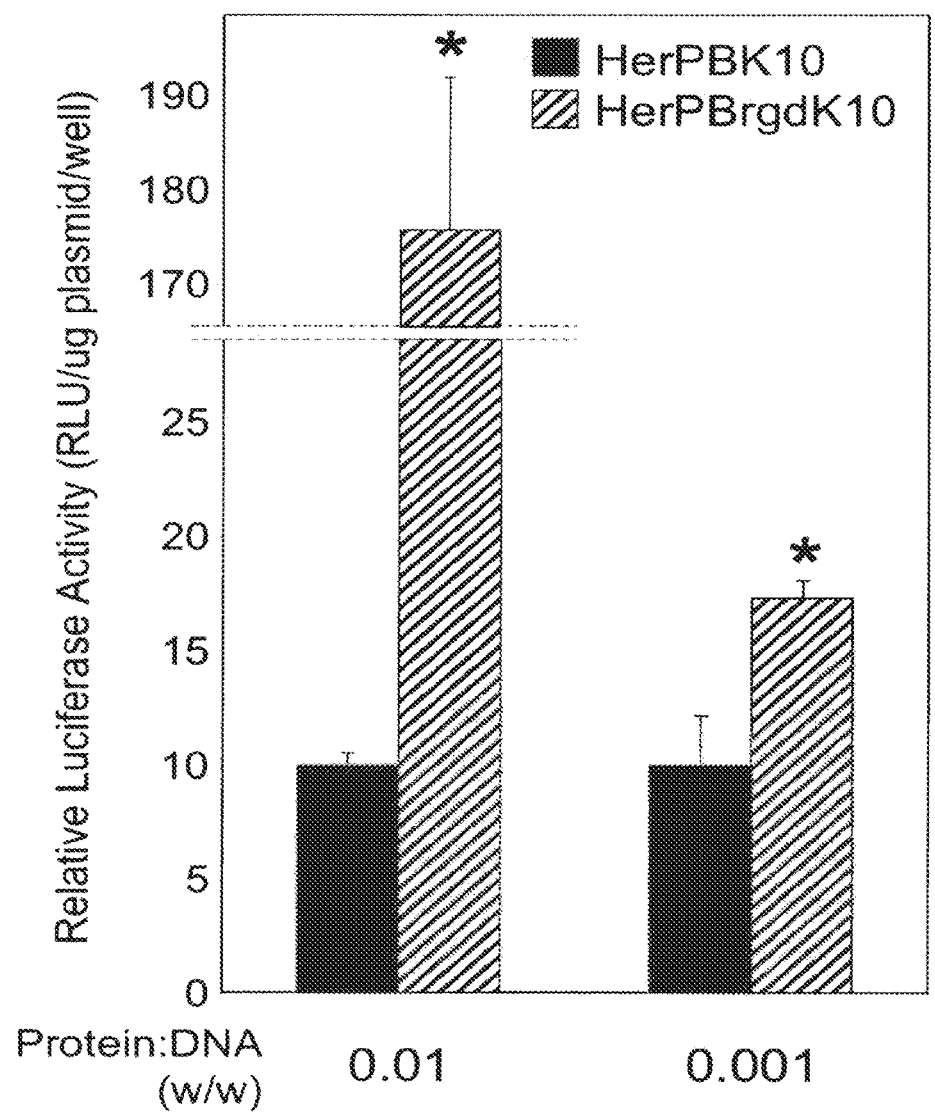

FIG. 18 illustrates optimization of HerPBK10. The delivery capacity of the modified protein, HerPBrgdK10 was tested in the context of a nonviral gene transfer complex, and delivery efficiency assessed by transgene (luciferase) expression in MDA-MB-453 human breast cancer cells. *=P<0.005 compared to equivalent concentration of HerPBK10, as determined by 2-tailed T test. The figure demonstrates that the invention is in no way limited to HerPBK10 as various mutations may be introduced that will improve targeting, receptor binding, cell entry and/or intracellular trafficking of the protein.

Figure 19:
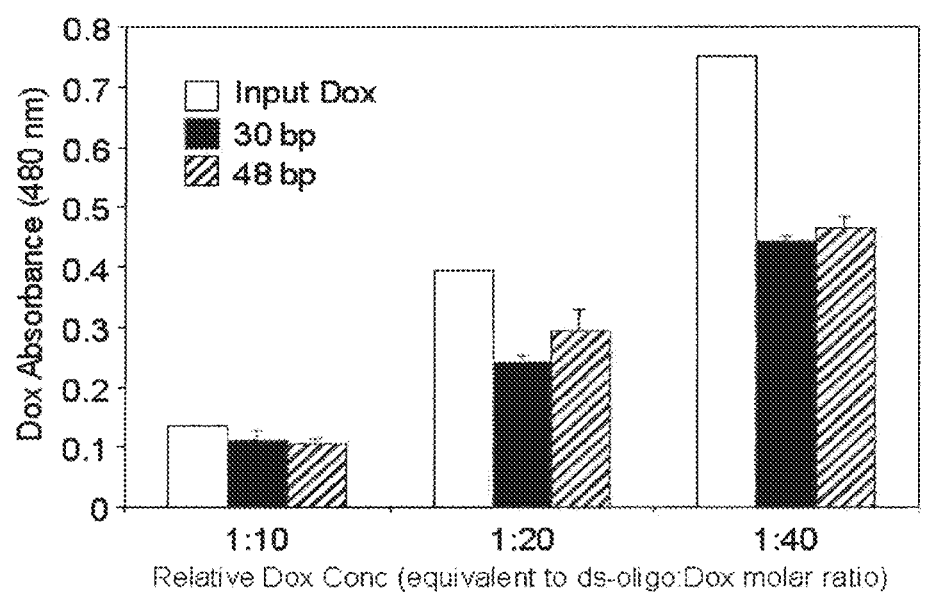

FIG. 19 illustrates a graph demonstrating that DS-oligo length does not affect Dox incorporation into the targeted complex. The graph demonstrates that there is no appreciable difference in Dox incorporation using either 30 or 48 base pair duplexes.

Figure 20:
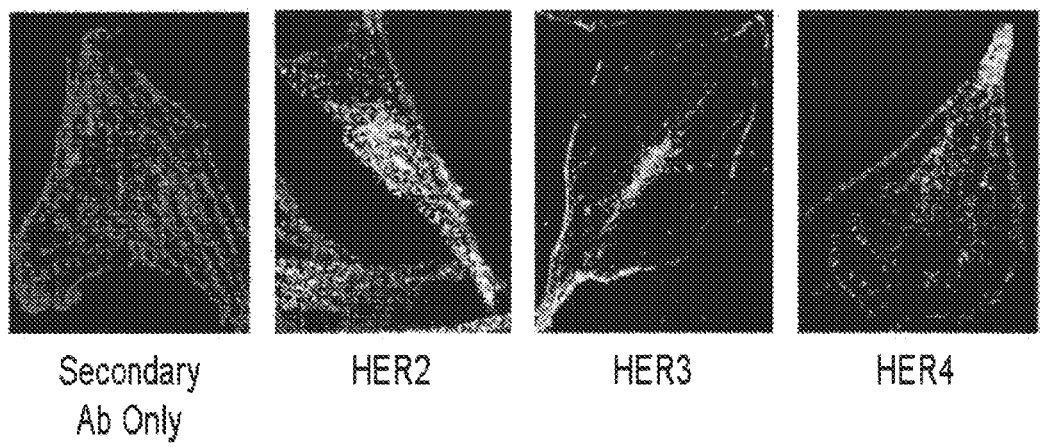
Figure 20:
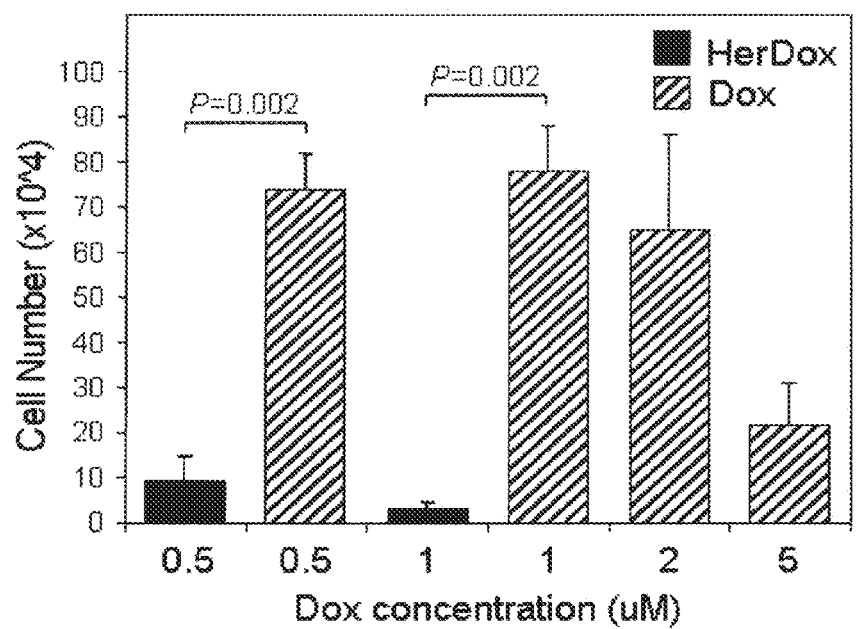

FIG. 20 (A) illustrates HerDox is toxic to glioma cells. FIG. 20 (A) depicts HER immunofluorescence on U251 human glioma cells. Images were captured using laser scanning fluorescence confocal microscopy.

FIG. 20 (B) depicts a graph of HerDox versus Dox toxicity to U251 cells. Significant differences were determined by 2-tailed tests.

Figure 21:
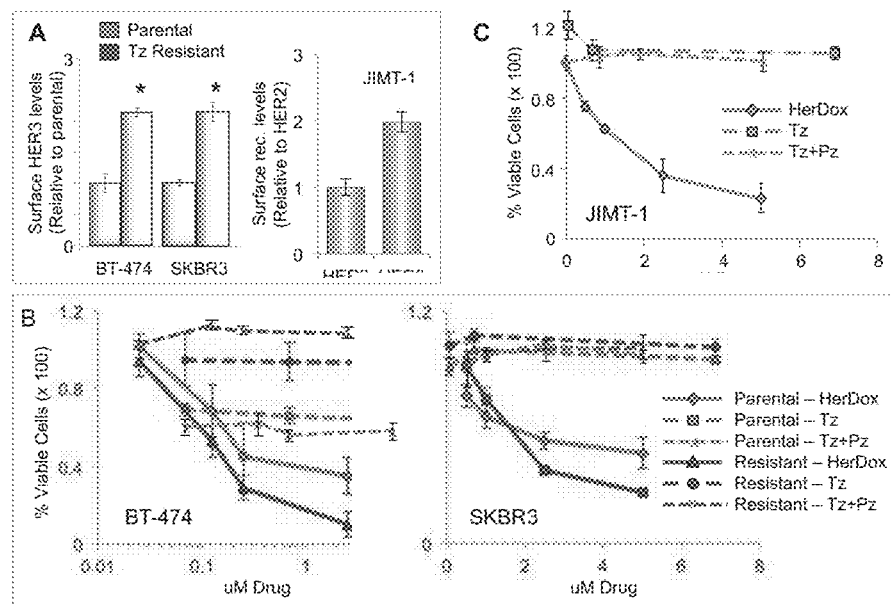

FIG. 21 depicts graph that show the results of the administration of HerDox on various cells. (A) illustrates that resistance enhances HerDox toxicity. (A) Relative surface levels of HER3 (and HER2) on parental and trastuzumab resistant breast cancer cell lines, detected by ELISA without membrane permeabilization. N=3. *=p<0.05 compared to parental. (B) illustrates tumor cell killing by HerDox (by 48-72 hours after treatment) in comparison to trastuzumab alone, pertuzumab alone, and trastuzumab-pertuzumab combination treatment. N=3.

Figure 22:
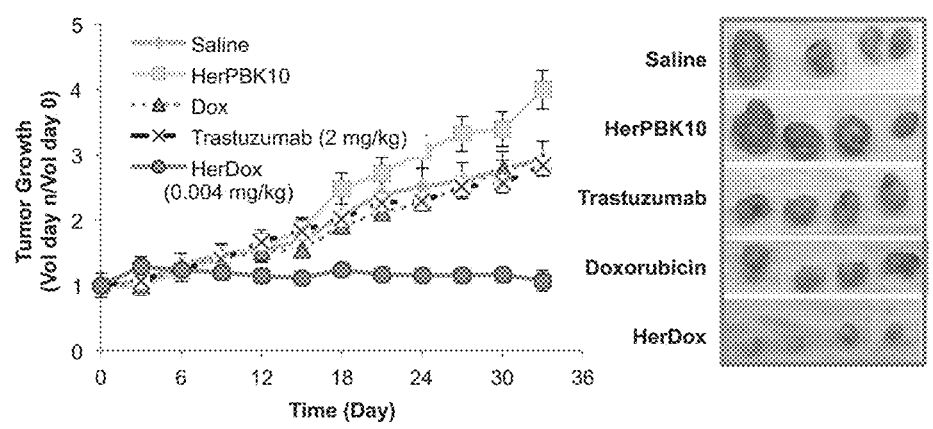

FIG. 22 is a graph showing HerDox kills trastuzumab-resistant tumors in vivo. Female nude mice bearing JIMT-1 tumors received indicated reagents at indicated doses by IV (tail vein) injection when tumors reached ~100 mm³ (twice-weekly injections for 4-6 weeks). Tumor volumes were measured by calipers. Day 0 corresponds to first day of treatment. N=10 tumors per treatment.

Figure 23:
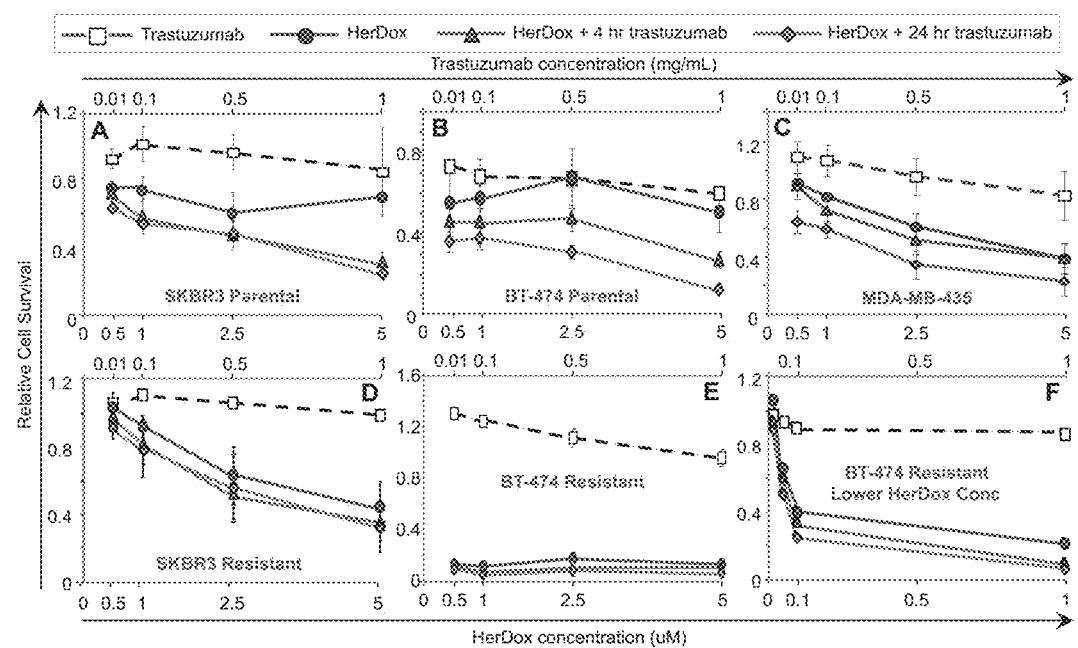

FIG. 23 are graphs showing that trastuzumab pre-treatment augments HerDox toxicity. Parental or non-resistant cells (A-C) and trastuzumab-resistant cells (D-F) were treated with trastuzumab at indicated concentrations (see upper X-axes) 4 and 24 hours before HerDox treatment and assayed for survival at 48-72 h after treatment. N=3.

Figure 24:
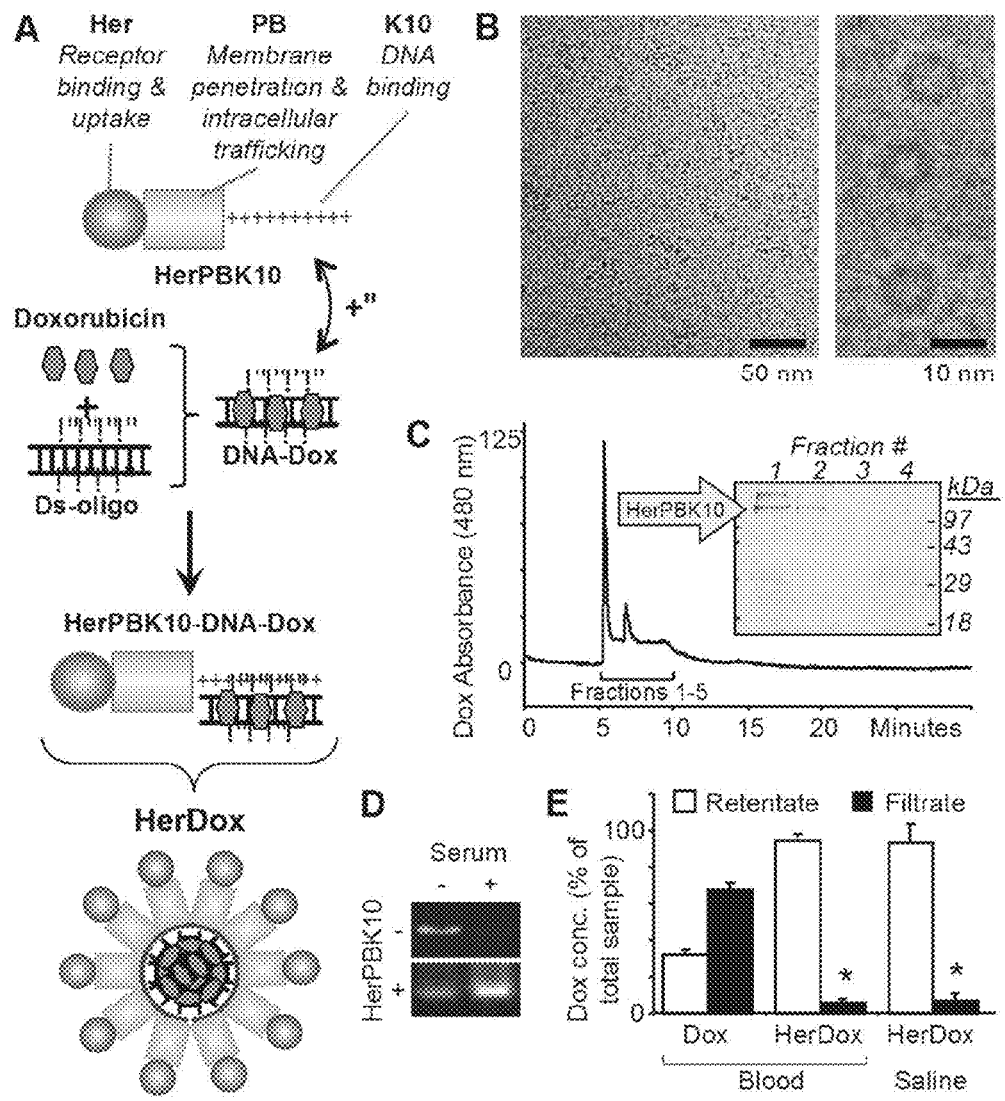

FIG. 24 shows graphs and images related to the formation of HerDox. (A) depicts a graphic of HerDox formed by non-covalent, serum-stable self-assembly, showing Her-PBK10 with functional domains delineated, and electrophilic binding with Dox-intercalated ds-oligo. (B) depicts a CryoEM image of HerDox particles. (C) is a HPLC chromatogram of HerDox showing elution profile of Dox absorbance. (C) further shows the SDS-PAGE of the HPCE collected fractions. (D) illustrates the protection of ds-oligo from serum nuclease digestion by HerPBK10. The ds-oligo was incubated for 20 min in 100% mouse serum (Abcam, Cambridge, Mass., USA) before PAGE and EtBr staining to visualize the DNA. (E) illustrates that HerDox remains stable in blood. Dox or HerDox were incubated for one hour in mouse blood at 37° C. followed by ultrafiltration to separate any released Dox (Filtrate) from the complex (Retentate). N=3. *, p<0.05, compared to respective retentates.

Figure 25:
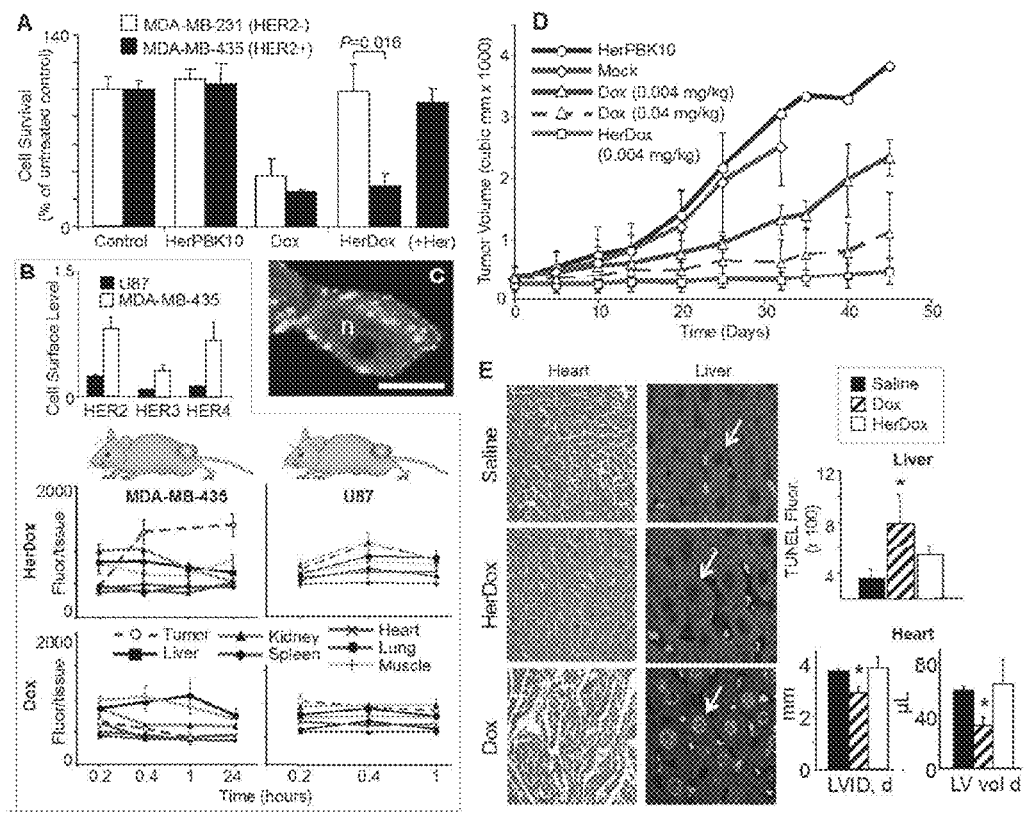

FIG. 25 shows that HerDox mediates tumor-targeted delivery in vitro and in vivo. (A) compares cytotoxicity to HER2+ (MDA-MB-435) and HER2− (MDA-MB-231) cells in separate cultures treated with HerDox or Dox (0.5 μM final Dox concentration). Relative cell survival (as % of untreated cells) on day 3 of treatment. (+Her), pre-incubation of MDA-MB-435 cells with receptor-blocking ligand (recombinant heregulin) before receiving HerDox. N=3. (B) compares biodistributions of HerDox and Dox in mice with tumors expressing differential HER2-3. Tissues were harvested from independently injected mice euthanized at indicated time points after injection and fluorescence intensity/tissue acquired using a multimode imager. (C) illustrates HerPBK10 and Dox localities at one hour after HerDox uptake in MDA-MB-435 cells. n, nucleus. Bar, about 4 μm. (D) compares HerDox and Dox on tumor growth (N=8-10 tumors per treatment). Day 0=3 days before tail vein injections (mice received daily injections for 7 days). Control (saline-injected) mice were euthanized early due to tumor ulceration, in compliance with IACUC policy. (E) compares HerDox and Dox on off-target tissue. Day 0=3 days before tail vein injections (mice received daily injections for 7 days). Control (saline-injected) mice were euthanized early due to tumor ulceration, in compliance with IACUC policy. Micrographs (20× magnification) in (E) also show representative H&E stained specimens of myocardia and immunofluorescent specimens of livers from treated mice. Green fluorescence in nuclei indicates apoptosis (positive TUNEL stain). Upper graph, quantification of TUNEL stains; Lower graphs, echocardiography measurements at 25 days after injections. *, P<0.05, compared to saline (Mock).

Figure 26:
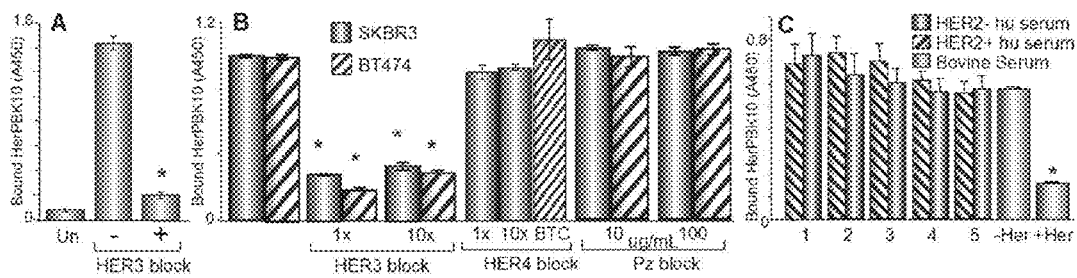

FIG. 26 shows the results of various ELISA assays. (A) shows ELISA of HerPBK10 binding to immobilized HER3 (human ErbB3 extracellular domain; Prospec)−/+pre-incubation with soluble HER3 peptide as a competitive inhibitor (HER3 block). Un, no HerPBK10. (B) shows ELISA of HerPBK10 binding to HER2+ cells−/+pre-incubation with: a 1× and 10× molar ratio of soluble HER3 peptide, soluble HER4 peptide (ERBB4 peptide, Abnova), betacellulin (10 μg/mL), or pertuzumab (Pz) as competitive inhibitors. Her-PBK10 binding to HER3 is not inhibited by patient serum.

Figure 27:
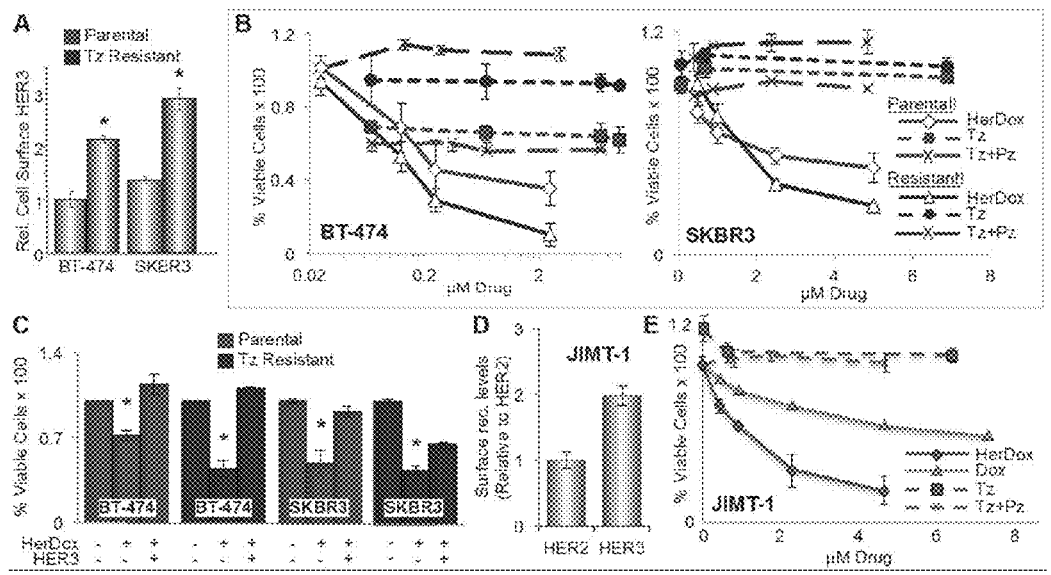

FIG. 27 shows the effect of resistance to HerDox toxicity. (A)_-illustrates that resistance enhances HerDox toxicity.

(A) also shows relative surface levels of HER3 (and HER2) on parental and Tz-resistant breast cancer cell lines, detected by ELISA without membrane permeabilization. N=3. *, p<0.05 compared to parental. (B)_illustrates that resistance enhances HerDox toxicity. (B) also shows tumor cell killing by HerDox (48-72 h after treatment) in comparison to Tz, Pz, Tz+Pz, and Dox alone. N=3. (C) illustrates contribution of HER3 to targeted toxicity. Parental and resistant cell lines were treated with HerDox−/+HER3 blocking peptide (ErbB3 human; Prospec), and tested for cell survival 48 hours later. Specifically, HerDox was adsorbed with HER3 peptide at equimolar ratio HER3:HerPBK10 in cold PBS for one hour before adding to cells at a final HerDox concentration of 0.1 µM (JIMT-1, naturally resistant to trastuzumab treatment), 0.125 µM (BT-474), or 1 µM (SKBR3). Treatments were compared to mock (saline)-treatment. N=3. *, p<0.05 compared to mock (D) illustrates relative surface levels of HER3 (and HER2) on parental and Tz-resistant breast cancer cell lines, detected by ELISA without membrane permeabilization. N=3. *, p<0.05 compared to parental. (E) illustrates tumor cell killing by HerDox (48-72 h after treatment) in comparison to Tz, Pz, Tz+Pz, and Dox alone. N=3.

Figure 28:
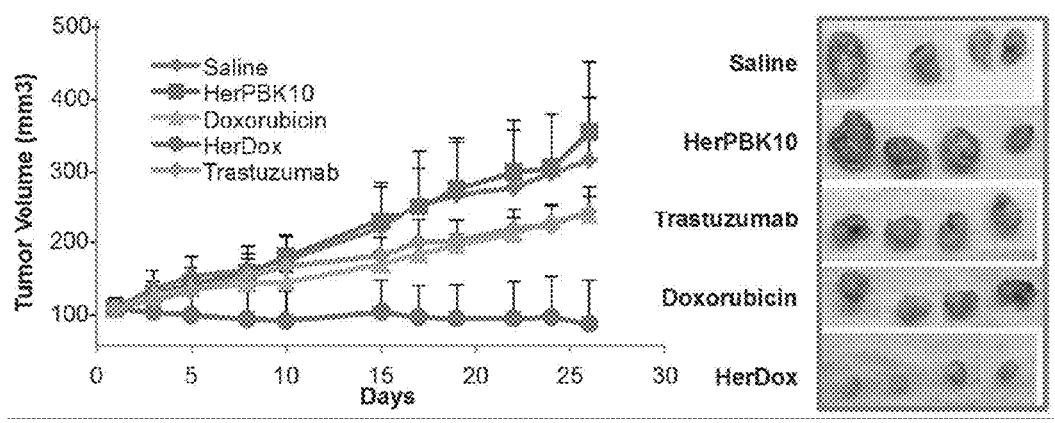

FIG. 28 demonstrates that HerDox eliminates trastuzumab-resistant tumor growth in vivo. Female nude mice bearing JIMT-1 tumors received indicated reagents at indicated doses through intravenous (tail vein) injection when tumors reached ~100 mm³ (twice-weekly injections for 4 weeks). Tumor volumes were measured by calipers. Day 0 corresponds to first day of treatment. N=10 tumors per treatment.

Figure 29:
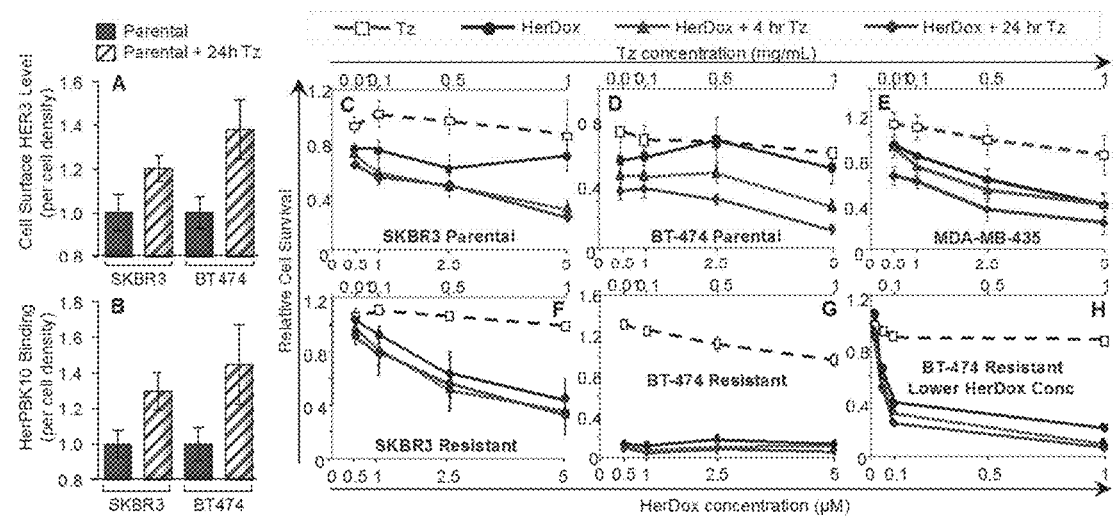

FIG. 29 shows the results of various pre-treatment studies. (A) illustrates that Trastuzumab pre-treatment augments HerDox toxicity. (A) also shows induced elevation of HER3 by Tz and enhanced binding by HerPBK10. Parental cell lines were pre-treated with 0.5 mg/mL Tz for 24 hours before testing these cells for surface HER3 levels. (B) illustrates that Trastuzumab pre-treatment augments HerDox toxicity. (B) also shows induced elevation of HER3 by Tz and enhanced binding by HerPBK10. Parental cell lines were pre-treated with 0.5 mg/mL Tz for 24 hours before testing these cells for HerPBK10 binding. (C) shows that Trastuzumab pre-treatment augments HerDox toxicity. SKBR3 Parental cells were treated with Tz at indicated concentrations (see upper X-axes) 4 and 24 hours before HerDox treatment and assayed for survival at 48-72 h after treatment. N=3. (D) shows that Trastuzumab pre-treatment augments HerDox toxicity. SK-474 Parental cells were treated with Tz at indicated concentrations (see upper X-axes) 4 and 24 hours before HerDox treatment and assayed for survival at 48-72 h after treatment. N=3. (E) shows that Trastuzumab pre-treatment augments HerDox toxicity. MDA-MB-435 non-resistant cells were treated with Tz at indicated concentrations (see upper X-axes) 4 and 24 hours before HerDox treatment and assayed for survival at 48-72 h after treatment. N=3. (F) shows that Trastuzumab pre-treatment augments HerDox toxicity. Tz-resistant cells were treated with Tz at indicated concentrations (see upper X-axes) 4 and 24 hours before HerDox treatment and assayed for survival at 48-72 h after treatment. N=3. (G) shows that Trastuzumab pre-treatment augments HerDox toxicity. Tz-resistant cells were treated with Tz at indicated concentrations (see upper X-axes) 4 and 24 hours before HerDox treatment and assayed for survival at 48-72 h after treatment. N=3. (h) shows that Trastuzumab pre-treatment augments HerDox toxicity. Tz-resistant cells were treated with Tz at indicated concentrations (see upper X-axes) 4 and 24 hours before HerDox treatment and assayed for survival at 48-72 h after treatment. N=3.

Figure 30:
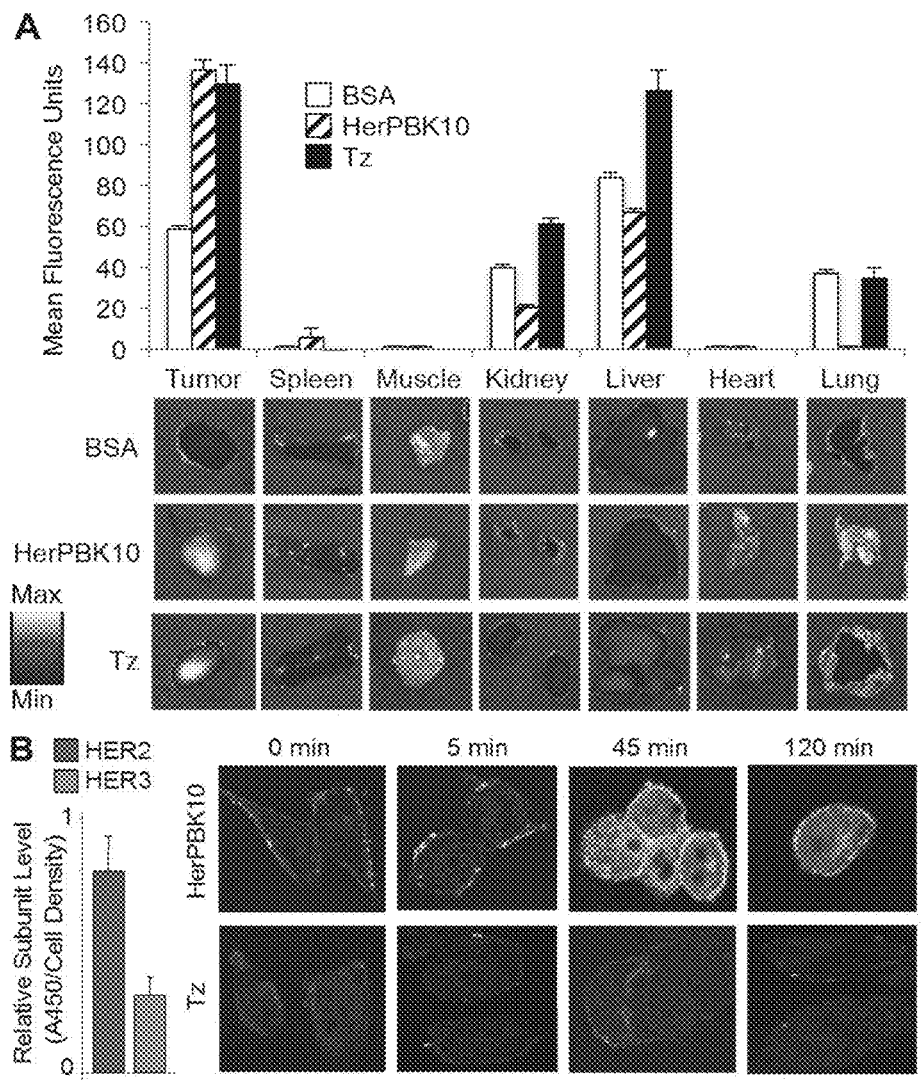

FIG. 30 shows the results of two studies. (A) compares biodistribution and intracellular trafficking of HerPBK10 and Tz. (A) also shows xenogen imaging and fluorescence quantification of biodistribution by labeled HerPBK10, Tz, and BSA. (B) shows fluorescence confocal micrographs of MDA-MB-435 cells at different time points after cell surface binding by HerPBK10 (green) and Tz (green). Graph shows relative cell surface levels of HER2 (left bar) and HER3 (right bar), quantified by cell surface ELISA and normalized by cell density.

Figure 31:
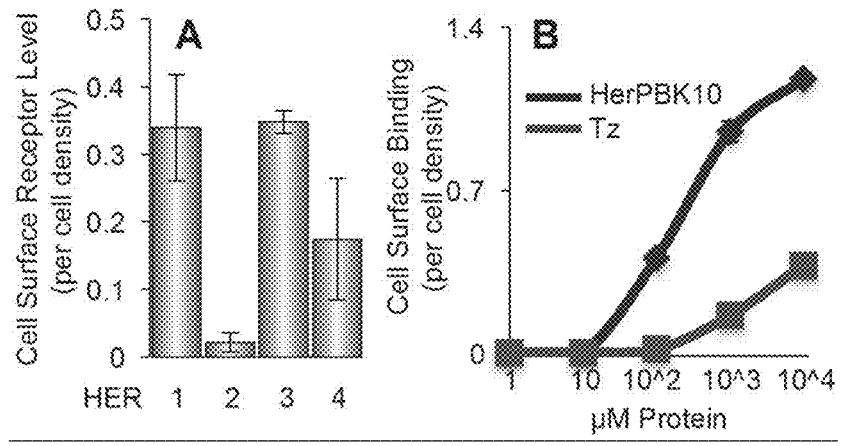

FIG. 31 shows the results of two studies. (A) shows binding to primary human tumor cells. Primary tumor cells obtained from a surgical specimen of a HER2+ patient were probed for cell surface receptor levels. (B) shows binding to primary human tumor cells. Primary tumor cells obtained from a surgical specimen of a HER2+ patient were probed for HerPBK10 binding.

Figure 32:
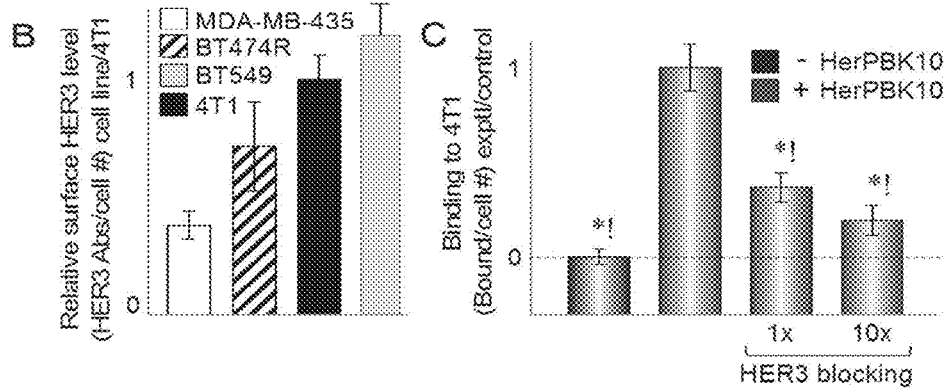

FIG. 32 shows the results of several studies. (A) is an amino acid sequence alignment of domains I-II (heregulin-binding domain) of human (SEQ ID NO:13) and mouse HER3 (SEQ ID NO:14). (B) compares relative HER3 levels on different cell lines, detected by ELISA (without permeabilization) using an anti-HER3 antibody that cross-reacts with both human and mouse HER3 (1B2E; Cell Signaling Technologies). (C) illustrates binding of HerPBK10 to 4T1 mouse mammary tumor cells. N=3. *, p<0.05 compared to HerPBK10 alone.

Figure 33:
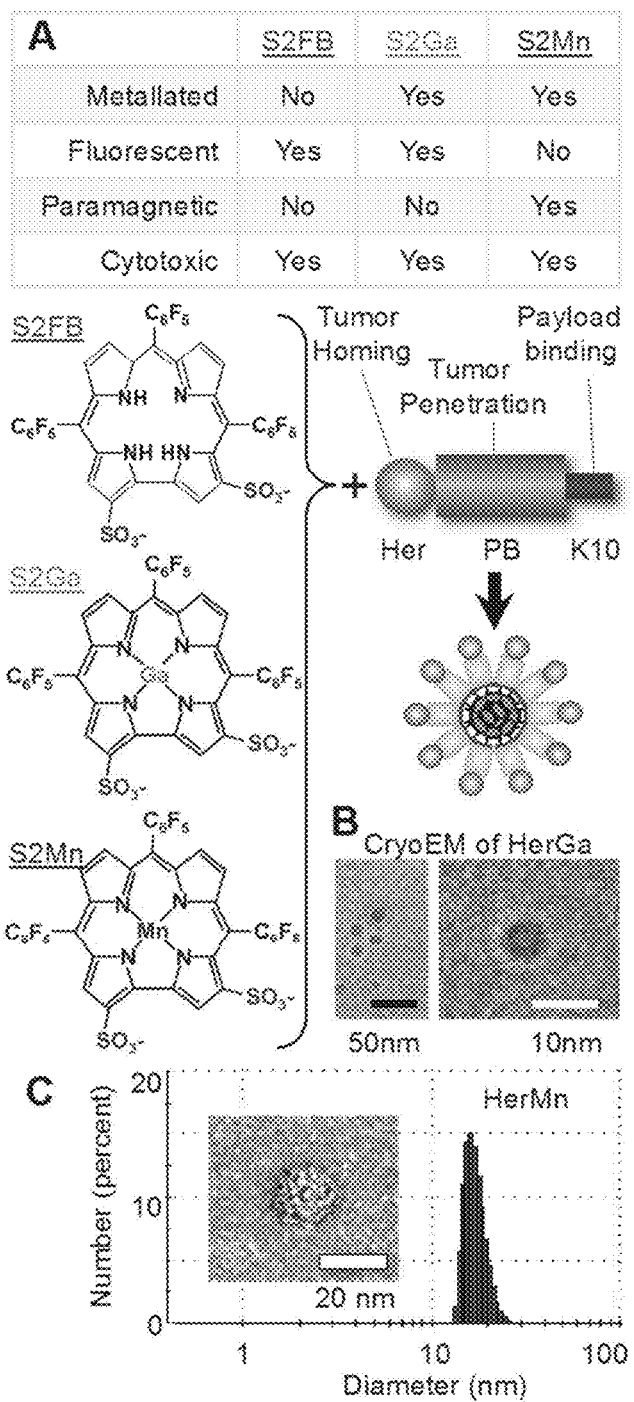

FIG. 33 illustrates the formation of certain corroles. (A) shows the chemical structures of metallated (S2Ga, S2MN) and non-metallated (S2FB) sulfonated corroles, and schematic of non-covalent assembly with HerPBK10 to form round particles, designated HerFB, HerGa, and HerMn respectively. Table summarizes salient features of the three corroles. (B) shows the CryoEM image of HerGa. (C) shows dynamic light scattering measurement of HerMn in solution. Inset shows TEM of HerMn particle.

Figure 34:
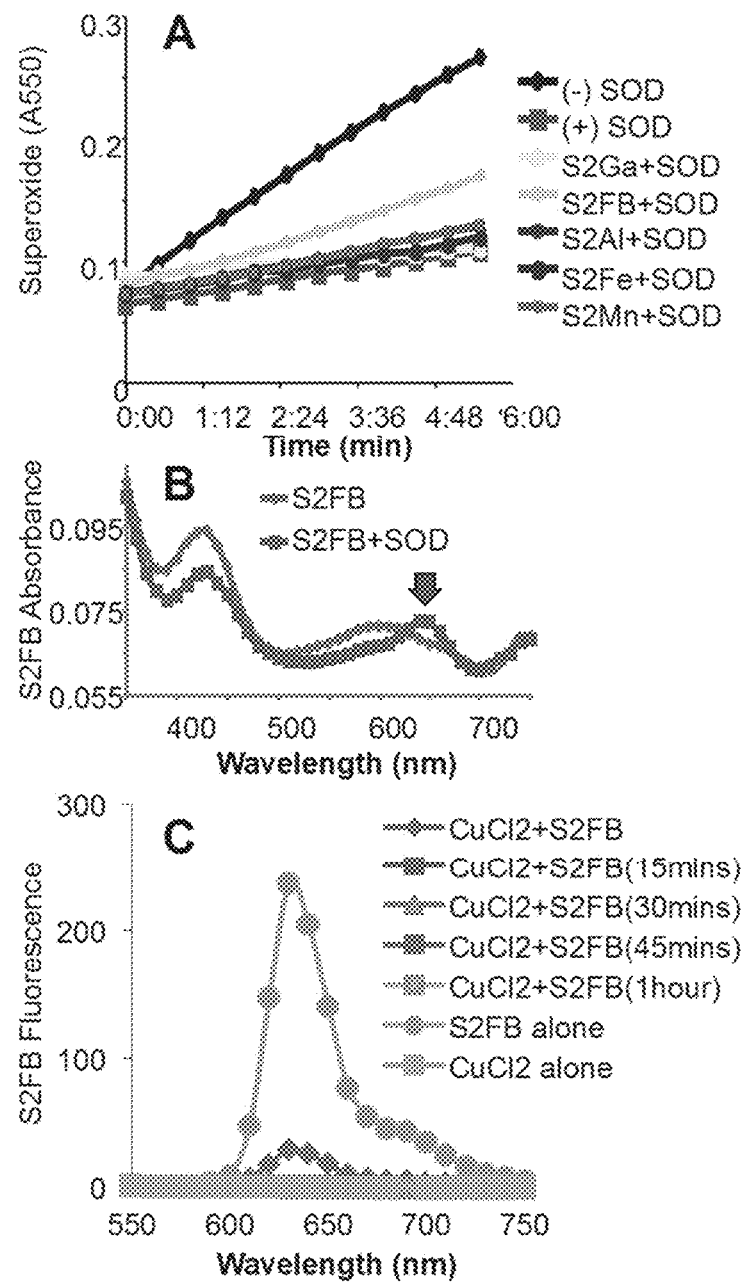

FIG. 34 shows the results of several studies. (A) shows that S2FB but not the metallated corroles inhibit SOD1. An in vitro assay measuring superoxide production from XOD−/+SOD. Only S2FB (1 µM) affects SOD activity, reducing it by about one-third. (B) shows that S2FB absorbance peak is shifted (arrow) by incubation with SOD. (C) shows that $CuCl_2$ quenches S2FB fluorescence.

Figure 35:
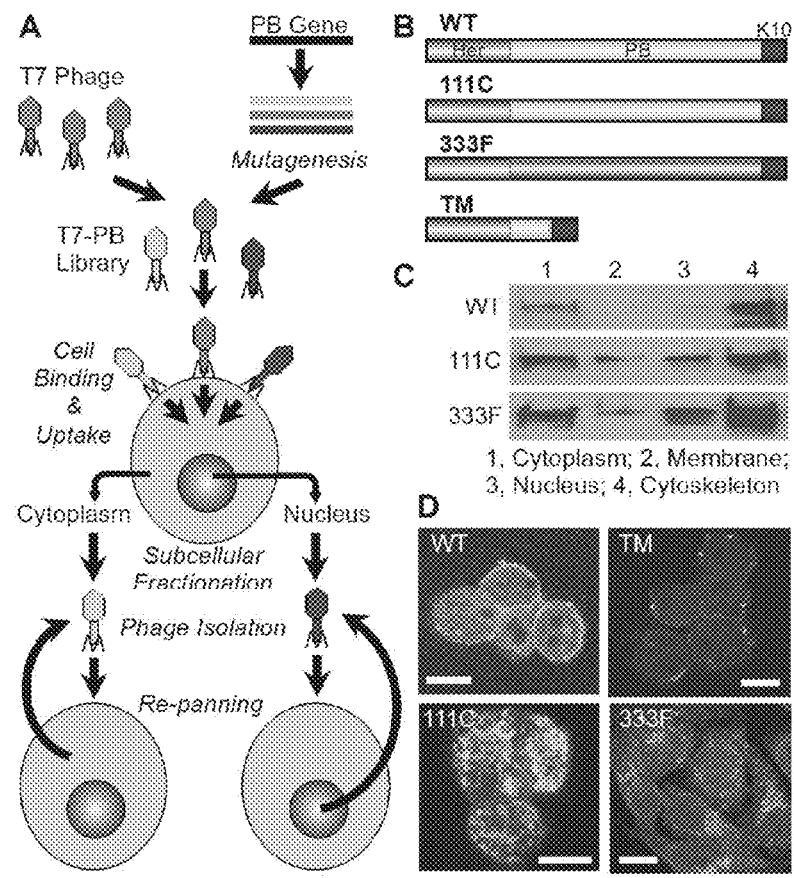

FIG. 35 shows the results of several studies. (A) illustrates a scheme summarizing random mutagenesis and biopanning of mutant penton base library. (B)_illustrates schematic of full-length and truncated clones isolated from biopanning, in alignment with wt HerPBK10. (C) shows immunoblots of subcellular fractions (20 µg/lane), detected using antibody against N-terminal histidine tag. (D) shows immunofluorescence of MDA-MB-435 cells at 30 min uptake of indicated recombinant protein (10 µg/well, 12 well dish). Bar, ~10 µm.

Figure 36:
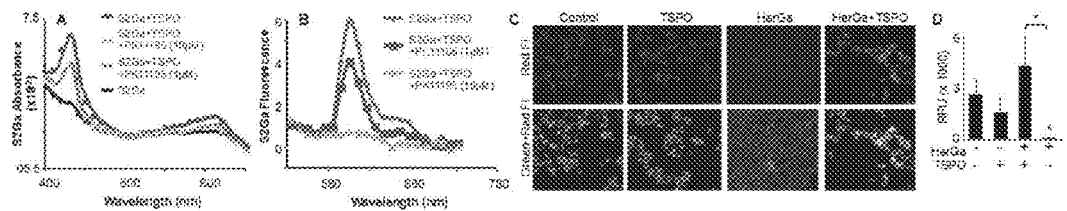
Figure 37:
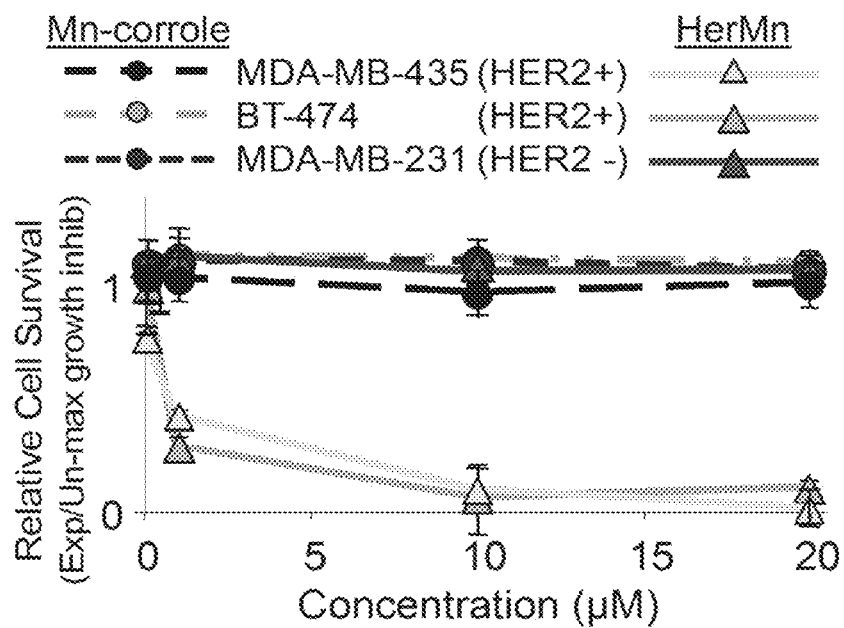

FIG. 36 shows the results of several studies. (A) illustrates that S2Ga interacts with TSPO. (A) also shows that soluble recombinant TSPO protein was incubated with S2Ga at equivalent molar concentrations (1 µM) for ~20 min at room temperature followed by ultrafiltration to remove free, unbound S2Ga. Retentates were evaluated for the presence of protein-bound corrole by measuring the absorbance and fluorescence spectra. Where indicated, PK11195 was used as a competitive inhibitor for the porphyrin binding site on TSPO. (B) further illustrates that S2Ga interacts with TSPO. (B) also shows that soluble recombinant TSPO protein was incubated with S2Ga at equivalent molar concentrations (1 µM) for ~20 min at room temperature followed by ultrafiltration to remove free, unbound S2Ga. Retentates were evaluated for the presence of protein-bound corrole by measuring the absorbance and fluorescence spectra. Where indicated, PK11195 was used as a competitive inhibitor for the porphyrin binding site on TSPO. (C) shows evidence of HerGa interaction with TSPO in situ. MDA-MB-435 cells were transfected with a plasmid expressing exogenous TSPO 24 hours before cells were treated with HerGa and examined for HerGa-mediated mitochondrial disruption, evidenced by reduced red fluorescent dye accumulation in mitochondria and accumulated green fluorescence in the cytoplasm. (D) shows quantification of red fluorescence seen in (C). *, $p<0.05$ FIG. 37 shows HerMn toxicity on human HER2+ and HER2− tumor cells. Each cell line received the indicated concentration of HerMn or S2Mn and was assessed for survival 24 hours later via crystal violet (CV) stain. N=3 per conc, from 3 separate experiments.

Figure 38:
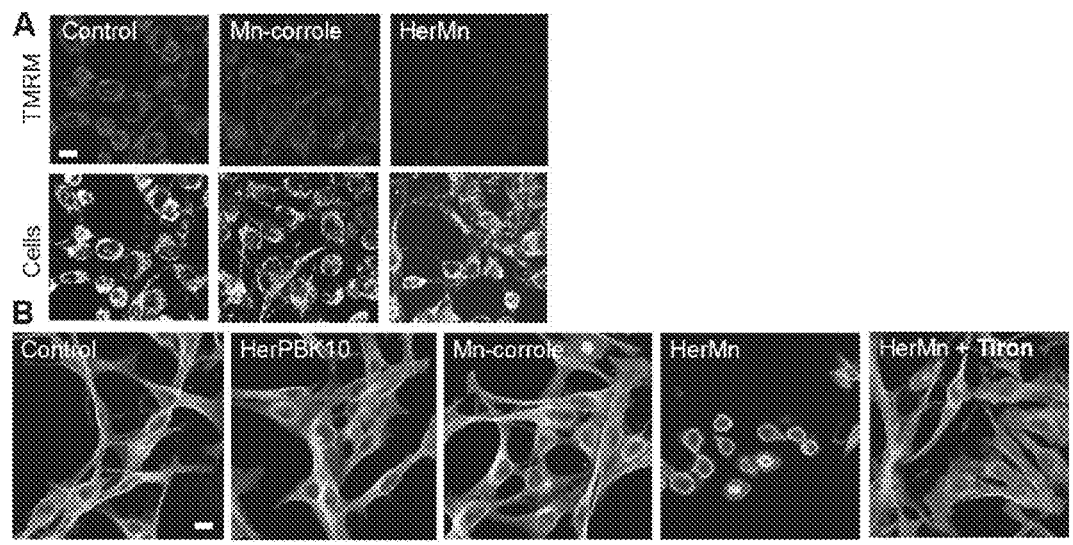

FIG. 38 shows the results of several studies. (A) shows the mechanism of HerMn cytotoxicity. Confocal fluorescence images show effect of HerMn on MDA-MB-435 cells. Scale bar=10 μm. (A) also shows reduction of mitochondrial membrane potential in cells receiving 10 μM S2Mn or HerMn, followed by TMRM (30 nM) in HBSS 24 hours later. Control, PBS-treated. (B) shows the mechanism of HerMn cytotoxicity. Confocal fluorescence images show effect of HerMn on MDA-MB-435 cells. Scale bar=10 μm. (B) also shows superoxide-mediated collapse of actin (red) and tubulin (green) by HerMn (5 μM) after 24 hour incubation on cells. S2Mn (5 μM), HerPBK10 (at equivalent protein conc as HerMn) and PBS served as controls. Additional cells received Tiron (5 mM) for one hour before HerMn treatment.

Figure 39:
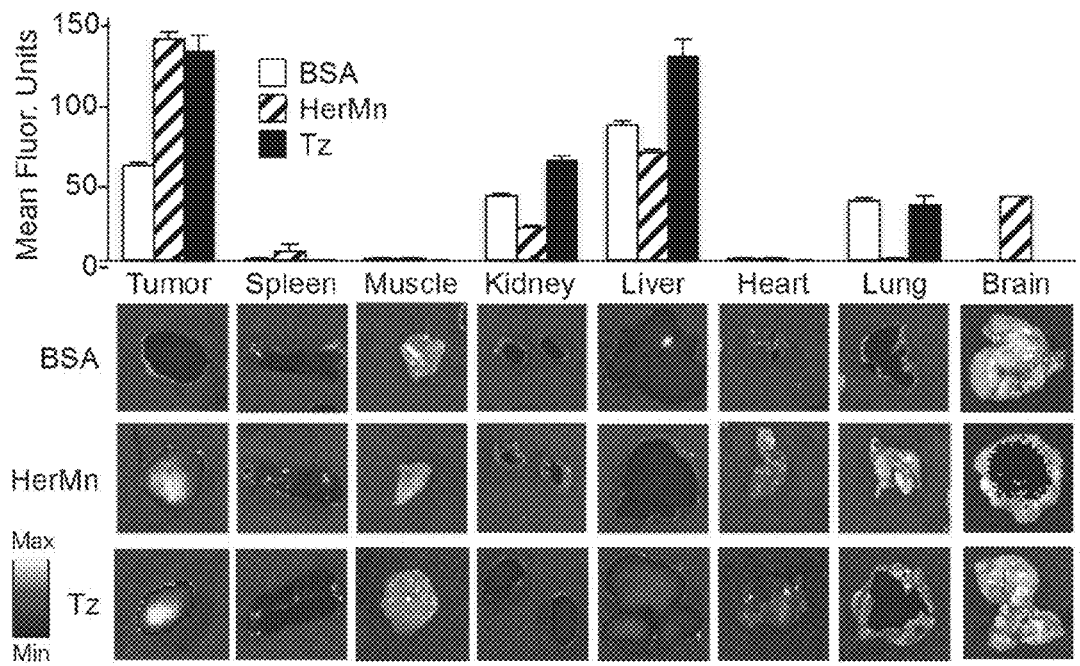

FIG. 39 shows bio-distribution in tumor-bearing mice. Xenogen imaging and quantification of Alexa680-labeled HerMn, Tz and BSA (12 nmol each) after tail vein injection. Graph, mean fluorescence−/+SEM.

Figure 40:
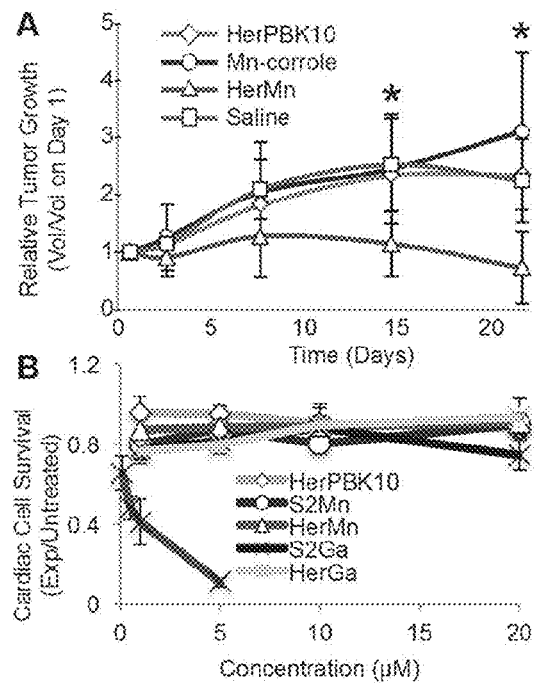

FIG. 40 shows the results of several studies. (A) is an illustration of therapeutic efficacy of HerMn. (A) shows HER2+ MDA-MB-435 tumor growth in female nude mice receiving daily intravenous injections (via tail vein) of HerMn or S2Mn (5 nmol corrole/injection) once/day for 6 consecutive days. Control groups received saline or HerPBK10 at equivalent concentration to HerMn. Treatments began at ~200 mm³ average tumor volume. Tumor volumes were measured before (day 1), during (day 3), and after (days 8, 15, and 22) injections of reagents. N=8-10 tumors/group. *$p<0.05$ (one-way ANOVA). (B) shows human CDC viability after 48 hour exposure to HerMn, S2Mn, HerPBK10, or doxorubicin (Dox). N=3 per conc, from 3 separate experiments.

Figure 41:
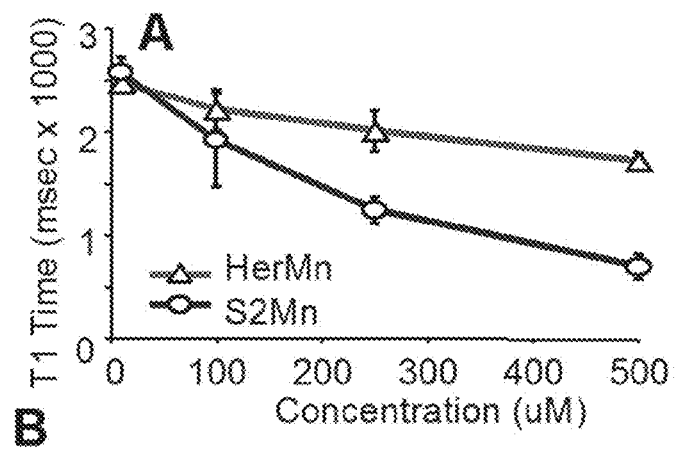
Figure 41:
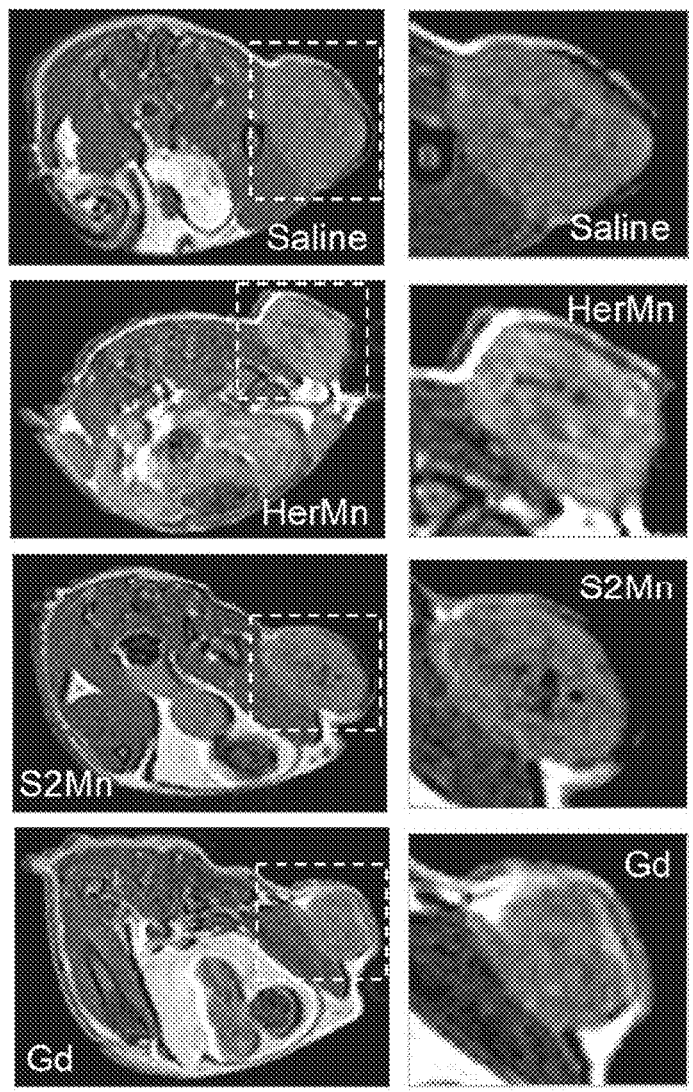

FIG. 41 shows the results of several studies. (A) illustrates that HerMn enhances MRI contrast. (A) also shows T1 relaxation shortening in solution. (B) illustrates that HerMn enhances MRI contrast in vivo. Images (left) show cross-sections of tumor-bearing mice after receiving daily systemic (IV) injections of HerMn or S2Mn (8 nmol per injection) for 8 days to allow for accumulation of signal or one injection of 0.1 mmol/kg gadolinium 10 min prior to imaging. Tumors are delineated by boxed regions, and enlarged (right).

Figure 42:
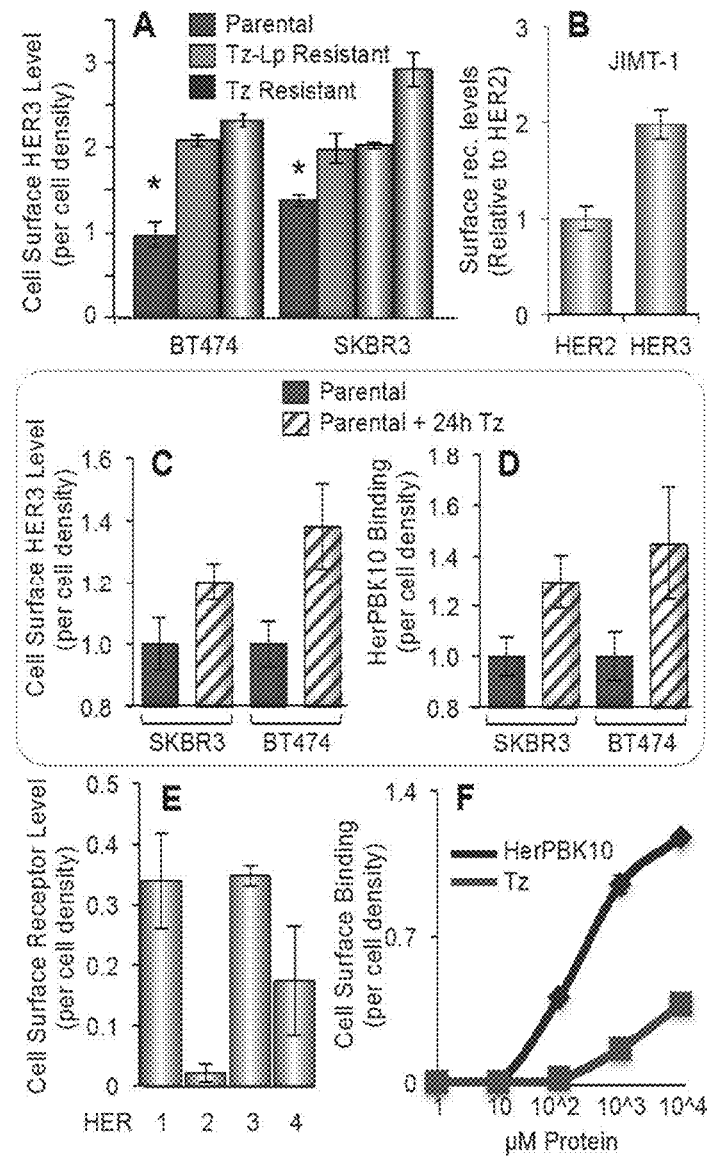

FIG. 42 shows the results of several studies. (A) shows relative surface levels of HER3 and HER2 on parental and Tz-resistant breast cancer cell lines, detected by ELISA without membrane permeabilization. N=3. *, $p<0.05$ compared to parental. (B) shows relative surface levels of HER3 and HER2 on JIMT-1 breast cancer cell lines, detected by ELISA without membrane permeabilization. N=3. *, $p<0.05$ compared to parental. (C) shows induced elevation of HER3 by Tz and enhanced binding by HerPBK10. Parental cell lines were pre-treated with 0.5 mg/mL Tz for 24 hours before measuring cell surface HER3 levels. (D) shows induced elevation of HER3 by Tz and enhanced binding by HerPBK10. Parental cell lines were pre-treated with 0.5 mg/mL Tz for 24 hours before testing these cells for HerPBK10 binding. (E) shows cell surface receptor levels on primary tumor cells obtained from a surgical specimen of a HER2+ patient. (F) shows HerPBK10 binding on primary tumor cells obtained from a surgical specimen of a HER2+ patient.

Figure 43:
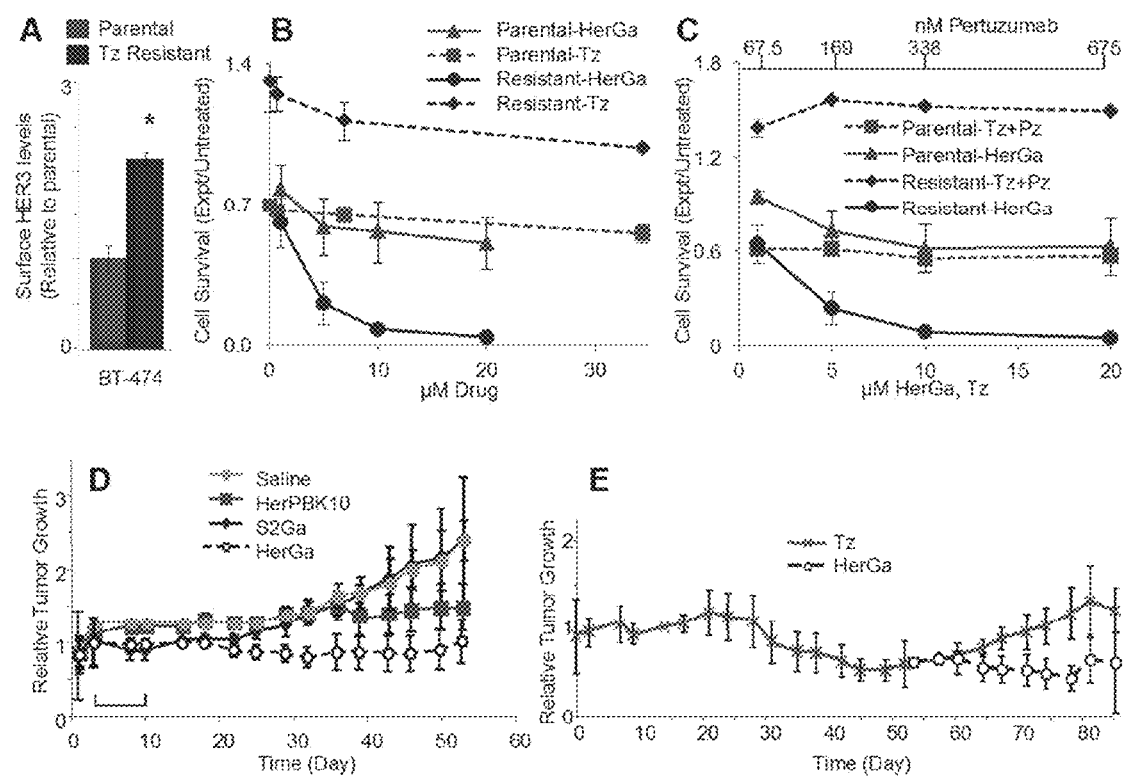

FIG. 43 illustrates that corrole nano-biological particles such as HerGa exhibit enhanced toxicity to Tz-resistant tumor cells in vitro and in vivo. (A) shows relative surface levels of HER3 on parental and trastuzumab resistant breast cancer cell lines, detected by ELISA without membrane permeabilization. N=3. *, $p<0.05$ compared to parental. (B) shows tumor cell killing by HerGa (by 48-72 hours after treatment) in comparison to Tz. N=3. (C) shows tumor cell killing by HerGa (by 48-72 hours after treatment) in comparison to Tz+Pz combination treatment. N=3. (D) shows ablation of tumor growth in vivo. Female nude mice bearing BT474 tumors received indicated reagents at indicated doses by intravenous injection (tail vein) when tumors reached ~100 mm³ (twice-weekly injections for 4-6 weeks). Tumor volumes were measured by calipers. Day 0 corresponds to first day of treatment. N=10 tumors per treatment. (E) shows ablation of tumor growth in vivo. Female nude mice bearing BT474 tumors received indicated reagents at indicated doses by intravenous injection (tail vein) when tumors reached ~100 mm³ (twice-weekly injections for 4-6 weeks). Tumor volumes were measured by calipers. Day 0 corresponds to first day of treatment. N=10 tumors per treatment.

DETAILED DESCRIPTION OF THE EMBODIMENTS

Methods of Treatment

In one aspect, disclosed herein are methods of treating cancer in a patient, the method comprising:
identifying a patient who is resistant to treatment with an anti-HER2 therapy; and
administering to the patient a therapeutically effective amount of a drug delivery molecule, comprising:
a polypeptide molecule adapted to target and/or penetrate a type of cell;
a nucleic acid molecule bound to the polypeptide sequence via electrostatic interactions; and
a chemical agent non-covalently linked to the nucleic acid sequence.

The drug delivery molecules used in the methods disclosed herein are described elsewhere. For example, International Publication WO 2009/009441 and U.S. Patent Application Publication US 2010/0331273 A1 describe in detail the components of the drug delivery molecules and methods of preparing the same. The content of both of these publications is incorporated by reference herein in their entirety including the drawings. Specifically, Paragraphs [0055]-[0094], the drawings and their descriptions, and the sequence listings of Publication US 2010/0331273 A1 are incorporated by reference herein.

"Therapeutically effective amount" as used herein refers to that amount which is capable of achieving beneficial results in a patient with cancer. A therapeutically effective amount can be determined on an individual basis and will be based, at least in part, on consideration of the physiological characteristics of the mammal, the type of delivery system or therapeutic technique used and the time of administration relative to the progression of the disease. A beneficial result is obtained when: 1) the cancerous tumor shrinks in size; 2) the cancerous tumor stops growing; or 3) the rate of growth of the cancerous tumor is slowed as compared to the time period before the administration of the therapy.

In some embodiments, the anti-HER2 therapy comprises antibody therapy. In these embodiments, an antibody that is effective against HER2 is administered to the patient. Examples of these antibodies include trastuzumab and pertuzumab, or biosimilars thereof. In other embodiments, the anti-HER2 therapy comprises small molecule therapy. In these embodiments, a small organic molecule, i.e., a compound that is not a polypeptide, a nucleic acid, or a polymer, which compound is effective against HER2 is administered to the patient. An example of a small molecule therapeutic is lapatinib.

In some embodiments, the polypeptide molecule comprises a targeting ligand. In certain embodiments, the polypeptide molecule comprises a positively charged domain. In other embodiments, the polypeptide is a recombinant fusion protein. In some of these embodiments, the recombinant fusion protein comprises a Her segment. In certain embodiments, the recombinant fusion protein comprises a penton base segment. In some embodiments, the polypeptide molecule comprises a receptor binding domain, which in some embodiments, is heregulin-α. In certain embodiments, the polypeptide molecule comprises an endosomolytic domain. In some of these embodiments, the endosomolytic domain comprises an Arg-Gly-Asp motif, while in other embodiments, the endosomolytic domain comprises a Glu-Gly-Asp motif. In certain embodiments, the polypeptide molecule comprises a polylysine motif, which in some embodiments is a decalysine (K10). In some embodiments, the polynucleotide sequence is SEQ ID NO:6, SEQ ID NO:7, SEQ ID NO:8, SEQ ID NO:9, or a combination thereof. In certain embodiments, the polypeptide sequence is HerPBK10.

As used herein, "PB" refers to a penton base segment that normally mediates cell binding, entry, and cytosolic penetration of adenovirus serotype 5 during the early stages of infection. An example of a penton base protein is provided herein as SEQ ID NO:10. This penton base protein normally has an RGD motif (Arg-Gly-Asp). As used herein, "K10" refers to a decalysine motif that has the capacity to bind nucleic acids by electrophilic interaction, provided herein as SEQ ID NO:11. An example of a nucleotide sequence coding for HerPBK10 is provided herein as SEQ ID NO:4 with its complement strand of SEQ ID NO:5. Similarly, a point mutation of the RGD motif may be used to create an EGD motif (Glu-Gly-Asp), resulting in a HerPBrgdK10 polypeptide molecule (rather than HerPBK10).

In some embodiments, the nucleic acid molecule is a double-stranded oligonucleotide. In some of these embodiments, the double-stranded oligonucleotide is bound to the recombinant fusion protein by electrostatic interactions.

In some embodiments, the chemical agent is a toxin. In some embodiments, the chemical agent is a chemotherapeutic agent, which in certain embodiments is doxorubicin, or a pharmaceutically equivalent thereof. In certain embodiments, the chemical agent is intercalated with the nucleic acid molecule. As used herein, "intercalating" refers to the ability to insert into an existing structure, such as a polynucleotide sequence.

"Chemotherapeutic agent" as used herein refers to agents with the capability to destroy, kill, hinder the growth of, and/or otherwise have a deleterious effect on cancer cells or tumors. These may include, but are in no way limited to, alkylating agents (e.g., busulfan, cisplatin, carboplatin, chlorambucil, cyclophosphamide, ifosfamide, dacarbazine, mechlorethamine, melphalan, and temozolomide), nitrosoureas (e.g., streptozocin, carmustine, and lomustine), anthracyclines and related drugs (e.g., doxorubicin, epirubicin, idarubicin, and mitoxantrone), topoisomerase I and II inhibitors (e.g., topotecan, irinotecan, etoposide and teniposide), and mitotic inhibitors (e.g., taxanes such as paclitaxel and docetaxel, and vinca alkaloids such as vinblastine, vincristine, and vinorelbine). Other chemotherapeutic agents will be understood by those of skill in the art and can be used in connection with alternate embodiments disclosed herein by exercise of routine effort.

In some embodiments, the type of cell is an anti-HER2 therapy resistant HER2+ breast cancer cell. Normally, HER2+ breast cancer cells respond to therapy, for example, by an anti-HER2 antibody, such as trastuzumab or pertuzumab, or by a small molecule, such as lapatinib. By "respond" to therapy it is meant that once the antibody is administered to the cancer cell, either by administering the antibody in vivo systemically to a cancer patient, or by contacting the cell in vitro with the antibody, either the number of the cells in the sample or in the patient decrease, for example through induced apoptosis, or the growth of the cells in the sample or in the patient is slowed or arrested. In patients, this is seen as shrinkage of the cancerous tumor, the lack of growth of the tumor, or a slowing of the growth of the tumor as compared to a period of time before the administration of the antibody. "Anti-HER2 therapy resistant HER2+ breast cancer cells" are those cells that do not respond to treatment by an antibody or a small molecule. These cells continue to grow even after the therapeutic agent is administered. Some cells are inherently resistant to treatment. These cells never respond to the treatment. Other cells acquire resistance to treatment. These cells first respond to the treatment, but after a period of time stop responding. Thus, the patient becomes refractory to the treatment.

In some embodiments, the HER2+ breast cancer cell has levels of surface HER3 higher than the levels of surface HER3 on a non-therapy-resistant HER2+ breast cancer cell. By "non-therapy-resistant HER2+ breast cancer cell" it is meant a HER2+ cancer cells that responds to the treatment with a therapeutic agent, such as an anti-HER2 antibody or a small molecule, and has not become refractory. In other embodiments, the resistant breast cancer cell shows the same level of surface HER3 expression as seen on a non-therapy-resistant HER2+ breast cancer cell. In certain embodiments, the anti-HER2 antibody is trastuzumab or pertuzumab. In some embodiments, the HER2+ breast cancer cell is inherently resistant to the anti-HER2 therapy, while in other embodiments the HER2+ breast cancer cell has acquired resistance to the anti-HER2 therapy.

In some embodiments, the methods described herein further comprise the step of co-administering an anti-HER2 therapeutic agent with the drug delivery molecule. In some of these embodiments, the therapeutic agent and the drug delivery molecule are administered simultaneously. In some of the embodiments, both the therapeutic agent and the drug delivery molecule are in the same administrable dosage form. In other embodiments, the therapeutic agent and the drug delivery molecule are administered at different times. In some embodiments, the patient is naïve to the therapeutic agent treatment. In other embodiments, the patient has been undergoing treatment with the therapeutic agent for some time, and then the drug delivery molecule treatment is added to the treatment regimen.

In some embodiments, the patient is a mammal selected from the group consisting of mouse, rat, rabbit, guinea pig, dog, cat, sheep, goat, cow, monkey, chimpanzee, ape, and human. In certain embodiments, the patient is a human.

In another aspect, disclosed herein are methods of inducing apoptosis in an anti-HER2 therapy resistant HER2+ breast cancer cell, the method comprising:
contacting the anti-HER2 therapy resistant HER2+ breast cancer cell with a drug delivery molecule, comprising:
a polypeptide molecule adapted to target and/or penetrate a type of cell;
a nucleic acid molecule bound to the polypeptide sequence via electrostatic interactions; and
a chemical agent non-covalently linked to the nucleic acid sequence.

In the embodiments of this aspect, the drug delivery molecule is as described above and elsewhere herein.

In some embodiments, the contacting is in vitro. For example, in these embodiments, the cells are grown in a laboratory and the contacting takes place as part of a laboratory experiment.

In some embodiments, the contacting is in vivo. In these embodiments, the drug delivery molecule, or a prodrug thereof, is administered to the patient. If a prodrug is administered, then the prodrug is converted to the drug delivery molecule and the contacting takes place in the patient's body.

In some embodiments, the anti-HER2 therapy resistant HER2+ breast cancer cell is a mammalian cell, which mammal is optionally selected from the group consisting of mouse, rat, rabbit, guinea pig, dog, cat, sheep, goat, cow, monkey, chimpanzee, ape, and human.

In a third aspect, described herein is a method of treating cancer in a patient, the method comprising:
identifying a patient who is resistant to anti-HER2 therapy; and
administering to the patient a therapeutically effective amount of a drug delivery molecule, comprising:
a polypeptide molecule adapted to target and/or penetrate a type of cell; and
a sulfonated corrole molecule bound to the polypeptide sequence.

In some embodiments of this aspect, the sulfonated corrole molecule includes a metal such as, but not limited to, Manganese (Mn), Iron (Fe), and/or Gallium (Ga). In some embodiments, the drug delivery molecule is HerMn, HerFe, or HerGa. In one embodiment, the anti-HER2 therapy comprises antibody therapy. In some of these embodiments, the antibody is trastuzumab or pertuzumab. In another embodiment, the anti-HER2 therapy comprises small molecule therapy. In some of these embodiments, the small molecule is lapatinib.

In some embodiments, the polypeptide molecule comprises a targeting ligand. In some embodiments, the polypeptide molecule comprises a positively charged domain. In some embodiments, the polypeptide is a recombinant fusion protein. In some of these embodiments, the recombinant fusion protein comprises a Her segment. In other embodiments, the recombinant fusion protein comprises a penton base segment. In some embodiments, the polypeptide molecule comprises a receptor binding domain. In some of these embodiments, the receptor binding domain is heregulin-α. In some embodiments, the polypeptide molecule comprises an endosomolytic domain. In some of these embodiments, the endosomolytic domain comprises an Arg-Gly-Asp motif. In other embodiments, the endosomolytic domain comprises a Glu-Gly-Asp motif. In some embodiments, the polypeptide molecule comprises a polylysine motif. In some of these embodiments, the polylysine motif is a decalysine.

In one embodiment, the polynucleotide sequence is SEQ ID NO:6, SEQ ID NO:7, SEQ ID NO:8, SEQ ID NO:9, or a combination thereof. In one embodiment, the polypeptide sequence is HerPBK10. An example of a nucleotide sequence coding for HerPBK10 is provided herein as SEQ ID NO:4 with its complement strand of SEQ ID NO:5.

In one embodiment, the type of cell is an anti-HER2 therapy resistant HER2+ breast cancer cell. In some of these embodiments, the HER2+ breast cancer cell has levels of surface HER3 higher than the levels of surface HER3 on a HER2+ breast cancer cell that responds to therapy. In some embodiments, the HER2+ breast cancer cell is inherently resistant to the anti-HER2 therapy. In other embodiments, the HER2+ breast cancer cell has acquired resistance to the anti-HER2 therapy.

In some embodiments, the patient is a mammal selected from the group consisting of mouse, rat, rabbit, guinea pig, dog, cat, sheep, goat, cow, monkey, chimpanzee, ape, and human.

In a fourth aspect described herein are methods of inducing apoptosis in an anti-HER2 therapy resistant HER2+ breast cancer cell, the method comprising:
contacting the anti-HER2 therapy resistant HER2+ breast cancer cell with a drug delivery molecule, comprising:
a polypeptide molecule adapted to target and/or penetrate a type of cell; and
a sulfonated corrole molecule bound to the polypeptide sequence.

In some embodiments of this aspect, the sulfonated corrole molecule includes a metal such as, but not limited to, Manganese (Mn), Iron (Fe), and/or Gallium (Ga). In some embodiments, the drug delivery molecule is HerMn, HerFe, or HerGa. In one embodiment, the anti-HER2 therapy comprises antibody therapy. In some of these embodiments, the antibody is trastuzumab or pertuzumab. In another embodiment, the anti-HER2 therapy comprises small molecule therapy. In some of these embodiments, the small molecule is lapatinib.

In some embodiments, the polypeptide molecule comprises a targeting ligand. In some embodiments, the polypeptide molecule comprises a positively charged domain. In some embodiments, the polypeptide is a recombinant fusion protein. In some of these embodiments, the recombinant fusion protein comprises a Her segment. In other embodiments, the recombinant fusion protein comprises a penton base segment. In some embodiments, the polypeptide molecule comprises a receptor binding domain. In some of these embodiments, the receptor binding domain is heregulin-α. In some embodiments, the polypeptide molecule comprises an endosomolytic domain. In some of these embodiments, the endosomolytic domain comprises an Arg-Gly-Asp motif. In other embodiments, the endosomolytic domain comprises a Glu-Gly-Asp motif. In some embodiments, the polypeptide molecule comprises a polylysine motif. In some of these embodiments, the polylysine motif is a decalysine.

In one embodiment, the polynucleotide sequence is SEQ ID NO:6, SEQ ID NO:7, SEQ ID NO:8, SEQ ID NO:9, or a combination thereof. In one embodiment, the polypeptide sequence is HerPBK10. An example of a nucleotide sequence coding for HerPBK10 is provided herein as SEQ ID NO:4 with its complement strand of SEQ ID NO:5.

In one embodiment, the type of cell is an anti-HER2 therapy resistant HER2+ breast cancer cell. In some of these embodiments, the HER2+ breast cancer cell has levels of surface HER3 higher than the levels of surface HER3 on a HER2+ breast cancer cell that responds to therapy. In some embodiments, the HER2+ breast cancer cell is inherently resistant to the anti-HER2 therapy. In other embodiments, the HER2+ breast cancer cell has acquired resistance to the anti-HER2 therapy.

In some embodiments, the patient is a mammal selected from the group consisting of mouse, rat, rabbit, guinea pig, dog, cat, sheep, goat, cow, monkey, chimpanzee, ape, and human.

In some embodiments, contacting the anti-HER2 therapy resistant HER2+ breast cancer cell with a drug delivery molecule is in vitro. In other embodiments, the contacting is in vivo.

In some embodiments, the anti-HER2 therapy resistant HER2+ breast cancer cell is a mammalian cell. In some embodiments, the mammal is selected from the group consisting of mouse, rat, rabbit, guinea pig, dog, cat, sheep, goat, cow, monkey, chimpanzee, ape, and human.

Drug Delivery Molecule

Disclosed herein are delivery systems including a self-assembling complex for targeting chemical agents to cells. The delivery system is capable of targeting diseased cells in vitro and in vivo, avoids heart tissue (where desirable to do so), and binds and penetrates into target cells. Furthermore, the complex is assembled non-covalently (i.e., without the need for chemical coupling of, for instance, a chemotherapeutic to a targeted carrier) and it uses a small nucleic acid carrier as a bridge to assemble the drug with the targeted protein carrier vehicle.

Any number of polynucleotide sequences or small double-stranded nucleic acids may be used in accordance with various embodiments described herein. For example, in one embodiment, SEQ ID NO:6, SEQ ID NO:7, SEQ ID NO:8, SEQ ID NO:9, or a combination thereof, is used as a polynucleotide sequence or double stranded nucleic acid.

Any number of targeting ligands may be used in accordance with various embodiments described herein. For example, PB itself may act as a targeting ligand of PBK10 when targeting integrins such as αvβ3. As known by one of skill in the art, integrins are overly expressed in various types of metastatic tumors. Thus, in conjunction with various embodiments described herein, PBK10 may be used to target metastatic tumors and cells with a high expression of integrins.

The disclosed delivery system includes a complex that can be administered to a mammal by various routes of administration, whereupon it hones in on target cells (e.g., cancer cells) to deliver molecules such as imaging agents or therapeutic agents into the cells. In one embodiment, the complex provides for delivery of therapeutic agents to cancer cells while sparing normal, healthy cells.

Figure 1:
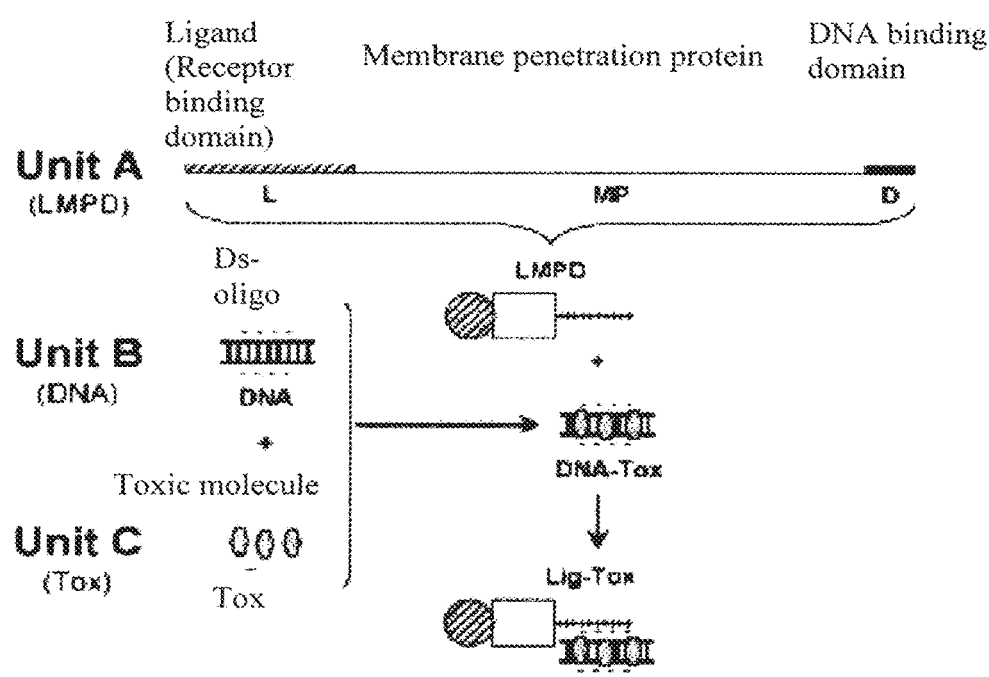
FIG. 1 illustrates a delivery system in accordance with an embodiment of the present invention.

As shown in FIG. 1, an embodiment of the disclosed delivery system includes three components that self-assemble into one targeted conjugate. The first component ("Unit A") is a unique cell-penetrating protein that targets and penetrates a particular type of cell(s). It includes a ligand (receptor binding domain), a membrane penetration domain, and a DNA binding domain. The second component ("Unit B") is a small nucleic acid (e.g., a double-stranded oligonucleotide) that binds to Unit A via electrostatic interactions. The third component ("Unit C") is a chemical agent that binds Unit B via intercalation interactions. In one embodiment the chemical agent is a toxic molecule. In one embodiment, the type of cell is a cancer cell, and the chemical agent is a chemotherapeutic agent. In another embodiment, the type of cell is HER2+ breast cancer cells, and the chemical agent is Dox, or a pharmaceutically equivalent thereof.

In one embodiment, HerPBK10 is mixed with a small 30-base pair double-stranded nucleic acid (ds-oligo) containing intercalated doxorubicin (Dox). In some embodiments, this results in non-covalent assembly of 10-50 nm diameter round particles, as observed by cryoEM (FIG. 24 B) that retain Dox during ultrafiltration, HPLC (FIG. 24 C), prolonged storage at different temperatures, and resist drug release in serum (FIG. 24 D) and blood (FIG. 24 E). In some of these embodiments, the sequence of the ds-oligo has no bearing on Dox loading and a longer ds-oligo, such as a 48-bp fragment, does not necessarily show improved loading capacity. In some embodiments, one 30-bp oligo can bind up to and including 50 molecules of doxorubicin. In one embodiments, the assembled nanoparticle comprising protein, DNA, and Dox binds up to and including 10 molecules of the protein complex HerPBK10. In another embodiment, UV/Vis spectroscopy of assembled particles has verified that each ds-oligo fragment binds about 5, 6, 7, 8 or more molecules of HerPBK10 and about 10-40 molecules of Dox. This is in agreement with the predicted molar ratios needed to neutralize the DNA and saturate it with intercalated Dox.

In some embodiments, HerDox exhibits receptor-dependent targeting to HER2+ cells in vitro and in vivo. In one of those embodiments, as illustrated in FIG. 25-A, the HerDox particle is preferentially toxic to HER2+ but not HER2− cells in both separate (FIG. 25-A) and mixed cell cultures (FIG. 9). In another embodiment, the HerDox particle is toxic to HER2− cells such as triple negative breast cancer (TNBC) cells that overexpress HER3. Cytotoxicity is inhibited by receptor-blocking. FIG. 25-B shows that HerDox displays preferential biodistribution to tumor cells with higher, in comparison to lower, receptor levels in vivo. In one embodiment, shown in FIG. 25-C, tumor targeting and intracellular trafficking studies show that Dox does not exhibit release from the HerDox particle until after cell entry, at which point the Dox rapidly accumulates in the nucleus while HerPBK10 remains at the nuclear periphery. FIGS. 25-D and 25-E show that systemic delivery in vivo elicits HER2+ tumor cell death at very low pharmacologic dose (0.004 mg/kg of Dox) while avoiding liver and heart toxicity. This contrasts with untargeted Dox, which requires higher doses to elicit similar tumor toxicity while causing liver tissue and myocardial damage.

In one embodiment, resistance to HER2 inhibition makes tumors particularly prone to HerDox attack. Nevertheless, resistance is not a pre-requisite for HerDox efficacy—HerDox is effective on both trastuzumab sensitive and resistant tumor cells, and has advantages over signal inhibition on both, but especially resistant cells.

In various embodiments, the disclosed delivery system is incorporated into a pharmaceutical composition, which may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

In some embodiments, the pharmaceutical compositions also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In some embodiments, the pharmaceutical compositions are encapsulated, tableted or prepared in an emulsion or syrup for oral administration.

Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulating, and compressing, when necessary, for tablet forms; or milling, mixing and filling for producing hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions disclosed herein may be delivered in a therapeutically effective amount. The precise therapeutically effective amount is that amount of the composition that will yield the most effective results in terms of efficacy of treatment in a given subject. This amount will vary depending upon a variety of factors, including but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of the disclosed delivery system and, more specifically, the therapeutic agents (e.g., chemotherapeutic agents), particularly Dox, and/or the imaging agents delivered by it is in the ranges recommended by the manufacturer where known therapeutic compounds or imaging agents are used, and also as indicated to the skilled artisan by the in vitro responses or responses in animal models. The actual dosage will depend upon the judgment of the physician, the condition of the patient, and the effectiveness of the therapeutic method.

Also disclosed are methods of treating diseases by administration to a mammal in need thereof of a therapeutically effective amount of the disclosed delivery system including a therapeutic agent appropriate to treat the disease. In one embodiment, the disease is cancer and the therapeutic agent is a chemotherapeutic agent. In another embodiment, the disease is breast cancer and/or HER2+ breast cancer, and the therapeutic agent is Dox.

Delivery of a Drug

In one embodiment, the drug delivery molecule disclosed herein advances the delivery to the tumor site of existing compounds. In some of these embodiments, the drug delivery molecule disclosed herein is used to improve the delivery of a compound known to exhibit a therapeutic efficacy. In some embodiments, the compound is approved by the U.S. Food and Drug Administration (FDA) for the treatment of a disease. In certain embodiments, the FDA-approved drug is used for an off-label use. In one embodiment the drug is Doxorubicin. In some embodiments, the stable trapping of the drug in the HerDox complex contributes to the efficacy and safety of the drug in the drug delivery molecule. This approach is advantageous over loading the drug into capsules which is prone to leakage by diffusion, or chemically modifying the drug through covalent conjugation which is prone to affecting its activity and potency.

Comparison to HER2 Inhibitors.

The HER3 elevation associated with resistance to HER2 and EGFR inhibition has spurred the development of anti-HER3 antibodies to suppress signaling through HER3. HerDox has several advantages over such inhibitors. In one embodiment, HerPBK10 does not rely on signal attenuation for its therapeutic activity, but instead uses HER3 as a portal to rapidly endocytose into tumor cells and kill the cells from within through the delivery of a toxic molecule. In some embodiments, unlike HerPBK10, antibodies does not trigger uptake. Instead antibodies internalize passively, slowly, and at low levels.

As one example, there are important differences between HerDox and Trastuzumab-conjugated emtansine (T-DM1), which was recently approved for clinical use. First, T-DM1 is targeted to HER2 and thus it is not aimed towards tumors resistant to HER2 inhibition. Second, while T-DM1 is intended to undergo internalization for delivery of the mitotic inhibitor, emtansine, HER2 on its own does not endocytose but instead relies on passive cell entry by receptor turnover or co-uptake with HER3-bound ligands. Therefore uptake of trastuzumab (Tz) conjugates is slow (on the order of hours) and relatively low in contrast to the robust entry triggered by HER-ligand binding. This result is shown in FIG. 30 that compares HerPBK10 uptake to Tz uptake. Third, resistance to T-DM1 is mediated by induction of HER3 and drug efflux transporters. On the other hand, Dox remain protected in the HerDox particle until after cell uptake and trafficking toward the nucleus, where the drug is released for nuclear accumulation. This particle trafficking evades drug efflux transporters.

These differences between the mechanism of action between HerDox and other antibodies impacts the dosage required for therapeutic efficacy. As one example, the Inventors have shown that about 0.004 mg/kg HerDox is sufficient to target and ablate tumor growth while sparing normal tissue such as the heart and liver in mice. This contrasts with the therapeutic dose required for T-DM1 (about 3.6 mg/kg), and untargeted Dox in patients (about 1-5 mg/kg) and mice (more than 0.04 mg/kg), which elicits well-known adverse effects on off-target tissue.

In one embodiment, the method of treating cancer described herein is used in the treatment of triple-negative breast cancer (TNBC). TNBC is inherently HER2-resistant. The lack of estrogen, progesterone, and HER2 receptors on these tumors limits the types of targeted therapies that can be used. Recent studies show that TNBC express HER3. While EGF-R inhibitors have been explored for these tumors, resistance to such inhibitors is also facilitated by elevated HER3. The methods of treating cancer described herein are applicable to such inherently HER2-resistant tumors. Similarly the methods described herein are also applicable to tumors in the breast, gastric, colon, lung, and ovary where HER3 up-regulation is identified in response to EGFR, HER2, and PI3K kinase inhibitors.

Herdox Mechanism of Action

In some embodiments, HER2+ tumors with acquired resistance to HER2 inhibitors are sensitive to HerDox due to (i) HER3-mediated targeting, (ii) receptor sequestration and downregulation by particle endocytosis and endosomolysis, and/or (iii) endosomal and particle trafficking that affords payload protection and evasion of drug efflux.

In some of these embodiments, HER3 clustering, endocytosis, and endosomolysis induced by HerDox sequesters HER3 from HER2 activation and blunts the signaling endosome. In one embodiment, in addition to elevated HER3 facilitating targeting to resistant cells, the multivalency of HerPBK10 nanoparticles induce HER3 homo-oligomerization and sequestration away from HER2 (and any other tyrosine kinases), thus preventing HER3 phosphorylation and activation. In another embodiment, HER3 elevation also facilitate the formation of ligand-induced HER3 homo-oligomers, and thus such a phenomenon is particular to resistant cells. Moreover, disruption of receptor-sequestered vesicles by endosomolysis, which enables entry into the cytoplasm, extinguishes endosomal signaling while supporting delivery of Dox to intracellular targets of toxicity, thus contributing to overall cytotoxicity.

In some embodiments, endosomal and particle trafficking protect the payload from drug efflux. A combination of endocytic transport, drug encapsulation by HerPBK10, and HerDox transit to the nuclear periphery contribute to evasion of drug efflux. In some embodiments, HerDox yields improved targeted toxicity to HER2+ tumors with acquired resistance to HER2 inhibitors compared to combination therapy. These HER2 monotherapies and combination treatments include, but is not limited to, Tz, Tz-Pz, Tz-Lp and T-DM1.

In some embodiments, the efficacy of HER2− inhibitors is augmented when used as adjuvants to HerDox therapy on naïve HER2+ tumors. In some of these embodiments, HER2-inhibitors induce HER3 and sensitize naïve tumors to HerDox in vivo. In other embodiments, HerPBK10 binds to tumor tissue from HER2+ patients via HER3. In one embodiment, HER2− inhibition does not induce HerDox toxicity to human CDCs.

In some embodiments described herein, HER2− breast tumors, including TNBC, are targetable by HerDox via HER3 and is further sensitized by adjuvant treatment with EGF-R inhibitors. In some of these embodiments, EGF-R inhibitors induce HER3 elevation and sensitize TNBC cells to HerDox in vitro. In some embodiments, HerDox is therapeutically effective on a TNBC model in both a metastatic and immunocompetent setting.

Corroles as Novel Payloads

Corroles are defined and described in the art, for example in U.S. Patent Application Publication No. US 2014/0335025 A1, the entire disclosure of which is incorporated by reference herein, including the drawings.

Disclosed herein are methods of treating cancer in a patient, the method comprising identifying a patient who is resistant to anti-HER2 therapy; and administering to the patient a therapeutically effective amount of a drug delivery molecule, comprising a polypeptide molecule adapted to target and/or penetrate a type of cell; and a sulfonated corrole molecule bound to the polypeptide sequence. Also disclosed herein are methods of inducing apoptosis in an anti-HER2 therapy resistant HER2+ breast cancer cell, the method comprising contacting the anti-HER2 therapy resistant HER2+ breast cancer cell with a drug delivery molecule, comprising a polypeptide molecule adapted to target and/or penetrate a type of cell; and a sulfonated corrole molecule bound to the polypeptide sequence.

Corroles are structurally similar to porphyrins. In some embodiments, the corrole is a sulfonated corrole. In some embodiments, the sulfonated corroles are amphiphilic, soluble in physiological solutions, and/or binds to polypeptides through non-covalent interactions. In some embodiments, the non-covalent interactions are electrostatic interactions. In some embodiments, the polypeptide is a recombinant protein. In some embodiments, the recombinant protein is a recombinant fusion protein. The anionic sulfonate groups prevent non-specific cell entry due to repulsion by the negatively charged cell membrane, thereby directing corrole delivery into target cells via a carrier protein.

In some embodiments, the corrole comprises a metallic chemical element. In some of these embodiments, the metal is a transition metal. In some embodiments, the metal is Iron (Fe), Manganese (Mn), or Gallium (Ga). In other embodiments, the corrole is non-metallated. Metallated and non-metallated corroles bind in protein pockets with negligible dissociation. As one illustrative example, the HerGa described in FIG. 33, is composed of a sulfonated gallium (III) corrole (S2Ga) assembled with HerPBK10. HerGa resists corrole transfer to serum proteins in vitro and in vivo. Corrole assembly with HerPBK10 yields 25-35 corroles/protein, resulting in 10-20 nm round particles (FIG. 33-B) that withstand high-speed ultrafiltration. As another illustrative example, HerMn, a sulfonated manganese(III) corrole (S2Mn) assembled with HerPBK10, forms about 20 nm round particles (FIG. 33-C).

In one embodiment, HerGa, in addition to being intensely fluorescent, exhibits tumor-preferential targeting in vivo after systemic delivery, bypassing most normal tissue including the heart, and elicits tumor growth ablation at very low pharmacologic dose (0.008 mg/kg). In another embodiment, HerMn exhibits similar tumor preferential targeting and growth ablation in vivo, and while not fluorescent, enables more clinically relevant imaging via magnetic resonance (MR). In both of these embodiments, HerGa and HerMn causes ROS-mediated cytoskeletal and mitochondrial disruption. Corroles such as, but not limited to, HerGA targets and/or binds to the mitochondrial TSPO protein, important in cellular homeostasis and tumor maintenance. Similarly, a sulfonated non-metallated free-base corrole (S2FB) (FIG. 33-C), which is also intensely fluorescent, can directly interact with SOD1 (FIG. 34-B) and inhibit SOD activity (FIG. 34-A), by chelation of the metal ligand from the enzyme (FIG. 4C).

In one embodiment, the HerPBK10-corrole particle described herein alters its fluorescence lifetime in response to the pH. Thus the corrole particle serves as a diagnostic probe broadcasting the microenvironmental conditions in its immediate vicinity. This feature is useful at the cellular level, such as for studying trafficking pathways or subcellular location. This feature is also useful at the tissue level, such as for identifying sites of tumor growth. As one non-limiting example, the fluorescence lifetime of HerGa differs depending on whether it is in tumor or liver tissue, both ex vivo and in vivo, thereby enabling the distinction between tumor and non-tumor tissue by optical imaging. As another non-limiting example, HerMn is useful for tumor detection because the HerMn particle prevents corrole interaction with water molecules in solution whereas tumor entry improves T1 relaxation shortening and corrole-enhanced contrast, suggestive of S2Mn corrole release from the particle after tissue uptake. As a third non-limiting example, HerGa is retained and detectable in a tumor for a prolonged period (up to and including 30 days) after IT injection but was cleared from non-tumor tissue sooner when injected subcutaneously. This feature, which may be facilitated in part by HerPBK10, contributes a possible advantage that HerMn may have over HerGd (Gd=gadolinium) because HerGd rapidly clears after injection.

In another embodiment, the HerPBK10-corrole particle described herein acts as a photosensitizer. Photoexcitation at the maximum fluorescence wavelength of S2Ga generated singlet oxygen that induced rapid damage to cells that had taken up HerGa. Whereas HerGa has already exhibited sufficient tumor toxicity without irradiation, photoexcitation at 424 nm substantially reduced the IC50 of HerGa hundred to thousand fold in vitro. Excitation at a secondary absorbance peak (about 620 nm) yielded nearly as effective cell death, thus enabling the use of longer wavelengths for irradiation that would support penetration into deeper tissue.

In another embodiment, corrole nanobiologics described herein addresses drug-resistant cancer cells. The HER3 elevation facilitating resistance to HER2 inhibition makes these tumors particularly prone to tumor-targeted corrole treatment. Therefore, HER2 inhibitors, such as Tz, acts as adjuvants, sensitizing tumors to corrole nanotherapy by causing HER3 elevation.

In some embodiments, the therapeutic efficacy of tumor-targeted corroles is enhanced on inhibitor-resistant tumor cells due to a combination of HER3-mediated receptor downregulation, particle trafficking, and corrole-mediated toxicity to multiple intracellular targets.

In one embodiment, HER3 clustering, endocytosis, and endosomolysis induced by corrole particles sequesters HER3 from HER2 activation and blunts the signaling endosome. In addition to elevated HER3 facilitating targeting to resistant cells, the multivalency of HerPBK10 nanoparticles induces HER3 homo-oligomerization and sequestration away from HER2 (and other tyrosine kinases) thus preventing HER3 phosphorylation and activation. HER3 elevation facilitates the formation of ligand-induced HER3 homo-oligomers, and such a phenomenon is particular to resistant cells. Moreover, disruption of receptor-sequestered vesicles by endosomolysis, which enables entry into the cytoplasm, extinguishes endosomal signaling while supporting delivery of corroles to intracellular targets of toxicity, thus contributing to overall cytotoxicity. This is consistent with the inventors observation that HerPBK10 alone does not induce tumor cell proliferation in vitro or in vivo despite its derivation from a signal-stimulating ligand.

In another embodiment, corroles evade drug efflux by rapid transfer to cellular proteins after cytoplasmic entry. HerGa fluorescence spreads throughout the cytoplasm in live cells after vesicle escape whereas HerPBK10 accumulates at the nuclear periphery. Moreover, free S2Mn but not the HerMn particle exhibits significant T1 relaxation shortening in solution, whereas HerMn exhibits improved T1 shortening upon tissue uptake. The term "T1 relaxation" as used herein, refers to spin-lattice relaxation. Moreover, low pH does not release S2Ga from HerPBK10. These findings together illustrate that corroles are released from HerPBK10 after cytoplasmic entry through a pH-independent mechanism. Furthermore, the widespread effect of oxygen radical-induced damage to the cytoskeleton and mitochondria, which requires close proximity of ROS generation, illustrates that corroles attach to and damage cellular organelles in a global manner. Therefore, corroles rapidly transfer to intracellular proteins after cell uptake, which helps keep corroles sequestered from drug efflux transporters.

In another embodiment, toxicity and imaging is augmented by combining complementary corrole activities. The combination of S2FB-mediated SOD inhibition, S2Ga or S2Mn-mediated ROS elevation, and S2Ga-mediated TSPO inhibition, augments toxicity by combining complementary activities. Such an approach also combines different detection modalities, such as fluorescence and MRI.

In some embodiments, tumor-homing corroles target HER2+ tumors that resist HER2 inhibition in vivo.

In one of these embodiments, particle distribution to resistant tumors in vivo correlates with HER3. HER2-inhibitor resistant tumors (such as, BT-474R and JIMT-1) exhibit higher rates of particle-accumulation compared to parental tumors (such as, BT-474) due to elevated HER3. In some of these embodiments, tumor targeting in vivo is mediated by HER3.

In another embodiment, corrole particles yield improved targeted toxicity to HER2+ tumors with acquired and pre-existing resistance to HER2 inhibitors compared to combination therapy. In another embodiment, HER2 signal-blocking inhibitors acts as adjuvants for optimized Her-targeted corrole nanoparticle mediated therapy.

In some embodiments, tumor-homing corroles target TNBC tumors via HER3 in an immunocompetent setting of disseminated cancer.

In some of these embodiments, EGF-R inhibitors induce HER3 elevation and sensitize TNBC cells to corrole particles in vitro. In one embodiment, HerPBK10 binds HER3 on mouse 4T1 cells, and HER3 levels are even higher on human BT-549 cells, illustrating that optimized Her-targeted corrole nanoparticles elicits targeted toxicity to these TNBC cell lines. Additionally, the elevation of HER3 associated with resistance to EGF-R inhibition on TNBC15, illustrates that such inhibitors augments optimized Her-targeted corrole nanoparticle targeting and toxicity to these cells.

In another embodiment, corrole particles are therapeutically effective on a TNBC model in both a metastatic and immunocompetent setting. The BALB/c-4T1 model is commonly used as a model of TNBC and disseminated cancer. When transplanted into mouse mammary glands, 4T1 cells form tumors that metastasize to the lung and brain, representing a stage IV breast cancer model. This syngeneic model illustrates targeted toxicity to disseminated tumors, and assesses the therapeutic efficacy of optimized Her-targeted corrole nanoparticles in the presence of an intact immune environment.

EXAMPLES

The following examples are provided to better illustrate the claimed invention and are not to be interpreted as limiting the scope thereof. To the extent that specific materials are mentioned, it is merely for purposes of illustration and is not intended to limit the claimed invention. One skilled in the art may develop equivalent means or reactants without the exercise of inventive capacity and without departing from the scope of the claimed invention.

Example 1: Targeted Delivery of Chemotherapeutic to HER2+ Breast Cancer Cells

Figure 2:
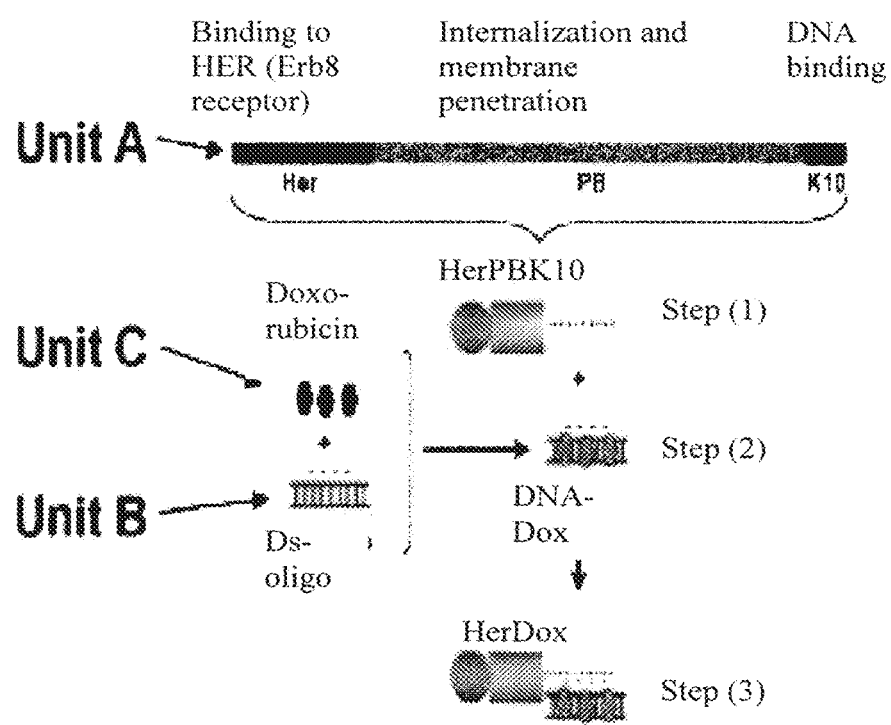
FIG. 2 illustrates a delivery system configured for the delivery of Dox to HER2+ breast cancer cells in accordance with an embodiment of the present invention. Step (1) illustrates HERPBK10 produced and purified as a recombinant fusion protein in bacterial. Step (2) illustrates DNA-Dox formed by noncovalent intercalation interaction. Step (3) illustrates DNA-Dox binds HerPBK10 by noncovalent charge interaction (anionic DNA phosphates electrophillicaly bind cationic polylysine).

The disclosed technology was tested on HER2+ breast cancer cells in vitro and in vivo. As illustrated in FIG. 2, to engineer the drug delivery molecule to target HER2+ breast cancer, Unit A includes a protein called HerPBK10, which is generated by the methods described in L. K. Medina-Kauwe et al. Gene Therapy, 8:1753-1761 (2001), incorporated by reference herein in its entirety. HerPBK10 contains the receptor binding domain of heregulin fused to the cell penetrating adenovirus penton base protein modified by a carboxy (C)-terminal decalysine. The 'Her' segment of HerPBK10 is obtained from the receptor binding domain of heregulin-α, which binds specifically to HER2/HER3 or HER2/HER4 subunit heterodimers. Although heregulin interacts directly with HER3 or HER4, but not HER2, ligand affinity is greatly enhanced by HER2. Thus, tumor cells that over-express HER2 (i.e., HER2+ tumor cells) are believed to be good candidates for heregulin-directed targeting.

The membrane penetrating activity of the adenovirus serotype 5 (Ad5) penton base protein is incorporated into the TB' segment of HerPBK10 to facilitate penetration into target cells. The 'K10' segment includes ten lysine residues, whose positive charge facilitates the transport of negatively charged molecules, such as nucleic acids, by electrophilic interaction.

Unit B includes two complementary oligonucleotides annealed together to form a small double-stranded nucleic acid. Unit C is comprised of the chemotherapy agent, Dox. The three components are assembled together in two steps by incubation at room temperature. In step 1, the Unit B DNA is incubated with the Unit C Dox to form a DNA-Dox assembly (i.e., Unit B+Unit C). This forms by intercalation of the Dox molecules in between the DNA base pairs. In step 2, the DNA-Dox assembly is incubated with HerPBK10 to form a final complex called HerDox (i.e., Unit A+Unit B+Unit C). This interaction is formed by the electrophilic binding of the negatively charged DNA phosphate backbone to the positively charged polylysine tail of HerPBK10.

Figure 3:
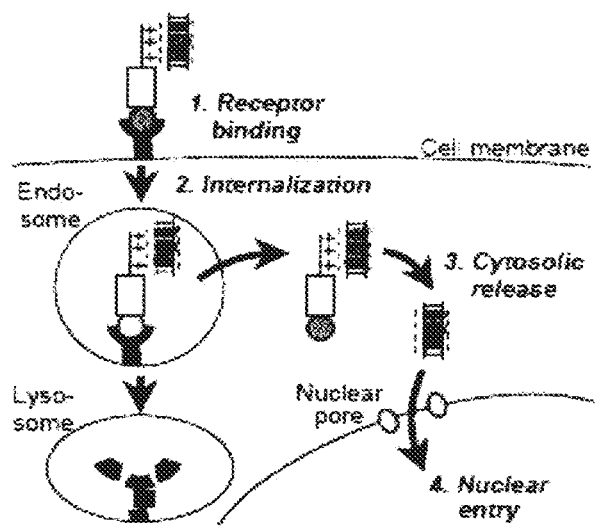
FIG. 3 illustrates a schematic of the operation of a delivery system configured for the delivery of Dox to HER2+ breast cancer cells in accordance with an embodiment of the present invention, including (1) receptor binding at the cell membrane, (2) internalization of the complex, (3) cytosolic release of the chemo therapeutic (Dox) non-covalently bonded to dsDNA via intercalation interactions, and (4) nuclear entry of the chemotherapeutic and dsDNA.

FIG. 3 illustrates a schematic of the operation of the disclosed delivery system in this particular embodiment thereof, and FIG. 11-B illustrates its successful application, in vivo, as compared with conventional administration of Dox. Through use of the disclosed delivery system, delivery of Dox was targeted to cancerous cells; relatively higher quantities of the drug were delivered to the cancerous cells as compared with conventionally delivered Dox, and relatively lower quantities of the drug reached non-target healthy tissues.

Example 2: HerDox is Highly Stable During Assembly

Figure 4:
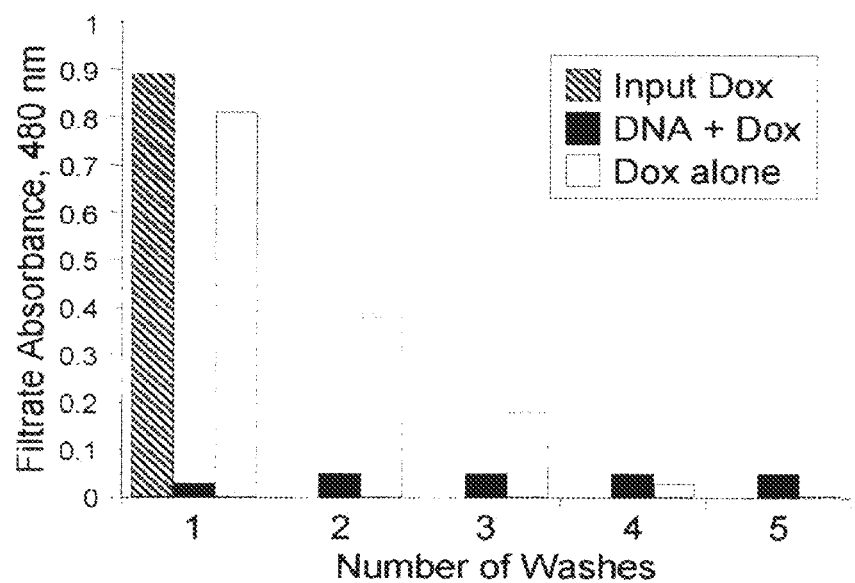
FIG. 4 (A) illustrates relative Dox in filtrates during the DNA-Dox assembly. The ds-oligo, prepared by annealing complimentary 30 bp oligonucleotides, was incubated for one hour at room temperature with Dox at 1:16 molar ratio DNA:Dox. Free Dox was removed by filtration through 10 MW cutoff spin columns. After the first Dox removal spin (Wash 1) the filters were washed 4 more times with HEPES buffered saline (HBS) (Washes 2-5).
Figure 4:
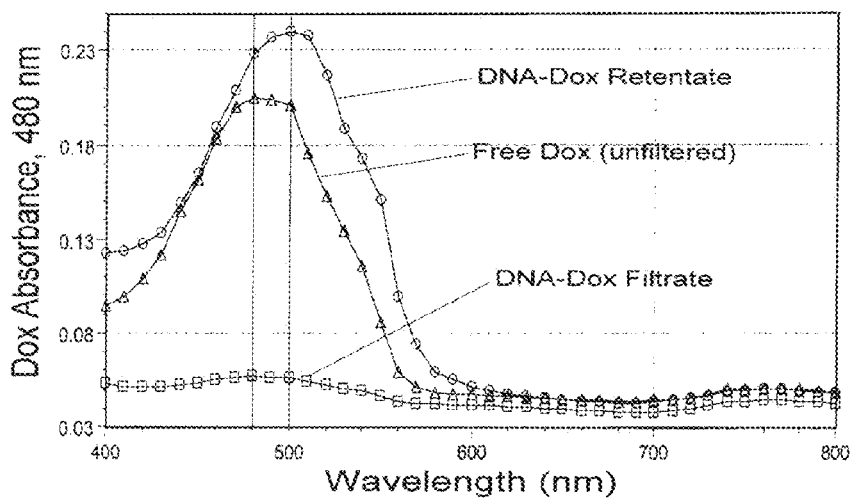
Figure 5:
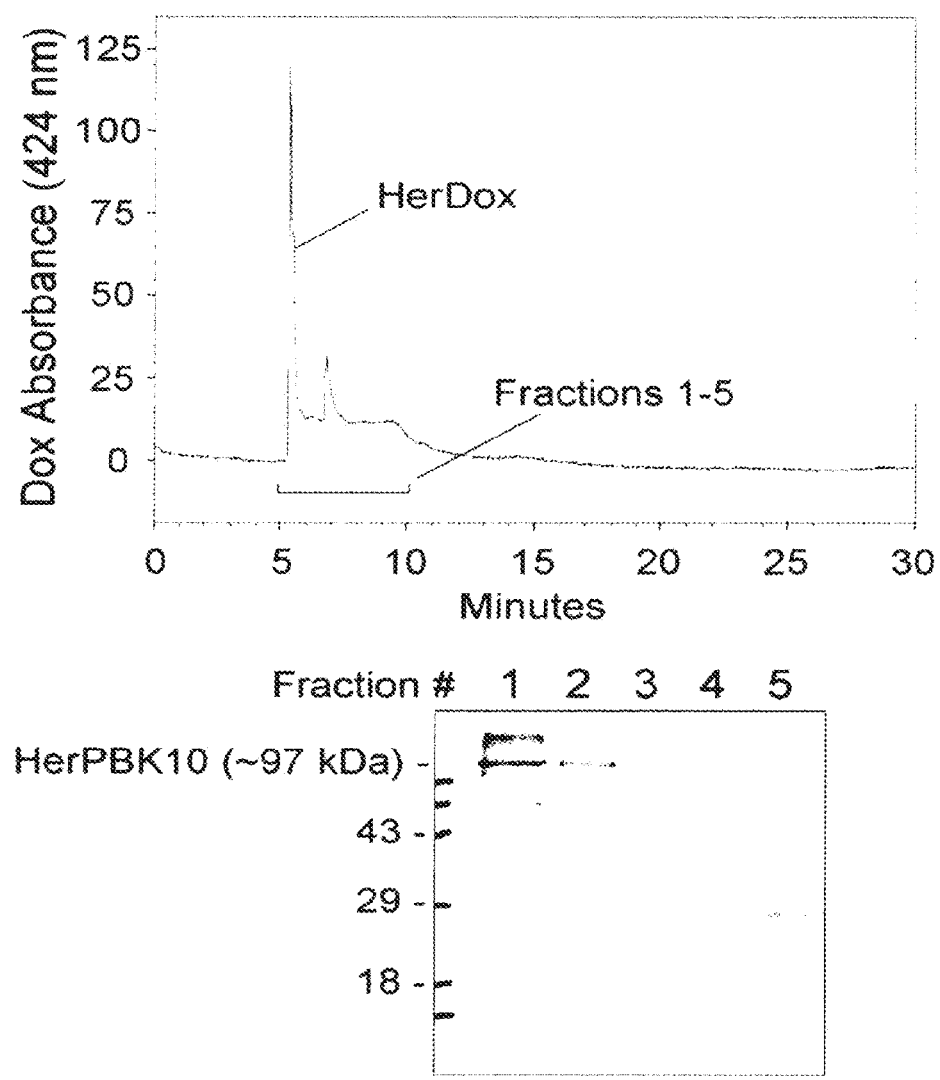
FIG. 5 illustrates HerDox assembly. DNA-Dox was incubated with HerPBK10 on ice for 2 h at 9:1 molar ratio HerPBK10:DNA-Dox. The mixture was subject to size exclusion HPLC and fractions collected at minutes 6-10 for SDS-PAGE and immunoblotting. HerDox was collected from the 6 min peak. The concentration of Dox in HerDox was assessed by measuring absorbance at 480 nm (Dox absorbance wavelength). HPLC purification of HerDox fractions 1-5 correspond to samples collected at minutes 6-10.

HerDox consists of three components: Dox; a small double-stranded nucleic acid (which is directly responsible for carrying Dox); and the targeted protein, HerPBK10. HerDox is assembled in two steps. First, Dox is mixed with the DNA to form a DNA-Dox pair by DNA intercalation. Then, the DNA-Dox pair is mixed with HerPBK10 to form HerDox by electrophilic interaction. To separate DNA-Dox from free Dox, the mixture underwent ultrafiltration centrifugation. The inventors found that >95% of the Dox added to the DNA did not release from the DNA during the ultrafiltration spin, indicating high retention of the drug even during a high speed spin (FIG. 4-A). The absorbance spectra of retentate and filtrate from this spin confirm that the absorbance maximum of retentate coincides with unfiltered Dox, whereas no such absorbance is detectable in the filtrate (FIG. 4 (B)). The retentate was then incubated with HerPBK10 and the resulting HerDox complex was separated from free components by high performance liquid chromatography (HPLC) size exclusion separation. Here the inventors show that the Dox absorbance mostly co-eluted with HerPBK10 (FIG. 5), as confirmed by SDS-PAGE of elution fractions (FIG. 5).

Example 3: HerDox is Highly Stable During Storage and in Serum

The inventors tested the stability of HerDox over 12 days under different storage temperatures: 40° C., room temperature, or 37° C. On each day, a sample underwent ultrafiltration, then filtrates and retentates were measured to determine whether any Dox was released from the complex. At 4° C., 100% of the product remained intact up to 12 days, and, interestingly, room temperature and 37° C. appeared to enhance the incorporation of the drug into the HerDox product (FIGS. 6-A and 6-B). Altogether, these findings suggest that HerDox remains stable and does not release Dox after prolonged storage under different temperatures. The inventors also examined HerDox stability in serum-containing media at 37° C. HerDox immobilized on nickel sepharose (via the HerPBK10 histidine tag) was incubated at 37° C. in complete (i.e. 10% fetal bovine serum-containing) media (to mimic tissue culture conditions) for different time periods before the beads were pelleted and supernatants measured for Dox release. Dox retention in the conjugate was also assessed by eluting the conjugate from the beads at each time point. The inventors observed that the serum produced no significant release of Dox from the conjugate, which would be detected by an increase in Dox filtrate absorbance in the '(+) serum' samples (FIG. 6-B, upper panel), and that the Dox was completely retained by the conjugate at each time point (FIG. 6-B, lower panel).

Example 4: HerDox Produces Targeted Toxicity Whereas Dox Alone does not

The inventors compared the effect of HerDox or Dox alone at equivalent dosages (0.5 μM with respect to Dox concentration) on HER2+ and HER2− breast cancer cells in separate dishes. By three days, HerDox reduced HER2+ cell numbers by over 75% whereas HER2− cell survival was unaffected (FIG. 7). Equivalent concentrations of Dox alone reduced both HER2+ and HER2− cells by the same order of magnitude (FIG. 7). These findings emphasize the importance of targeting by showing that the untargeted drug affects nontarget (i.e. HER2−) cells. Importantly, the protein carrier, HerPBK10, alone at the equivalent concentration of protein in HerDox (0.1 μM) had no effect on either cell line (FIG. 7), including a lack of proliferation induction. To test receptor targeting, the inventors used free heregulin ligand (Her or eHRG) as a competitive inhibitor. The free ligand completely inhibited cell killing by HerDox (FIG. 8), showing that HerDox bound and entered cells via the heregulin receptors. As a final in vitro challenge, the inventors tested whether HerDox induces toxicity specifically to HER2+ cells in a mixed culture of HER2+ and HER2− breast cancer cells. To do this, the inventors produced a HER2− cell line tagged with green fluorescent protein (GFP) for cell identification in the mixed culture (FIG. 9-A). The inventors found that HerDox nearly completely reduced non-GFP (HER2+) cell proliferation whereas GFP (HER2−) cell growth was not altered (FIG. 9-B). Altogether, these findings indicate that HerDox has the capacity to preferentially target toxicity to HER2+ cells. Importantly, all of these experiments were performed in complete (i.e. serum-containing) media, thus indicating that HerDox targets cells despite the presence of serum proteins. Moreover, the preferential cell killing of HER2+ cells in a mixed culture of HER2+ and HER2− cells implies that after death and lysis of the target cells, the Dox released into those cells is incapable of continuing to induce toxicity to HER2− cells. To further confirm the stability of HerDox in cell culture, HerDox was recovered from culture media in separate experiments at indicated time points and electrophoresed on an agarose gel, which was then illuminated by UV to detect Dox and stained with Coomassie blue to detect HerPBK10 protein (FIG. 9-C). As the gel does not retain free Dox, loss of Dox fluorescence over time would indicate that the conjugate released Dox. In serum-containing media, no such loss from HerDox is detectable. In serum-free conditions, it would appear that Dox fluorescence decreased by 1 h, however Coomassie blue staining shows that the decreased fluorescence is due to less sample loaded into the gel lane. Co-migration of HerPBK10 bands further verified that the conjugates remained intact in the cell media. Together with the serum-stability assay described earlier, these findings show that the conjugate remains intact during extended incubation in cell culture (which routinely contains at least 10% serum).

Example 5: GFP-Her Provides an Index of In Vivo Targeting

To get a sense of the targeting ability of the ligand in vivo and establish an index of in vivo targeting, the inventors used a green fluorescent protein (GFP)-tagged ligand (GFP-Her. Importantly, this ligand is identical to the 'Her' domain of HerPBK10. They established HER2+ tumors in 6-8 week female nude mice via bilateral flank injections of MDA-MB-435 cells. When the tumors reached 250-300 mm3 (~3-4 weeks after tumor cell implant), 3 nmol of GFP-Her was injected via the tail vein. Mock injected mice received saline alone. Indicated tissues were harvested at 3.5 hour after injection and imaged for GFP using a Xenogen IVIS three-dimensional small-animal in vivo imaging system (Xenogen, Alameda, Calif.). Preferential accumulation of GFP fluorescence was detected in the tumors over the other tissues (FIG. 10). Low to negligible levels of fluorescence were detected in the liver and muscle, while GFP fluorescence was undetectable in the other tissues, including the heart (FIG. 10). Tissues from mock-treated animals showed no fluorescence.

Example 6: HerDox Targets HER2+ Breast Cancer Cells In Vivo

Dox emits a red fluorescence upon appropriate wavelength excitation, which is used to detect biodistribution after systemic delivery of HerDox. Mice bearing 4-week old tumors (~700-800 mm$^3$) received a single tail vein injection of Dox or HerDox (0.008 mg/mL with respect to Dox conc) and images of live mice captured in real time, or of organs/tissues harvested at three hours post-injection were acquired using a customized macro-illumination and detection system. Fluorescence was evident throughout the body at 10 min after HerDox injection, then quickly accumulated at the tumors by 20 min and remained detectable in the tumors up to 100 min after injection (FIG. 11 (A)). Tissues and tumors harvested at ~3 h after HerDox injection showed intense fluorescence in the tumors while substantially lower levels of fluorescence were detectable in the liver (FIG. 11 (B)). Some fluorescence was barely detectable in the kidneys while other tissues, including the heart, spleen, lungs, and skeletal muscle, did not exhibit any fluorescence. In contrast, tissues harvested from mice injected with the equivalent dose of Dox exhibited detectable fluorescence in the liver, tumor, and kidneys. Lower levels of fluorescence were also detectable in the lungs and skeletal muscle.

To assess in vivo tumor toxicity, mice bearing 3-4 week bilateral flank tumors began receiving daily tail vein injections of Dox or HerDox (0.004 mg/kg with respect to Dox cone), HerPBK10 alone (at equivalent protein concentration to HerDox) or saline for 7 consecutive days. Tumors were measured throughout tumor growth, beginning 2 weeks before tail vein injections, and show that while Dox slows tumor growth, HerDox essentially prevented tumor growth while HerPBK10 alone and saline had no effect (FIG. 12 (A)). No appreciable weight loss over time was observed in either treated or control mice (FIG. 12 (B)).

At 25 days following injections, tumors and organs were harvested and processed for histochemistry. It is established that Dox can induce acute and long-term cardiotoxicity, therefore, the inventors examined the hearts of mice treated with HerDox or Dox. Hearts from Dox treated mice appeared slightly enlarged and dilated relative to the hearts from HerDox and saline-treated mice (not shown), suggestive of the dilated cardiomyopathy associated with Dox toxicity. Myocardia from saline-treated mice exhibited normal cardiac morphology, whereas the those from Dox-treated mice exhibited focal degeneration, myofibrillar loss, increased cytosoplasmic vacuolization, and nuclear condensation or dissolution, typifying Dox-induced cardiotoxicity, whereas the myocardium from HerDox-treated mice, showed similar morphology to the saline-treated mice (FIG. 12-C). In agreement with these findings, echocardiograms obtained to assess cardiac function in treated mice show signs of Dox-induced dysfunction that is not detectable in HerDox-treated mice: whereas Dox induces modest to marked reductions in stroke volume, cardiac output, and left ventricular internal dimension and volume, HerDox has no effect on these measurements and appeared similar to mock (saline)-treated mice (FIG. 12-D).

To assess the feasibility of measuring in vivo stability, the inventors incubated HerDox (at 0.12 mg/mL final Dox cone) or free Dox at equivalent concentration in freshly collected whole blood from mice and incubated the mixtures at 37° C. up to one hour. As the anticoagulant, 0.5 mM EDTA, was present in the blood collection, parallel samples were incubated at 37° C. in EDTA alone. Samples representing input HerDox (before incubation in blood) were incubated at 37° C. in HEPES-buffered saline. All samples were then centrifuged through 1 OK MW cutoff filters and Dox fluorescence measured in retentates and filtrates (SpectraMax M2 from Molecular Devices). The results show that there is no detectable loss of Dox from the conjugate, as evidenced by lack of detectable increase in filtrate fluorescence of Her-Dox, especially in comparison to the HerDox incubated in HBS or EDTA, or free Dox (FIG. 13). Likewise, there is no appreciable loss of Dox from HerDox retentates from samples incubated in blood compared to those incubated in saline or EDTA alone (FIG. 13). Taken together with the bioimaging results, these findings show that HerDox remains intact in blood and retains stability in vivo while in transit toward the tumor target.

Example 7: HerDox Mechanism: Dox Release in Cytoplasm & Accumulation in Nucleus

HerPBK10 alone does not induce cell death (FIG. 7), therefore it is the delivery of Dox into the cell that facilitates cell killing by HerDox. To understand the mechanism of HerDox-mediated tumor cell death, the inventors examined HER2+ cells microscopically after treatment with HerDox, using Dox fluorescence to detect intracellular location. Early after administration (at 0 min of uptake), HerDox appears mostly at the cell periphery, indicating that the conjugate is bound at the cell surface but not yet internalized (FIG. 14-A). In contrast, free Dox is already found inside the cell at the nuclear periphery (FIG. 14-A). At 60 min, when the majority of heregulin-targeted proteins have entered cells, Dox has accumulated in the nucleus, similar to free Dox (FIG. 14-A). These dynamics, in addition to earlier targeting results, support a receptor-mediated HerDox entry mechanism. Even the intranuclear pattern of Dox when delivered by HerPBK10 differs from free Dox. Whereas untargeted Dox accumulates in the cell nucleus, HerDox preferentially accumulates in nucleolar structures with some cytoplasmic fluorescence still visible (FIG. 14-B).

To determine whether Dox remains attached to HerPBK10 during uptake, the inventors used immuno-fluorescence against HerPBK10. At 15 min of uptake, HerPBK10 mostly colocalizes with Dox, suggesting that a substantial population of HerDox is still intact, though some nuclear accumulation of Dox is already visible (FIG. 15). At 30 and 60 min, increasing levels of Dox accumulate in the nucleus while the majority of HerPBK10 remains in the cytoplasm (FIG. 15). In fixed cells, nucleolar accumulation was not detectable as in the live cells (FIG. 14 (B)). Altogether, these findings show that HerPBK10 delivers Dox into the cell and releases the Dox intracellularly where it undergoes nuclear accumulation, consistent with the mechanism of delivery (FIG. 11-B).

Example 8: Human Serum has No Notable Effect on Cell Binding

To determine whether HerPBK10 competes with circulating ligand that may be present in serum, the inventors tested HerPBK10 binding to HER2+ breast cancer cells in human serum obtained from HER2+ patients. The Women's Cancer Research Institute at Cedars-Sinai occasionally acquires limited quantities of patient serum, of which sera from HER2+ patients comprises an even smaller minority. Notably, the human serum used here is the actual fraction of serum and associated proteins isolated from collected whole blood of HER2+ and age-matched HER2− patients. Earlier experiments demonstrate that HerDox binds cell targets in complete medium containing 10% bovine serum, and that this binding is competitively inhibited by excess free ligand. Here, the inventors replaced the bovine serum in the routine culturing media with the human serum obtained from the acquired patient samples to assess whether the human serum, especially from HER2+ patients, inhibits cell binding. The inventors ensured that cells received considerable exposure to the human sera (2 hours, which provides ample time for receptor binding of any circulating ligand) prior to treatment. Head-to-head comparisons of cell binding in serum from either HER2+ patients, HER2− patients, or bovine serum show no significant differences (FIG. 16), indicating that the human sera tested here did not interfere with HerPBK10 binding to target cells. Competitive inhibition with 100× heregulin ligand (+Her) confirms that the control binding activity is specific to heregulin receptors.

Example 9: HER Subunit Levels and Cy Toxicity on Proposed Cell Types

The inventors measured cell surface levels of HER subunits on various cell lines and types described herein, as previously described levels may not reflect the actual levels in the available cells used. The inventors acquired the indicated cell lines from ATCC and the NIH/NCI and profiled these with respect to HER subunit levels (FIG. 17 (A)). To assess whether HerDox induces toxicity in accordance to HER2 levels, the inventors selected lines displaying HER2 at relatively high (SKBR3), moderate (MDA-MB-435, MDA-MB-453, HeLa), and low to undetectable (MDA-MB-231) levels, and performed cytotoxicity dose curves. The inventors observed that HerDox LD50 inversely correlates with cell surface HER2 level on these selected lines: the cell line displaying relatively high HER2 shows a relatively higher sensitivity to HerDox whereas the cell line displaying low HER2 exhibits low sensitivity, and the lines displaying intermediate HER2 levels likewise exhibit intermediate sensitivities (FIG. 17 (B); CD50 is shown on a log scale).

Example 10

TABLE 1

| Cytotoxicity on cell lines | | |
|---|---|---|
| CELL LINE | HER2* | EC50** (µM HerDox) |
| MDA-MB-231 | 0.06 ± 0.006 | 7.2e5 ± 0.11 |
| MDA-MB-435 | 0.52 ± 0.08 | 0.74 ± 0.07 |
| T47D | 1.03 ± 0.26 | 0.64 ± 0.04 |
| SKOV3 | 1.79 ± 0.19 | 0.18 ± 0.03 |

*Relative cell surface level (mean ± 1 SD) as determined ELISA. N = 3 wells.
**Concentration (mean ± 1SD) yielding 50% reduction in cell survival, as determined by nonlinear regression analyses of HerDox dose curves. N = 3 treated wells per dose.

Example 11: Optimization of HerPBK10

As the HerPBK10 protein originates from the adenovirus penton base protein, whose natural binding targets are alpha-v integrins, the inventors assessed whether mutation of the Arg-Gly-Asp (RGD) integrin binding motif improves the capacity of the protein to deliver cargo into cells. While previous studies indicate that appendage of the heregulin receptor binding ligand to the penton base redirects it nearly exclusively to heregulin receptors (as demonstrated by competitive inhibition assay), it is possible that HerPBK10 may still co-opt integrin receptors that may redirect the protein to a different intracellular route or compete for binding sites on the protein itself. Rendering the RGD motif to EGD by point mutation disables integrin binding. Therefore, the mutant protein, HerPBrgdK10 was produced bearing this mutation, and tested for gene delivery in comparison to parental HerPBK10. At equivalent protein concentrations, HerPBrgdK10 exhibited moderate (~1.8-fold) to dramatic (~18- fold) enhancement of gene transfer (FIG. 18), which may be reflective of enhanced receptor binding or post-binding activities.

Example 12: DNA Constructs

The inventors used a common 5' oligonucleotide primer containing the sequence 5'-ATCGAAGGATCCATGCG-GCGCGCGGCGATGTAT-3' to amplify both wild-type and lysine-tagged penton sequences from a pJM1 7 adenoviral genome template. The sequences of the 3' primers are PB: 5'-GCATCAGAATTCTCAAAAAGTGCGGCTCGATAG-3' (SEQ ID NO:1) and PBK10 5'-CATGAATTCA(TTT)$_{10}$AAAAGTGCGGCTCGATAGGA-3' (SEQ ID NO:2). A BamHI restriction site was introduced in the 5' primer and an EcoR1 restriction site was introduced in the 3' primers for in-frame insertion of both the wild-type and lysine-tagged pentons into the pRSET-A bacterial expression plasmid (Invitrogen, Carlsbad, Calif., USA). This plasmid expresses the recombinant protein as an N-terminally histidine-tagged fusion for affinity purification by nickel chelate affinity chromatography.

Polymerase chain reaction (PCR) amplification was used to add a sequence encoding a short polyglycine linker to the amino (N)-terminus of PBK10. The sequence encoding the linker contains a 5OcII restriction site for additional cloning. The heregulin targeting ligand was produced by PCR amplification of the epidermal growth factor (EGF)-like domain of the heregulin gene29 using a 5' oligonucleotide primer containing a BamHI site and a 3' primer containing a SacU site for cloning in-frame with PBK10. The targeting ligand was added to the lysine-tagged construct to create Her-PBK10 by ligating the PCR product just N-terminal to PBK10. Construction of Her and GFP-Her have been previously described (Medina-Kauwe L. K., et al, BioTechniques 2000, 29: 602-609). HerK10 was created by PCR amplification of the Her construct using a 5' Her primer (Medina-Kauwe L. K., et al, BioTechniques 2000, 29: 602-609) and a 3' oligonucleotide primer containing the sequence 5'-ATGAATTCA(TTT)$_{10}$AGATCTACTTCCAC-CACTTCCACC-3' (SEQ ID NO:3).

Example 13: DS-Oligo Length does not Affect Dox Incorporation into the Targeted Complex Ds-oligo duplexes were formed from complimentary 30 bp sequences, LLAA-5 (SEQ ID NO:6) and LLAA-3 (SEQ ID NO:7) or 48 bp sequences, BglIIHis-5 (SEQ ID NO:8) and BglIIHis-3 (SEQ ID NO:9). Dox was added to each set of annealed duplexes at either 1:10, 1:20, or 1:40 molar ratio duplex:Dox (at a final Dox concentration of either 20, 40, or 80 μM) in 10 mM Tris/HCl buffer, pH 8.0, for 30 minutes at room temperature. The mixtures were then centrifuged through ultrafiltration membranes (Microcon Ultracel YMIO; Millipore) at 10,000×g to separate free Dox from incorporated Dox. Retentates and filtrates were collected separately, and absorbances of each measured at 480 nm using a SpectraMax M2 plate reader (Molecular Devices). The results (FIG. 19) show that there is no appreciable difference in Dox incorporation using either 30 or 48 bp duplexes.

Example 14: HerDox is Toxic to Glioma Cells

U251 human glioma cells were assessed for HER subunit levels by non-permeabilizing immunohistochemistry and found to display relatively marked levels of cell surface HER2, HER3, and HER4 (FIG. 20 (A)).

U251 cells growing in dishes were incubated with either HerDox or Dox (at either 0.5 μM or 1 μM) in the culture medium for 4 hours at 37° C., 5% $CO_2$, after which fresh complete medium was added to increase the final culture volume approximately four-fold, and the cells maintained at 37° C., 5% $CO_2$ for four days. Cells were trypsinized and counted on the last day.

The inventors' results show that HerDox exhibits 8-10 times more toxicity to U251 cells than the equivalent concentration of Dox, and likewise 10× less HerDox elicits the same toxicity as Dox (FIG. 20 (B)).

Example 15: Testing the Optimized Complex Comprised of a Modified Capsid Protein, Ds-Oligo, and DNA Intercalator for Targeting and Therapeutic Efficacy to HER2+ Tumors In Vivo Resistant Tumor Cells Display Elevated HER3 and Augmented Sensitivity to HerDox.

HER2+ breast cancer cell lines with acquired resistance to trastuzumab displayed elevated cell surface levels of HER3 in comparison to parental lines (BT474 and SKBR3) (FIG. 21-A), in agreement with studies elsewhere showing that HER3 elevation is associated with drug resistance. HerDox treatment was compared with trastuzumab and Trastuzumab+Pertuzumab combination therapy on BT474 and SKBR3 parental and trastuzumab-resistant lines in culture. Each therapeutic was administered at concentration ranges previously established for eliciting therapeutic efficacy. Trastuzumab (Tz) reduced parental BT474 cell survival by 50% and addition of pertuzumab (Pz) did not significantly increase cell death (FIG. 21B). Both regimens were ineffective on the BT474 resistant cells. HerDox showed higher cell death compared to Tz and Tz+Pz on BT474 parental cells, and completely killed off the BT474 resistant cells. The findings on SKBR3 were similar, as both parental and resistant cells showed little response to either Tz alone or combination therapy (Tz+Pz) (FIG. 21B). In contrast, HerDox elicited 50% cell death to the parental SKBR3, and >80% cell death on SKBR3 resistant cells.

The efficacy of HerDox was also examined on a cell line with pre-existing resistance. The JIMT-1 cell line was derived from a tumor that never responded to trastuzumab treatment. These cells remained unresponsive to Tz and Tz+Pz over a broad concentration range (FIG. 21-C). In contrast, HerDox yielded dose-dependent cell death and killed up to 90% of the cells (FIG. 21-C). Additionally, systemic delivery of HerDox to mice bearing JIMT-1 tumors ablated tumor growth in contrast to Tz and Dox alone (FIG. 22).

Trastuzumab Pre-Treatment Sensitizes HER2+ Cells to HerDox.

Previous studies have shown that HER3 is transcriptionally and translationally elevated as soon as 4 hours after HER2 inhibition, either by lapatinib or gene silencing. The enhanced efficacy of HerDox on Tz-resistant cells over parental cells suggests that trastuzumab may act as an adjuvant for HerDox, inducing HER3 elevation to increase homing of HerDox to resistant cells. To test this, parental and resistant lines were pretreated with trastuzumab for 4 or 24 hours before HerDox treatment. HerDox already exhibited improved cell killing compared to trastuzumab on parental SKBR3 cells, while pre-treatment augmented toxicity 40-50% further at the highest doses tested (FIG. 23A). HerDox toxicity on parental BT474 cells was modestly improved over trastuzumab but a 4 h pre-treatment with trastuzumab enhanced HerDox toxicity 50% more, and a 24 h pre-treatment enabled nearly 75% enhancement in toxicity (FIG. 23B). Even HER2-3-expressing MDA-MB-435 cells, which are already sensitive to HerDox, showed a modest enhancement in toxicity upon 24 h pre-treatment with trastuzumab (FIG. 23C). The Tz-resistant lines, on the other hand, already exhibited potent sensitivity to HerDox and thus pre-treatment was for the most part unnecessary (FIG. 23D-F). The Tz-resistant BT474 cells in particular underwent complete cell death at all HerDox concentrations tested (FIG. 23E). Accordingly, HerDox concentrations were reduced to assess whether trastuzumab pre-treatment would have any effect. Five-fold lower HerDox concentrations still had a potent effect on cell survival, and trastuzumab pre-treatment further enhanced cytotoxicity (FIG. 23F). Altogether, these findings suggest that trastuzumab may act as a useful adjuvant for HerDox treatment.

Example 16: HerPBK10 is Specific to HER3

FIG. 26 illustrates that HerPBK10 is specific to HER3 because HerPBK10 binds to an immobilized peptide containing the extracellular domain of human HER3, which was inhibited by pre-adsorption of HerPBK10 with free HER3 peptide in vitro (FIG. 26-A). The same pre-adsorption also inhibited HerPBK10 binding to HER2+ cells in culture (FIG. 26-B). Importantly, dimerization of HER2 with HER3 is not required for HerPBK10 binding, as the heterodimer-blocking antibody, pertuzumab (Pz), did not prevent HerPBK10 binding to its receptor on HER2+ cells (FIG. 26-B). Binding was also not inhibited by a HER4 peptide or betacellulin (which blocks HER4) (FIG. 26-B).

Example 17: Receptor Binding is not Inhibited by Patient Sera

Sera from five HER2+ patients and age-matched controls did not prevent HerPBK10 binding to HER2+ cells in culture and showed no significant differences between one another. Therefore, receptor binding is not inhibited by patient sera. Repeat dosing of HerPBK10 at therapeutic and 10-fold higher levels in immunocompetent mice did not yield detectable neutralizing antibody formation against the protein.

Example 18: Resistant Tumor Cells Display Elevated HER3 and Augmented Sensitivity to HerDox FIG. 27 (A) illustrates that HER2+ breast cancer cell lines with acquired resistance to trastuzumab (using standard regimens of long-term culture with increasing concentrations of HER2 inhibitor) display elevated cell surface levels of HER3 in comparison to parental lines (BT474 and SKBR3). This result is consistent with knowledge known in the art that HER3 elevation is associated with drug resistance.

The effect on cancer cells of HerDox was compared with (i) trastuzumab, and (ii) combination therapy of trastuzumab (Tz) and pertuzumab (Pz). The experiment was performed on BT474 and SKBR3 parental and trastuzumab-resistant cell lines in culture. Each therapeutic was administered at concentration ranges previously established or known in the art for eliciting therapeutic efficacy. Tz reduced parental BT474 cell survival by 50%; addition of Pz did not significantly increase cell death (FIG. 27-B). Both regimens were ineffective on the BT474 resistant cells. On the other hand, HerDox showed higher cell death compared to Tz and Tz+Pz on BT474 parental cells, and effectively eliminated the BT474 resistant cells.

Similar results were also obtained for the SKBR3 cell line. Both parental and resistant cells showed little response to either Tz alone or combination therapy (Tz+Pz) (FIG. 27-B). In contrast, HerDox elicited 50% parental SKBR3 cell death, and >80% cell death on SKBR3 resistant cells. Therefore, these results show that resistant tumor cells display augmented sensitivity to HerDox.

The contribution of HER3 to targeted toxicity was evaluated by assessing whether pre-adsorbing HerDox with a peptide comprising the ligand-binding domain of HER3 blocked cytotoxicity. Whereas HerDox elicited significant cell death on parental and resistant lines, this was inhibited by the HER3 peptide (FIG. 27-C), indicating that cell death occurred through ligand-directed delivery of the Dox payload. FIG. 27 (E) shows the efficacy of HerDox on a cell line with pre-existing resistance. The JIMT-1 cell line was derived from a HER2+ tumor that never responded to trastuzumab treatment. These cells remained unresponsive to Tz and Tz+Pz, and only partially responsive to Dox, over a broad concentration range. In contrast, HerDox yielded dose-dependent cell death and eliminated up to 90% of the cells (FIG. 27-E). Finally, systemic delivery of HerDox to mice bearing JIMT-1 tumors ablated tumor growth in contrast to Tz and Dox alone, at the same drug dose as HerDox (0.004 mg Dox/kg/injection). In fact, the impact of Tz or Dox alone on tumor growth is only slight compared to a mock saline treatment (FIG. 28). Therefore, these results show that HerDox elicit significant cell death on resistant tumor cells.

Example 19: Trastuzumab Sensitizes HER2+ Cells to HerDox

FIG. 29 (A) shows that Tz pre-treatment in vitro elevates HER3 in parental cells (FIG. 29-A), augments HerPBK10 binding to these cells (FIG. 29-B), and enhances HerDox toxicity to these cells (FIG. 29-C, 29-D). The parental and resistant cell lines were pretreated with Tz for 4 or 24 hours before HerDox treatment. HerDox already exhibited improved cell killing compared to Tz on parental SKBR3 cells, while pre-treatment augmented toxicity 40-50% further at the highest doses tested (FIG. 29-C). The enhanced efficacy of HerDox on Tz-resistant cells over parental cells shows that trastuzumab acts as an adjuvant for HerDox, inducing HER3 elevation to increase homing of HerDox to resistant cells.

HerDox toxicity on parental BT474 cells was modestly improved over Tz but a four hour pre-treatment with trastuzumab enhanced HerDox toxicity 50% more, and a 24 hour pre-treatment enabled nearly 75% enhancement in toxicity (FIG. 29-D). Even HER2-3-expressing MDA-MB-435 cells, which are already sensitive to HerDox, showed a modest enhancement in toxicity upon 24 hour pre-treatment with Tz (FIG. 29-E). The Tz-resistant lines, on the other hand, already exhibited potent sensitivity to HerDox and thus pre-treatment was for the most part unnecessary (FIG. 29-F, 29-G). The Tz-resistant BT474 cells in particular underwent complete cell death at all HerDox concentrations tested (FIG. 29-G). Accordingly, HerDox concentrations were reduced to assess whether trastuzumab pre-treatment would have any effect. Five-fold lower HerDox concentrations still had a potent effect on cell survival, and Tz pre-treatment further enhanced cytotoxicity (FIG. 29-H).

Altogether, these findings demonstrate that Tz acts as a useful adjuvant for HerDox treatment. Similarly, pertuzumab, lapatinib, T-DM1, also acts as an adjuvant for HerDox treatment.

Example 20: HerPBK10 Uptake is More Rapid and Efficient Compared to Trastuzumab Fluorescently-labeled HerPBK10 was prepared to assess its bio-distribution and cell uptake in comparison to labeled Tz. Equivalent doses of each reagent were injected into the tail veins of HER2+ tumor bearing mice. Tissues were harvested at four hours after injection for imaging. Both reagents were compared to a labeled non-targeted protein, BSA. HerPBK10 and Tz showed equivalent levels of tumor accumulation (which were both higher than BSA), and nearly absent delivery to the heart, spleen, and muscle (FIG. 30-A). However, delivery to other non-tumor tissue, such as, liver, lung, and kidney, was higher for Tz than HerPBK10. In contrast to Tz, HerPBK10 showed no lung delivery (FIG. 30-A).

The uptake in HER2+ MDA-MB-435 cells were also evaluated. The cell surface receptor levels in these cells are shown by the graph in FIG. 30-B. HerPBK10 exhibited cell surface clustering followed by significant endocytosis within 45 min after cell uptake (FIG. 30-B). In contrast, despite the elevated HER2 levels in comparison to HER3 on these cells, Tz exhibited sparse binding on the cell surface that remained in sparsely punctate areas on the cells up to two hours after cell binding (FIG. 30-B).

These results show that HerPBK10 uptake is more rapid and efficient compared to Tz.

Example 21: HerPBK10 Exhibits Higher Binding than Trastuzumab on Patient Tumor Tissue Expressing Elevated HER3 Over HER2

To determine whether the nanoparticles described in this application are capable of recognizing HER3 on human tissue, breast tumor tissue was obtained from a surgical specimen of a HER2+ patient. The tissue was examined to determine whether HerPBK10 binds this tissue via HER3. FIG. 31 shows that HerPBK10 and Tz both exhibit concentration-dependent binding to disaggregated cells from this tumor sample, with HerPBK10 exhibiting greater binding than Tz (FIG. 31-B). This binding curve correlated with the elevated HER3 and very low HER2 that was measured on the tumor cell surface (FIG. 31-A).

Example 22: HerPBK10 Recognizes Mouse HER3

Mouse 4T1 cells, obtained from a BALB/c mouse mammary tumor, are triple-negative and have been used as a syngeneic TNBC model in BALB/c mice. HER3 is expressed on the cell surface of 4T1 at significant levels (FIG. 32-B), is recognized by HerPBK10 (FIG. 32-C), and is competitively inhibited by human HER3 peptide (FIG. 32-C). The receptor-specific binding of HerPBK10 to mouse HER3 reflects the high level of amino acid sequence identity between mouse and human HER3: 91% identity for the entire protein and 94% in the heregulin-binding region (extracellular domains I and II) (FIG. 32-A). These findings show that the BALB/c-4T1 model can be used to test targeting in an immunocompetent setting. In addition, the recognition of mouse HER3 by HerPBK10 raises the clinical relevance of our existing findings in xenograft models: HerDox shows preferential tumor-targeted toxicity even when it recognizes endogenous HER3 in mice. Importantly, human BT-549 cells, which are also derived from a TNBC, display elevated HER3 on the cell surface (FIG. 32-B) and provide an additional TNBC cell line to target.

Example 23: The Penton Base Domain is Required for Penetration into the Cytosol Deletion mutants of HerPBK10, lacking the PB domain, failed to deliver S2Ga into the cytoplasm of a cell. This verifies that the penton base domain of HerPBK10 is required for endosomal membrane penetration after receptor-mediated uptake.

Example 24: Intracellular Trafficking Mutants Generated by Directed Evolution Directed evolution and phage display biopanning were applied to isolate protein variants of the penton base domain with potentially augmented intracellular trafficking activities. This technique entailed random mutagenesis of the recombinant penton base gene, expression of the resulting mutant library on T7 bacteriophage, and screening of the phage library on HeLa cells (which endocytoses the penton base) in culture. The "selective pressure" applied to the screen consisted of isolating mutants that exhibited augmented cytosolic and/or nuclear partitioning, showing that the protein has facilitated full penetration into the cell, and trafficking to the desired subcellular compartment (FIG. 35-A). Several truncated and full-length variants were isolated with point mutations that were cloned into HerPBK10, replacing the penton base domain (FIG. 35-B). Two of these full-length mutants (111C and 333F) show enhanced partitioning to cytosolic, cytoskeletal, and nuclear compartments in comparison to the parental protein (wt HerPBK10) (FIG. 35-C), while the truncated variants (i.e. TM) could not escape endosomes (FIG. 35-D).

Example 25: S2Ga Interacts with TSPO

Studies probing the mechanism of corrole toxicity revealed that HerGa causes superoxide-mediated damage to the cytoskeleton as well as mitochondrial membrane permeability, leading to apoptotic death. FIGS. 36-A and 36-B show that S2Ga directly binds the mitochondrial outer membrane protein, TSPO (FIG. 36A-B). TSPO translocates porphyrins and other metabolites into mitochondria for processing as well as interacts with components of the mitochondrial permeability transition pore complex, and is critical for cellular homeostasis, as knock-outs of TSPO are embryonic lethal in mice. S2Ga specifically recognizes the porphyrin-binding site on TSPO (FIG. 36A-B), as S2Ga binding is competitively inhibited by PK11195, which inhibits porphyrin binding to TSPO. Overexpression of recombinant soluble TSPO in MDA-MB-435 cells prevents HerGa-mediated disruption of mitochondrial membrane potential (FIG. 36C-D), demonstrating that HerGa interacts with TSPO in situ.

Example 26: HerMn Enables Targeted Toxicity and MR Detection

Whereas the fluorescence attributes of HerGa established the use of corroles as imaging agents, the clinical applicability of optical imaging is constrained by the limited penetration depth of the excitation wavelength and re-emitted wavelength. Accordingly, alternative metallated corroles were used that, when combined with HerPBK10, are as cytotoxic as HerGa but bear sufficient contrast properties to enable detection using clinically relevant modalities such as magnetic resonance imaging (MRI). HerMn exhibits targeted toxicity to HER2+ but not HER2− tumor cells in culture while S2Mn has no effect on cell survival (FIG. 37). HerMn collapses mitochondrial membrane potential (FIG. 38-A) and the cytoskeleton through superoxide elevation (FIG. 38-B). HerMn homes to tumors in vivo after systemic delivery, bypassing most normal tissue including the heart (FIG. 39), and ablates tumor growth at very low pharmacologic dose (0.008 mg/kg), in contrast to free S2Mn, HerPBK10 alone or saline treatment (FIG. 40-A). In solution, HerMn particles exhibit limited T1 (spin-lattice) relaxation shortening compared to free S2Mn (FIG. 41-A), suggesting that encapsulation in the protein particle prevents access to water molecules. However, delivery of HerMn in vivo yields marked T1 relaxation reduction and MRI contrast enhancement in tumors, including in comparison to free S2Mn and Gd (FIG. 40-B), suggesting that the corrole is released from the particle after tissue uptake. The prolonged retention of corroles in tumor tissue shows that HerMn may serve as a longer lasting contrast agent compared to the rapid clearance of Gd.

Example 27: HerGa and HerMn are Non-Toxic to Human Cardiosphere-Derived Cells (CDCs)

To assess translatability, the viability of human cardiosphere-derived cells (CDCs) in the presence of HerGa and/or HerMn was examined. Escalating concentrations of HerGa, HerMn and individual components (HerPBK10 alone, S2Ga alone and S2Mn alone) have no detectable effect on CDC viability in contrast to Dox (FIG. 40-B), which has known cardiotoxicity.

Example 28: Resistant Tumor Cells Display Elevated HER3 and Augmented Binding to HerPBK10

HER2+ breast cancer cell lines with acquired resistance to Tz (using standard regimens of long-term culture with increasing concentrations of HER2 inhibitor) displayed elevated cell surface levels of HER3 in comparison to parental lines (BT474 and SKBR3) (FIG. 42-A, 43-A), in agreement with knowledge in the art that HER3 elevation is associated with drug resistance. The JIMT-1 breast cancer line, which was derived from a HER2+ tumor that never responded to Tz treatment, also exhibited elevated HER3 in comparison to HER2 (FIG. 42-B). HER3 was transcriptionally and translationally elevated as soon as four hours after HER2 inhibition, either by Lp or gene silencing. Parental lines were exposed to Tz for 24 hours and then measured cell surface HER3 levels in comparison to non-treated parental cells. Not only did Tz-treatment yield elevated HER3 levels but HerPBK10 binding to these cells was proportionately increased (FIG. 42-C, 42-D). As a means of evaluating whether the nanoparticles described herein are capable of recognizing HER3 on human tissue, breast tumor tissue was obtained from a surgical specimen of a HER2+ patient and examined whether HerPBK10 could bind this tissue via HER3. It was found that HerPBK10 and Tz both exhibited concentration-dependent binding to disaggregated cells from this tumor sample, with HerPBK10 showing greater binding than Tz (FIG. 42-F). This binding curve correlated with the elevated HER3 and very low HER2 that was measured on the tumor cell surface (FIG. 42-E).

Example 29: HerGa Exhibits Enhanced Toxicity to Tz-Resistant Tumor Cells In Vitro and In Vivo The effectiveness of HerGa to Tz and combination therapy (Tz+Pz) was compared on BT474 parental and Tz-resistant lines. Each therapeutic was administered at concentration ranges known in the art for eliciting therapeutic efficacy. Tz reduced parental BT474 cell survival by 50% (FIG. 42-B) and addition of Pz did not significantly increase cell death (FIG. 43-C). HerGa exhibited similar results on parental cells (FIG. 43-B, 43-C). Tz and Tz+Pz were ineffective on the BT474 resistant cells (FIG. 43-B, 43-C). In contrast, HerGa completely eliminated the BT474 resistant cells (FIG. 43-B). The findings on Tz+Lp-resistant BT474 cells were similar, in that Tz displayed no efficacy whereas HerGa elicited nearly complete cell death.

Systemic delivery of HerGa (0.008 mg/kg/injection) to mice bearing BT474 Tz-resistant tumors ablated tumor growth in contrast to S2Ga and HerPBK10 alone (FIG. 43-D). As these mice were not provided a maintenance dosing of Tz to sustain resistance, sensitivity to Tz appeared to return in vivo but these tumors eventually became resistant to Tz treatment and started to grow in size despite therapeutic doses of Tz (FIG. 43-E). Intra venous delivery of HerGa to these mice reduced these tumors in size (FIG. 43-E).

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating a triple-negative breast cancer in a patient comprising:
   administering to the patient a therapeutically effective amount of a drug delivery molecule comprising:
   (a) a polypeptide comprising a receptor binding domain of human heregulin-α; an adenovirus penton base protein; and a positively charged domain comprising a plurality of positively-charged amino acid residues that provide a net positive charge to the positively charged domain;
   (b) a double-stranded nucleic acid molecule bound to the positively charged domain via electrostatic interactions; and
   (c) a chemotherapeutic agent non-covalently linked to the double-stranded nucleic acid molecule;
   wherein the triple-negative breast cancer expresses HER3.

2. The method of claim 1, wherein the positively charged domain comprises a polylysine motif, and wherein the polylysine motif comprises a plurality of contiguous lysines.

3. The method of claim 2, wherein the polylysine motif is a decalysine.

4. The method of claim 1, wherein the double-stranded nucleic acid molecule comprises a nucleic acid molecule with the sequence of SEQ ID NO:6, SEQ ID NO:7, SEQ ID NO:8, or SEQ ID NO:9.

5. The method of claim 1, wherein the polypeptide comprises from N-terminus to C-terminus:
   a heregulin-a binding domain comprising a sequence according to SEQ ID NO: 13;
   a penton base segment comprising a sequence according to SEQ ID NO: 10; and
   a decalysine.

6. The method of claim 1, wherein the chemotherapeutic agent is doxorubicin.

7. The method of claim 1, wherein the chemotherapeutic agent is intercalated with the double-stranded nucleic acid molecule.

8. The method of claim 1, wherein the patient is a human.

9. A method of inducing apoptosis in a triple-negative breast cancer cell comprising:
   contacting the triple-negative breast cancer cell with a drug delivery molecule comprising:
   (a) a polypeptide comprising a receptor binding domain of human heregulin-α; an adenovirus penton base protein; and a positively charged domain comprising a plurality of positively-charged amino acid residues that provide a net positive charge to the positively charged domain;

(b) a double-stranded nucleic acid molecule bound to the positively charged domain via electrostatic interactions; and (c) a chemotherapeutic agent non-covalently linked to the double-stranded nucleic acid molecule, wherein the chemotherapeutic agent is effective to induce apoptosis of the triple-negative breast cancer cell;

wherein the triple-negative breast cancer cell expresses HER3.

10. The method of claim 9, wherein the contacting is in vitro.

11. The method of claim 9, wherein the contacting is in vivo.

12. The method of claim 9, wherein the breast cancer cell is a human breast cancer cell.

13. The method of claim 9, wherein the double-stranded nucleic acid molecule comprises a nucleic acid molecule with the sequence of SEQ ID NO:6, SEQ ID NO:7, SEQ ID NO:8, or SEQ ID NO:9.

14. A method of killing a triple-negative breast cancer cell comprising:

contacting the triple-negative breast cancer cell with a drug delivery molecule comprising:

(a) a polypeptide comprising a receptor binding domain of human heregulin-a; an adenovirus penton base protein; and a positively charged domain comprising a plurality of positively-charged amino acid residues that provide a net positive charge to the positively charged domain;

(b) a double-stranded nucleic acid molecule bound to the positively charged domain via electrostatic interactions; and (c) a chemotherapeutic agent non-covalently linked to the double-stranded nucleic acid molecule;

wherein the triple-negative breast cancer cell expresses HER3.

* * * * *

SEQUENCE LISTING

```
<160> NUMBER OF SEQ ID NOS: 14

<210> SEQ ID NO 1
<211> LENGTH: 33
<212> TYPE: DNA
<213> ORGANISM: Homo sapiens

<400> SEQUENCE: 1
gcatcagaat tctcaaaaag tgcggctcga tag                             33

<210> SEQ ID NO 2
<211> LENGTH: 60
<212> TYPE: DNA
<213> ORGANISM: Homo sapiens

<400> SEQUENCE: 2
catgaattca tttttttttt tttttttttt tttttttttt aaaagtgcgg ctcgatagga    60

<210> SEQ ID NO 3
<211> LENGTH: 63
<212> TYPE: DNA
<213> ORGANISM: Homo sapiens

<400> SEQUENCE: 3
atgaattcat tttttttttt tttttttttt ttttttttta gatctacttc caccacttcc    60
acc                                                               63

<210> SEQ ID NO 4
<211> LENGTH: 2382
<212> TYPE: DNA
<213> ORGANISM: Homo sapiens

<400> SEQUENCE: 4
```

-continued

```
ttgcctcccc gattgaaaga gatgaaaagc caggaatcgg ctgcaggttc caaactagtc      60
cttcggtgtg aaaccagttc tgaatactcc tctctcagat tcaagtggtt caagaatggg     120
aatgaattga atcgaaaaaa caaaccacaa aatatcaaga tacaaaaaaa gccagggaag     180
tcagaacttc gcattaacaa agcatcactg gctgattctg gagagtatat gtgcaaagtg     240
atcagcaaat taggaaatga cagtgcctct gccaatatca ccatcgtgga atcaaacgag     300
atcatcactg gtatgccagc ctcaactgaa ggagcatatg tgtcttcaga gtctcccatt     360
agaatatcag tatccacaga aggagcaaat acttcttcat ctacatctac atccaccact     420
gggacaagcc atcttgtaaa atgtgcggag aaggagaaaa ctttctgtgt gaatggaggg     480
gagtgcttca tggtgaaaga cctttcaaac ccctcgagat acttgtgcaa gtgccaacct     540
ggattcactg gagcaagatg tactgagaat gtgcccatga agtccaaaa ccaagaaaag      600
gcggaggagc tgtacggtgg aagtggtgga agtggatcca tgcggcgcgc ggcgatgtat     660
gaggaaggtc ctcctcccte ctacgagagt gtggtgagcg cggcgccagt ggcggcggcg     720
ctgggttctc ccttcgatgc tcccctggac ccgccgtttg tgcctccgcg gtacctgcgg     780
cctaccgggg ggagaaacag catccgttac tctgagttgg caccccctatt cgacaccacc     840
cgtgtgtacc tggtggacaa caagtcaacg gatgtggcat ccctgaacta ccagaacgac     900
cacagcaact ttctgaccac ggtcattcaa acaatgact acagcccggg ggaggcaagc      960
acacagacca tcaatcttga cgaccggtcg cactggggcg cgacctgaa aaccatcctg     1020
cataccaaca tgccaaatgt gaacgagttc atgtttacca ataagtttaa ggcgcgggtg    1080
atggtgtcgc gcttgcctac taaggacaat caggtggagc tgaaatacga gtgggtggag    1140
ttcacgctgc ccgagggcaa ctactccgag accatgacca tagaccttat gaacaacgcg    1200
atcgtggagc actacttgaa agtgggcaga cagaacgggg ttctggaaag cgacatcggg    1260
gtaaagtttg acacccgcaa cttcagactg gggtttgacc ccgtcactgg tcttgtcatg    1320
cctggggtat atacaaacga agccttccat ccagacatca ttttgctgcc aggatgcggg    1380
gtggacttca cccacagccg cctgagcaac ttgttgggca tccgcaagcg gcaacccttc    1440
caggagggct ttaggatcac ctacgatgat ctggagggtg gtaacattcc cgcactgttg    1500
gatgtggacg cctaccaggc gagcttgaaa gatgacaccg aacagggcgg gggtggcgca    1560
ggcggcagca acagcagtgg cagcggcgcg aagagaact ccaacgcggc agccgcggca     1620
atgcagccgg tggaggacat gaacgatcat gccattcgcg gcgacacctt tgccacacgg    1680
gctgaggaga agcgcgctga ggccgaagca gcggccgaag ctgccgcccc cgctgcgcaa    1740
cccgaggtcg agaagcctca gaagaaaccg gtgatcaaac ccctgacaga ggacagcaag    1800
aaacgcagtt acaacctaat aagcaatgac agcaccttca cccagtaccg cagctggtac    1860
cttgcataca actacggcga ccctcagacc ggaatccgct catggaccct gctttgcact    1920
cctgacgtaa cctgcggctc ggagcaggtc tactggtcgt tgccagacat gatgcaagac    1980
cccgtgacct tccgctccac gcgccagatc agcaactttc cggtggtggg cgccgagctg    2040
ttgcccgtgc actccaagag cttctacaac gaccaggccg tctactccca actcatccgc    2100
cagtttacct ctctgaccca cgtgttcaat cgctttcccg agaaccagat tttggcgcgc    2160
ccgccagccc ccaccatcac caccgtcagt gaaaacgttc ctgctctcac agatcacggg    2220
acgctaccgc tgcgcaacag catcggagga gtccagcgag tgaccattac tgacgccaga    2280
cgccgcacct gccctacgt ttacaaggcc ctgggcatag tctcgccgcg cgtcctatcg     2340
agccgcactt ttaaaaaaaa aaaaaaaaa aaaaaaaaa aa                          2382
```

<210> SEQ ID NO 5
<211> LENGTH: 2382
<212> TYPE: DNA
<213> ORGANISM: Homo sapiens

<400> SEQUENCE: 5

| | | | | | |
|---|---|---|---|---|---|
| tttttttttt | tttttttttt | tttttttttt | aaaagtgcgg | ctcgatagga | cgcgcggcga | 60 |
| gactatgccc | agggccttgt | aaacgtaggg | gcaggtgcgg | cgtctggcgt | cagtaatggt | 120 |
| cactcgctgg | actcctccga | tgctgttgcg | cagcggtagc | gtcccgtgat | ctgtgagagc | 180 |
| aggaacgttt | tcactgacgg | tggtgatggt | ggggctggc | gggcgcgcca | aaatctggtt | 240 |
| ctcgggaaag | cgattgaaca | cgtgggtcag | agaggtaaac | tggcggatga | gttgggagta | 300 |
| gacgcctgg | tcgttgtaga | agctcttgga | gtgcacgggc | aacagctcgg | cgcccaccac | 360 |
| cggaaagttg | ctgatctggc | gcgtggagcg | gaaggtcacg | gggtcttgca | tcatgtctgg | 420 |
| caacgaccag | tagacctgct | ccgagccgca | ggttacgtca | ggagtgcaaa | gcagggtcca | 480 |
| tgagcggatt | ccggtctgag | ggtcgccgta | gttgtatgca | aggtaccagc | tgcggtactg | 540 |
| ggtgaaggtg | ctgtcattgc | ttattaggtt | gtaactgcgt | ttcttgctgt | cctctgtcag | 600 |
| gggtttgatc | accggtttct | tctgaggctt | ctcgacctcg | ggttgcgcag | cggggcggc | 660 |
| agcttcggcc | gctgcttcgg | cctcagcgcg | cttctcctca | gcccgtgtgg | caaaggtgtc | 720 |
| gccgcgaatg | gcatgatcgt | tcatgtcctc | caccggctgc | attgccgcgg | ctgccgcgtt | 780 |
| ggagttctct | tccgcgccgc | tgccactgct | gttgctgccg | cctgcgccac | ccccgccctg | 840 |
| ttcggtgtca | tctttcaagc | tcgcctggta | ggcgtccaca | tccaacagtg | cgggaatgtt | 900 |
| accaccctcc | agatcatcgt | aggtgatcct | aaagccctcc | tggaagggtt | gccgcttgcg | 960 |
| gatgcccaac | aagttgctca | gcggctgtg | ggtgaagtcc | accccgcatc | ctggcagcaa | 1020 |
| aatgatgtct | ggatggaagg | cttcgtttgt | atataccccca | ggcatgacaa | gaccagtgac | 1080 |
| ggggtcaaac | cccagtctga | agttgcgggt | gtcaaacttt | accccgatgt | cgcttttccag | 1140 |
| aaccccgttc | tgtctgccca | ctttcaagta | gtgctccacg | atcgcgttgt | tcataaggtc | 1200 |
| tatggtcatg | gtctcggagt | agttgccctc | gggcagcgtg | aactccaccc | actcgtattt | 1260 |
| cagctccacc | tgattgtcct | tagtaggcaa | gcgcgacacc | atcacccgcg | ccttaaactt | 1320 |
| attggtaaac | atgaactcgt | tcacatttgg | catgttggta | tgcaggatgg | ttttcaggtc | 1380 |
| gccgccccag | tgcgaccggt | cgtcaagatt | gatggtctgt | gtgcttgcct | ccccccgggct | 1440 |
| gtagtcattg | ttttgaatga | ccgtggtcag | aaagttgctg | tggtcgttct | ggtagttcag | 1500 |
| ggatgccaca | tccgttgact | tgttgtccac | caggtacaca | cgggtggtgt | cgaataggg | 1560 |
| tgccaactca | gagtaacgga | tgctgttttct | ccccccggta | ggccgcaggt | accgcggagg | 1620 |
| cacaaacggc | gggtccaggg | gagcatcgaa | gggagaaccc | agcgccgccg | ccactggcgc | 1680 |
| cgcgctcacc | acactctcgt | aggagggagg | aggaccttcc | tcatacatcg | ccgcgcgccg | 1740 |
| catggatcca | cttccaccac | ttccaccgta | cagctcctcc | gccttttctt | ggttttggac | 1800 |
| tttcatgggc | acattctcag | tacatcttgc | tccagtgaat | ccaggttggc | acttgcacaa | 1860 |
| gtatctcgag | gggtttgaaa | ggtctttcac | catgaagcac | tcccctccat | tcacacagaa | 1920 |
| agttttctcc | ttctccgcac | attttacaag | atggcttgtc | ccagtggtgg | atgtagatgt | 1980 |
| agatgaagaa | gtatttgctc | cttctgtgga | tactgatatt | ctaatgggag | actctgaaga | 2040 |
| cacatatgct | ccttcagttg | aggctggcat | accagtgatg | atctcgtttg | attccacgat | 2100 |

```
ggtgatattg gcagaggcac tgtcatttcc taatttgctg atcactttgc acatatactc    2160
tccagaatca gccagtgatg ctttgttaat gcgaagttct gacttccctg gcttttttg     2220 tatcttgata ttttgtggtt tgttttttcg attcaattca ttcccattct tgaaccactt    2280
gaatctgaga gaggagtatt cagaactggt tcacaccga aggactagtt tggaacctgc     2340
agccgattcc tggcttttca tctctttcaa tcggggaggc aa                       2382
```

```
<210> SEQ ID NO 6
<211> LENGTH: 30
<212> TYPE: DNA
<213> ORGANISM: Homo sapiens

<400> SEQUENCE: 6
cgcctgagca acgcggcggg catccgcaag                                      30

<210> SEQ ID NO 7
<211> LENGTH: 30
<212> TYPE: DNA
<213> ORGANISM: Homo sapiens

<400> SEQUENCE: 7
cttgcggatg cccgccgcgt tgctcaggcg                                      30

<210> SEQ ID NO 8
<211> LENGTH: 48
<212> TYPE: DNA
<213> ORGANISM: Homo sapiens

<400> SEQUENCE: 8
gactacagat ctcatcatca tcatcatcat gagctcaagc aggaattc                  48

<210> SEQ ID NO 9
<211> LENGTH: 48
<212> TYPE: DNA
<213> ORGANISM: Homo sapiens

<400> SEQUENCE: 9
gaattcctgc ttgagctcat gatgatgatg atgatgagat ctgtagtc                  48

<210> SEQ ID NO 10
<211> LENGTH: 571
<212> TYPE: PRT
<213> ORGANISM: Homo sapiens

<400> SEQUENCE: 10
```

```
Met Arg Arg Ala Ala Met Tyr Glu Glu Gly Pro Pro Ser Tyr Glu
1               5                  10                  15

Ser Val Val Ser Ala Ala Pro Val Ala Ala Leu Gly Ser Pro Phe
            20                  25                  30

Asp Ala Pro Leu Asp Pro Pro Phe Val Pro Pro Arg Tyr Leu Arg Pro
        35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
            100                 105                 110
```

-continued

Leu Asp Asp Arg Ser His Trp Gly Gly Asp Leu Lys Thr Ile Leu His
            115                 120                 125

Thr Asn Met Pro Asn Val Asn Glu Phe Met Phe Thr Asn Lys Phe Lys
130                 135                 140

Ala Arg Val Met Val Ser Arg Leu Pro Thr Lys Asp Asn Gln Val Glu
145                 150                 155                 160

Leu Lys Tyr Glu Trp Val Glu Phe Thr Leu Pro Gly Asn Tyr Ser
            165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
            195                 200                 205

Lys Phe Asp Thr Arg Asn Phe Arg Leu Gly Phe Asp Pro Val Thr Gly
    210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
        275                 280                 285

Val Asp Ala Tyr Gln Ala Ser Leu Lys Asp Asp Thr Glu Gln Gly Gly
    290                 295                 300

Gly Gly Ala Gly Gly Ser Asn Ser Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
            355                 360                 365

Glu Val Glu Lys Pro Gln Lys Lys Pro Val Ile Lys Pro Leu Thr Glu
    370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
            420                 425                 430

Gly Ser Glu Gln Val Tyr Trp Ser Leu Pro Asp Met Met Gln Asp Pro
        435                 440                 445

Val Thr Phe Arg Ser Thr Arg Gln Ile Ser Asn Phe Pro Val Val Gly
    450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Pro Ala Pro Thr
            500                 505                 510

Ile Thr Thr Val Ser Glu Asn Val Pro Ala Leu Thr Asp His Gly Thr
        515                 520                 525

Leu Pro Leu Arg Asn Ser Ile Gly Gly Val Gln Arg Val Thr Ile Thr

```
                530                 535                 540
Asp Ala Arg Arg Arg Thr Cys Pro Tyr Val Tyr Lys Ala Leu Gly Ile
545                 550                 555                 560

Val Ser Pro Arg Val Leu Ser Ser Arg Thr Phe
                565                 570

<210> SEQ ID NO 11
<211> LENGTH: 10
<212> TYPE: PRT
<213> ORGANISM: Homo sapiens

<400> SEQUENCE: 11

Lys Lys Lys Lys Lys Lys Lys Lys Lys Lys
1               5                   10

<210> SEQ ID NO 12
<211> LENGTH: 33
<212> TYPE: DNA
<213> ORGANISM: Homo sapiens

<400> SEQUENCE: 12
atcgaaggat ccatgcggcg cgcggcgatg tat                              33

<210> SEQ ID NO 13
<211> LENGTH: 220
<212> TYPE: PRT
<213> ORGANISM: Homo sapiens

<400> SEQUENCE: 13

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln
    210                 215                 220
```

```
<210> SEQ ID NO 14
<211> LENGTH: 220
<212> TYPE: PRT
<213> ORGANISM: Mouse

<400> SEQUENCE: 14

Ser Glu Met Gly Asn Ser Gln Ala Val Cys Pro Gly Thr Leu Asn Gly
1               5                   10                  15

Leu Ser Val Thr Gly Asp Ala Asp Asn Gln Tyr Gln Thr Leu Tyr Lys
            20                  25                  30

Leu Tyr Glu Lys Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Val Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Phe Thr Gln Leu Thr Glu Ile Leu Leu Gly Gly Val
        115                 120                 125

Tyr Ile Glu Lys Asn Asp Lys Leu Cys His Met Asp Thr Ile Asp Trp
    130                 135                 140

Arg Asp Ile Val Arg Val Pro Asp Ala Glu Ile Val Val Lys Asn Asn
145                 150                 155                 160

Gly Gly Asn Cys Pro Pro Cys His Glu Val Cys Lys Gly Arg Cys Trp
                165                 170                 175

Gly Pro Gly Pro Glu Asp Cys Gln Ile Leu Thr Lys Thr Ile Cys Ala
            180                 185                 190

Pro Gln Cys Asn Gly Arg Cys Phe Gly Pro Asn Pro Asn Gln Cys Cys
        195                 200                 205

His Asp Glu Cys Ala Gly Gly Cys Ser Gly Pro Gln
    210                 215                 220
```